(12) United States Patent
Sengupta et al.

(10) Patent No.: US 10,905,781 B2
(45) Date of Patent: Feb. 2, 2021

(54) REPORTER PLATFORM FOR REAL TIME MONITORING OF DRUG EFFICACY

(71) Applicant: THE BRIGHAM AND WOMEN'S HOSPITAL, INC., Boston, MA (US)

(72) Inventors: Shiladitya Sengupta, Cambridge, MA (US); Ashish Kulkarni, Waltham, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 0 days.

(21) Appl. No.: 16/079,843

(22) PCT Filed: Mar. 2, 2017

(86) PCT No.: PCT/US2017/020440
§ 371 (c)(1),
(2) Date: Aug. 24, 2018

(87) PCT Pub. No.: WO2017/151912
PCT Pub. Date: Sep. 8, 2017

(65) Prior Publication Data
US 2019/0070318 A1 Mar. 7, 2019

Related U.S. Application Data

(60) Provisional application No. 62/302,435, filed on Mar. 2, 2016.

(51) Int. Cl.
*A61K 49/00* (2006.01)
*A61K 49/18* (2006.01)
*A61K 49/16* (2006.01)
*A61P 35/00* (2006.01)

(52) U.S. Cl.
CPC ...... *A61K 49/0054* (2013.01); *A61K 49/0058* (2013.01); *A61K 49/0093* (2013.01); *A61K 49/16* (2013.01); *A61K 49/1881* (2013.01); *A61P 35/00* (2018.01)

(58) Field of Classification Search
CPC ........... A61K 49/0054; A61K 49/1881; A61K 49/0093; A61K 49/0058; A61K 49/16; A61P 35/00
See application file for complete search history.

(56) References Cited

U.S. PATENT DOCUMENTS

2012/0189571 A1   7/2012  Sengupta
2015/0056137 A1   2/2015  Rao et al.

FOREIGN PATENT DOCUMENTS

WO   2015112092 A2   7/2015
WO   2015153345 A1   10/2015

OTHER PUBLICATIONS

Mizukami et al., "Imaging of caspase-3 activation in HeLa cells stimulated with etoposide using a novel fluorescent probe." FEBS Lett 453(3): 356-360 (1999).

*Primary Examiner* — Robert S Cabral
(74) *Attorney, Agent, or Firm* — Nixon Peabody LLP; David S. Resnick; Ravinderjit Braich

(57) ABSTRACT

Described herein is a reporter material platform that can be used to directly monitor the drug response in real-time. The reporter material can include an activator element which undergoes a chemical change in response to an immunonological response to a drug, and the chemical change can be detected using a reporter element. The reporter material can include a drug and a reporter element that are physically constrained in a close proximity. The reporter element produces a signal only when the drug induces a direct or indirect physiological change in the tumor or surrounding tissue. The reporter material platform can self-assemble via supramolecular interactions. This reporter material platform can be used to directly monitor the drug response in real-time.

11 Claims, 43 Drawing Sheets

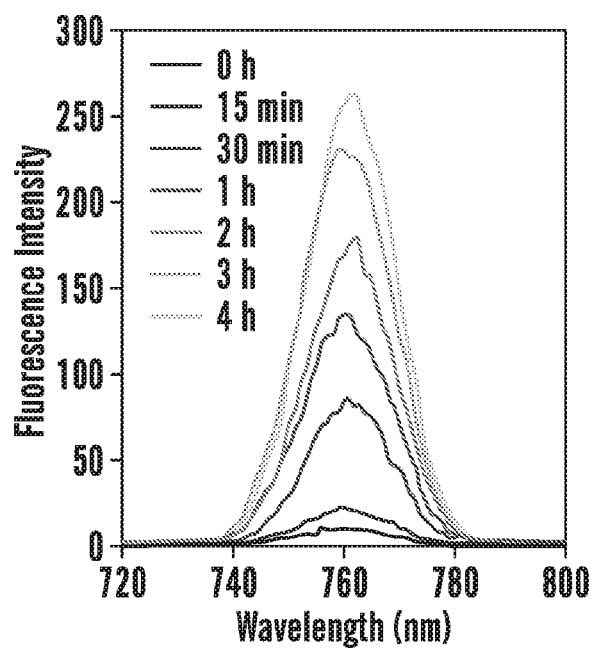
*FIG. 15A*
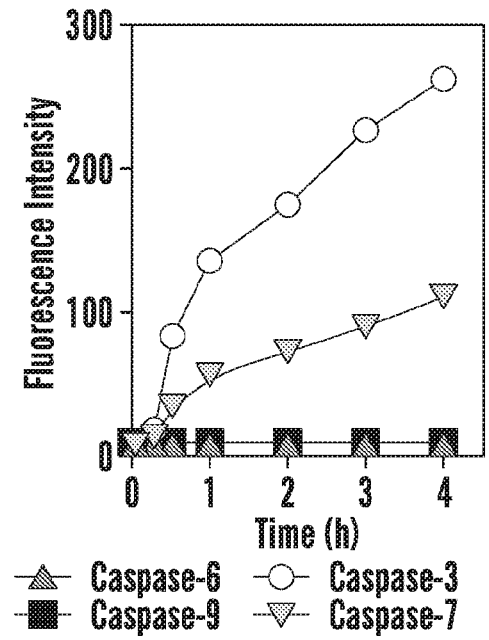
*FIG. 15B*
| EE:RE | Avg. Size (nm) | PDI |
|---|---|---|
| 7.5 : 7.5 | 32.36 | 0.670 |
| 10.5 : 4.5 | 28.45 | 0.612 |
| 13.5 : 1.5 | 126.6 | 0.331 |
| 14.5 : 0.5 | 186.8 | 0.232 |
*FIG. 15C*
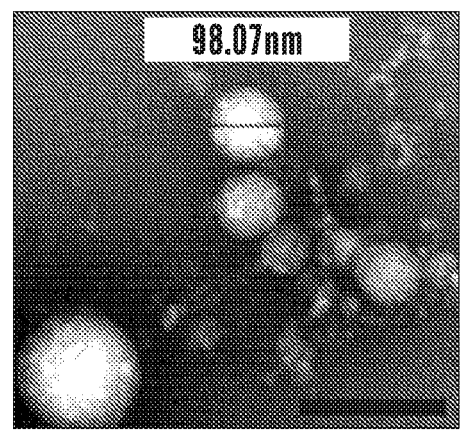
*FIG. 15D*

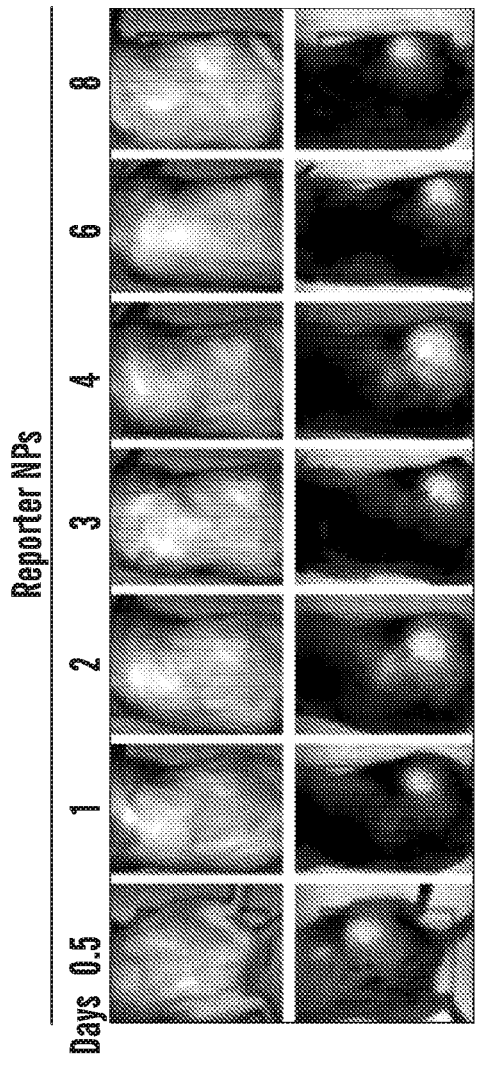
FIG. 17C
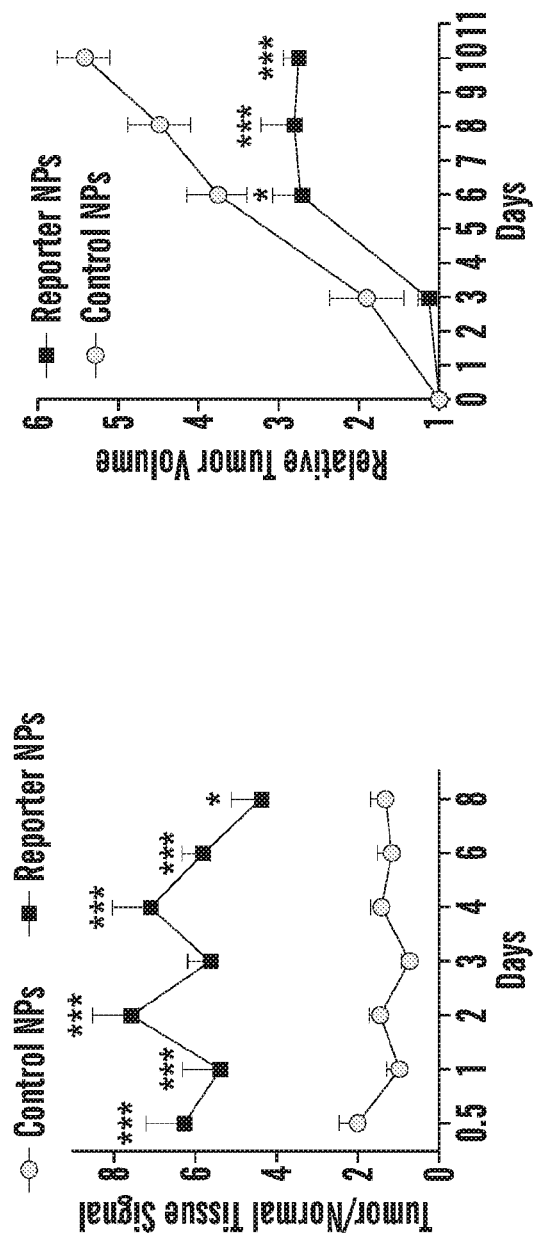
FIG. 17E
FIG. 17D

| Polymer | Pro-drug | Dia, nm |
|---------|----------|---------|
| 1 | 35 | 615 |
| 1 | 25 | 384 |
| 1 | 15 | 170±18 |
| 1 | 5 | 217 |

REPORTER PLATFORM FOR REAL TIME MONITORING OF DRUG EFFICACY

CROSS-REFERENCE TO RELATED APPLICATIONS

This application is a 371 National Phase Entry of International Patent Application No. PCT/US2017/020440 filed Mar. 2, 2017, which claims benefit under 35 U.S.C. § 119(e) of U.S. Provisional Application No. 62/302,435, filed Mar. 2, 2016, the contents of both of which are incorporated herein by reference in their entirety.

GOVERNMENT SUPPORT

This invention was made with government support under Grant No. 1R01CA135242 awarded by National Institutes of Health and Grant Nos. W81XWH-09-1-0700 and BC132168 awarded by the U.S. Department of Defense. The government has certain rights in this invention.

TECHNICAL FIELD

The invention described herein relates to reporter platform for realtime monitoring of drug efficacy. The invention also relates to the method of monitoring the efficacy of drug by using the reporter platform of the invention.

BACKGROUND

The failure of anticancer therapy is a major cause of mortality (Nature Communications, 2015, 6:6169). While the current dogma underlying resistance is based on the Darwinian selection of mutations acquired over time under chemotherapy pressure, emerging evidence indicates that anticancer drugs can be rendered ineffective early on by intrinsic or adaptive resistance as a function of tumor heterogeneity (Nature Reviews cancer, 2012, 12:323-334; Science, 2013, 339:543-548). For example, response rates to first line chemotherapy treatments in metastatic breast cancer patients range from a dismal 30% to 70%, and patients with disease progression need to be switched to a different drug (Journal of Nuclear Medicine, 2009, 50:55S-63S). Similarly, about 40-60% of patients with a wild type KRAS do not respond to cetuximab (New England Journal of Medicine, 2004, 351:337-345). Also, lower response rates have been observed with immunotherapy treatments. For example, PD1 blockade by Pembrolizumab induces response in—30% melanoma, 19% NSCLC, 20% of gastric and bladder cancers, and 16% in triple-negative breast cancer (Journal of Clinical Investigation, 2015, 125:3384-91). Thus, the ability to detect early whether a treatment is working or not, and switching to a regimen that is effective, can have a significant impact on the outcome as well as quality of life (The Lancet Oncology, 2014, 15:1415-1416; The Lancet Oncology, 2010, 11:92-102). However current approaches to quantify response rely on imaging techniques that fail to detect very early responses.

Several approaches have been developed to design materials that integrate both the imaging and therapeutic capabilities into single systems, termed theranostics, which allow the tracking of drug delivery to tumor or image-guided tumor ablation (ACS Nano, 2013, 7:2078; Advanced Drug Delivery Reviews, 2010, 62:284). However, despite the advances in the use of novel materials for drug delivery, in molecular imaging, and as theranostics, an area that has not been explored is the design of novel materials that merge the advantages of improved efficacy with the ability to self-monitor the anticancer activity in vivo.

SUMMARY

In one aspect, the invention provides an activatable system comprising an activator element. Generally, the activator element undergoes a chemical change in response to an immunonological response to a drug, and the chemical change can be detected using a reporter element.

In another aspect, the invention provides a polymer reporter material platform. Generally, the polymer reporte material platform compeises a polymer, a drug and a reporter element. The drug and the reporter element are in close proximity to each other. The reporter element generates a detectable signal in response to a physiological or chemical change induced by the drug in a tumor or surrounding environment. In some embodiments, the reporter element comprises the activator element. In some embodiments, the activator element comprises a first cleavable linker such that the first cleavable linker is cleaved only after the drug has induced a physiological or chemical change in a tumor or surrounding environment.

In another aspect, the invention provides a lipid-based reporter material platform. Generally, the lipid-based reporter material platform comprises a drug covalently linked to a first lipid and a reporter element covalently linked to a second lipid. The drug and the reporter element are in close proximity to each other. The reporter element generates a detectable signal in response to a physiological or chemical change induced by the drug in a tumor or surrounding environment. In some embodiments, the reporter element comprises the activator element. In some embodiments, the activator element comprises a first cleavable linker such that the first cleavable linker is cleaved only after the drug has induced a physiological or chemical change in a tumor or surrounding environment.

In yet another aspect, the invention provides a theranostic composition comprising an activatable system, a polymer reporter material platform or a lipid-based reporter material platform described herein.

In still another aspect, the invention provides a pharmaceutical composition comprising an activatable system, a polymer reporter material platform or a lipid-based reporter material platform described herein, and a pharmaceutically acceptable excipient or carrier.

In yet still another aspect, the invention provides a kit comprising an activatable system, a polymer reporter material platform or a lipid-based reporter material platform described herein, and packaging materials therefor.

In yet another aspect, the invention provides a method for treatment of a disease to a subject, the method comprising administering to a subject in need thereof an activatable system, a polymer reporter material platform or a lipid-based reporter material platform described herein.

In yet another aspect, the invention provides a method of monitoring efficacy of a drug, comprising administering an activatable system, a polymer reporter material platform or a lipid-based reporter material platform described herein; and measuring or detecting a detectable signal produced by the reporter element.

In still yet another aspect, the invention provides a method for determining susceptibility of a subject to the treatment regime, comprising administering an activatable system, a polymer reporter material platform or a lipid-based reporter material platform described herein; and measuring or detecting a detectable signal produced by the reporter element, wherein an increase in the detectable signal indicates that the subject is susceptible to treatment with the drug.

The detectable signal can be measured at any time after administering the activatable system, the polymer reporter material platform or the lipid-based reporter material platform to the subject. For example, the detectable signal can be measured after the drug has had sufficient time for inducing a change in the tumor or surrounding environment. In some embodiments, the detectable signal is measured after 8 hours of administration. In some embodiments, the detectable signal is measured after 24 hours of administration. In some embodiments, the detectable signal is measured after 7 days of administration.

BRIEF DESCRIPTION OF THE DRAWINGS

FIG. 15A is a graph showing the time-dependent activation of the reporter element (with the NIR FRET pair) in the presence of caspase-3. Reporter element (50 µM) was incubated in the presence of 50 U caspase-3 enzyme at 37° C., which results in the cleavage of the DEVD sequence and removing the quenching effect of Dylight 766Q on the fluorophore Dylight 755. The increase in fluorescence over time was monitored.

FIG. 15B is a graph showing the selective activation of the NIR-based fluorophore in reporter element by effector caspases (caspase-3 and caspase-7) compared with initiator caspases (caspase-6 and caspase-9).

FIG. 15C is a table showing the effect of optimization of ratio of the effector elements (EE) and reporter elements (RE) on the polymeric backbone on nanoparticle size and polydispersity, keeping the stimuli-responsive elements to polymer ratio of 15:1.

FIG. 15D is a representative high-resolution TEM image showing the morphology and the size of the nanoparticles. (Scale bar, 200 nm.)

FIG. 17C is a representative image showing reporter NP-treated groups at different time points.

FIG. 17D is a graph showing the quantification of tumor response to drug treatment as measured in terms of near-infrared fluorescence intensity ratio between tumor and normal tissues at different time intervals.

FIG. 17E is a graph showing the effect of treatment on 4T1 tumor-bearing mice treated with either control NPs or reporter NPs where tumor growth was quantified as change in relative tumor volume.

FIG. 21A shows representative images of 4T1 tumor bearing mice at 4 and 8 h after treatment with cytotoxic reporter NPs or combination of control NPs (NPs with only the reporter element) and paclitaxel NPs. When the tumor volume reached ~500 mm³, the animals were injected with reporter NPs (dose equivalent to 15 mg/kg paclitaxel) or combination of control NPs (equivalent dose of reporter element as reporter NPs) and paclitaxel NPs (dose equivalent to 15 mg/kg paclitaxel). The live mice imaging was done at different time points using a Maestro (CRI) in vivo fluorescence imaging system. FIG. 21B is a graph showing the quantification of tumor response when treated with reporter NPs vs. combination of control NPs and Pacli-NPs as measured in terms of near-infrared fluorescence intensity ratio between tumor and normal tissues at different time intervals. Data represent mean±SEM (n=3, P<0.01 vs. corresponding control-NP+ Pacli-NPs treated values for that time point, ANOVA followed by Bonferroni's post hoc test). FIG. 21C is [$^{18}$F]FDG PET and CT images of representative animals in reporter NPs and control-NPs+ Pacli-NPs treated groups before and 48 h after the treatment. The 4T1 breast tumor-bearing mice were treated with reporter NPs (equivalent to 15 mg/kg of paclitaxel) or control NPs (NPs with only the reporter element)+ Pacli-NPs. FIG. 21D is graph showing SUV max and % ID/mL for different treatment groups from the above study. Data represent mean±SEM (n=3). FIG. 21E is a growth curve showing effect of different multidose treatments on tumor volume. LLC tumor-bearing mice were injected with three doses of either control NPs (no paclitaxel) or 5FAM-based reporter NPs (dose equivalent of 15 mg/kg paclitaxel) on alternate days. First day of treatment was considered as day 0. Tumor volumes were measured on every alternate day for 6 d. End point for each animal was tumor size >2,000 cm³ or tumor ulceration, necrosis, or animal death. Data shown are mean±SEM (n=10, *P<0.001, ANOVA). FIG. 21F shows representative fluorescence images of the tumor sections at different time intervals and stained with cleaved caspase-3 antibody show overlay of caspase activity and activated FAM signal from the reporter nanoparticle, increasing with time.

FIG. 22A is a schematic showing the synthesis of PD-L1 reporter NPs. The reporter NPs were synthesized by conjugating Carboxy-(PEG)$_8$-amine and reporter element in optimized ratio to PIMA polymer followed by self-assembly in water. Then, PD-L1 antibody or control IgG antibody is conjugated to NPs using EDC-NHS conjugation chemistry. FIG. 22B is a graph showing optimization of PIMA polymer to carboxy-PEG$_8$ ratio in reporter NPs synthesis as measured by change in NPs diameter at different ratios. The optimized ratio was obtained at 1:10, PIMA:carboxy-PEG$_8$, which was used to synthesize PD-L1 reporter NPs and IgG-reporter NPs.

DETAILED DESCRIPTION

Figure 1A:
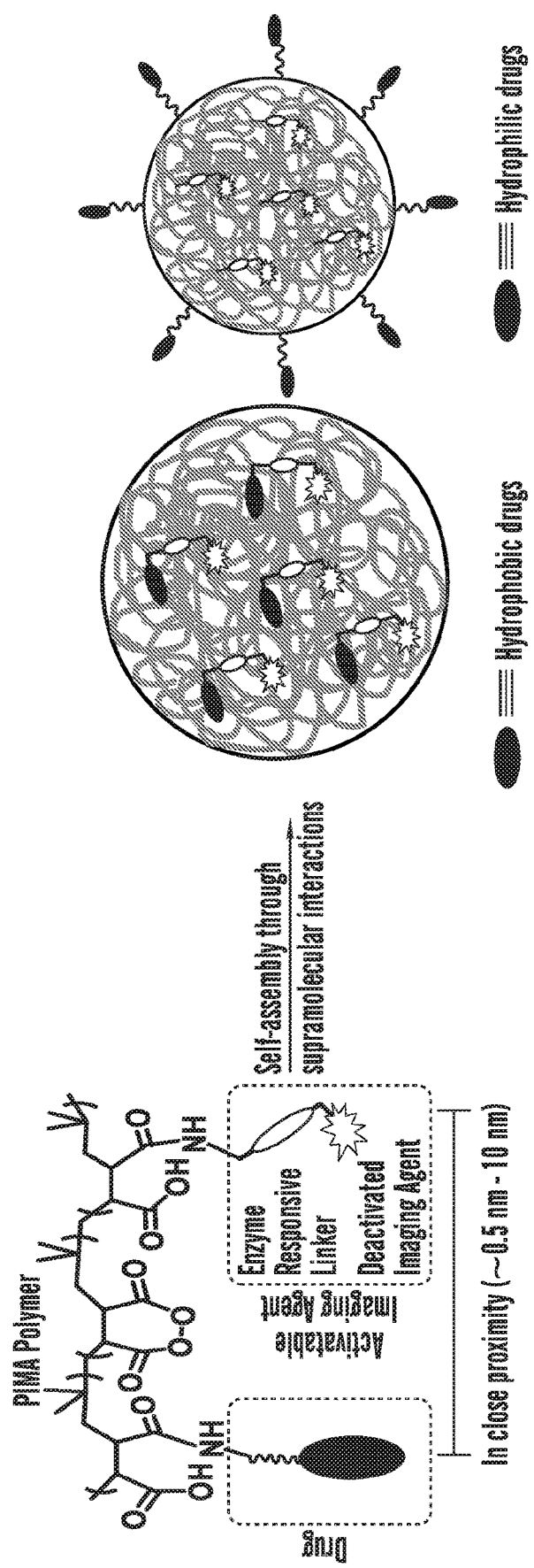
FIG. 1A is a schematic showing the synthesis of reporter material by conjugation of drug (hydrophilic or hydrophobic) and activatable imaging agent (reporter element) to PIMA polymer.

Described herein is the design of a stimuli-responsive structure, which is termed as a "reporter material." Generally, the reporter material comprises a drug and a reporter element. In some embodiments, the drug and the reporter element are maintained in close proximity by supramolecular interactions. This reporter material can self-assemble in structures such as nanostructures, hence, it's termed as reporter nanoparticle. These reporter nanoparticles internalize in the cancer cells and in the tumor efficiently. Such a reporter nanoparticle can start emitting a signal as early as 8 hours post-treatment in the case of chemotherapy, and can facilitate the distinction between responsive and resistant tumors in vivo. Additionally, it can be used to detect the efficacy of immune checkpoint inhibition at time points not accessible with current anatomic- or metabolic-based detection techniques. Thus, a reporter material can emerge as a powerful platform for not only enhancing the efficacy of cancer therapy but additionally provide a real-time noninvasive read out of tumor response to therapy.

In one aspect, the invention provides an activatable system comprising an activator element. The activator element undergoes a chemical change in response to an immunonological response to a drug, and the chemical change can be detected using a reporter element. Without limitations, the chemical change can include, but is not limited to, cleavage of a bond or modification of a molecule.

In some embodiments, the activator element comprises a substrate that is transformed by a biological change in an immune cell in response to a drug or a cancer cell in response to an activated immune cell.

In some embodiments, the activator element undergoes a chemical change in response to an enzyme. Exemplary enzymes include, but are not limited to, caspases and granzymes.

Without limitations, the activator element can be any molecule that undergoes a chemical change in response to an immunonological response to a drug. For example, the activator element can be a small molecule, a peptide or a polypeptide. In some embodiments, the activator element is a linker.

As used herein, a small molecule is typically characterized in that it contains several carbon-carbon bonds, and has a molecular weight more than about 50, but less than about 5000 Daltons (5 kD). Preferably the small molecule has a molecular weight of less than 3 kD, still more preferably less than 2 kD, and most preferably less than 1 kD. In some cases it is preferred that a small molecule have a molecular mass equal to or less than 700 Daltons.

As used herein, the term "peptide" is used in its broadest sense to refer to compounds containing two or more amino acids, amino acid equivalents or other non-amino groups joined to each other by peptide bonds or modified peptide bonds. Peptide equivalents can differ from conventional peptides by the replacement of one or more amino acids with related organic acids (such as PABA), amino acids or the like or the substitution or modification of side chains or functional groups. A peptide can be of any size long; however, in some embodiments, peptides having twenty or fewer total amino acids are preferred. Additionally, the peptide can be linear or cyclic.

In some embodiments, the actuator element comprises a peptide that undergoes cleavage in response to an immunonological response to a drug. In some embodiments, the peptide comprises the amino acid sequence DEVD (SEQ ID NO: 1)

In some embodiments of this and other aspects of the invention, the drug directly or indirectly increases the expression or amount of the enzyme. In a preferred embodiment of this and other aspects of the invention, the drug directly or indirectly increases the expression or amount of caspase-3 or granzyme.

In some embodiments of this and other aspects of the invention, the activatable system comprises a reporter element, wherein the activator element produces a detectable signal in response to the chemical change in the activator element. Without limitations, the activator element and the reporter element can be separately present in the activatable system or they can be covalently linked to each other.

In some embodiments of this and other aspects of the invention, the reporter element comprises an imaging agent or contrast agent.

As used herein, the term "imaging agent" refers to an element or functional group in a molecule that allows for the detection, imaging, and/or monitoring of the presence and/or progression of a condition(s), pathological disorder(s), and/or disease(s). The imaging agent may be an echogenic substance (either liquid or gas), non-metallic isotope, an optical reporter, a boron neutron absorber, a paramagnetic metal ion, a ferromagnetic metal, a gamma-emitting radioisotope, a positron-emitting radioisotope, or an x-ray absorber. As used herein the term "contrast agent" refers to any molecule that changes the optical properties of tissue or organ containing the molecule. Optical properties that can be changed include, but are not limited to, absorbance, reflectance, fluorescence, birefringence, optical scattering and the like.

Suitable optical reporters include, but are not limited to, fluorescent reporters and chemiluminescent groups. A wide variety of fluorescent reporter dyes are known in the art. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluorescein, rhodamine or other like compound. Suitable fluorescent reporters include xanthene dyes, such as fluorescein or rhodamine dyes, including, but not limited to, Alexa Fluor® dyes (InvitrogenCorp.; Carlsbad, Calif.), fluorescein, fluorescein isothiocyanate (FITC), Oregon Green™, rhodamine, Texas red, tetrarhodamine isothiocynate (TRITC), 5-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N',N'-tetramethyl-6-carboxyrhodamine (TAMRA), 6-carboxy-X-rhodamine (ROX). Suitable fluorescent reporters also include the naphthylamine dyes that have an amino group in the alpha or beta position. For example, naphthylamino compounds include 1-dimethylamino-naphthyl-5-sulfonate, 1-anilino-8-naphthalene sulfonate, 2-p-toluidinyl-6-naphthalene sulfonate, and 5-(2'-aminoethyl)aminonaphthalene-1-sulfonic acid (EDANS). Other fluorescent reporter dyes include coumarins, such as 3-phenyl-7-isocyanatocoumarin; acridines, such as 9-isothiocyanatoacridine and acridine orange; N-(p (2-benzoxazolyl)phenyl)maleimide; cyanines, such as Cy2, indodicarbocyanine 3 (Cy3), indodicarbocyanine 5 (Cy5), indodicarbocyanine 5.5 (Cy5.5), 3-(-carboxy-pentyl)-3'ethyl-5,5'-dimethyloxacarbocyanine (CyA); 1H,5H,11H, 15H-Xantheno[2,3,4-ij: 5,6,7-i'j']diquinolizin-18-ium, 9-[2 (or 4)-[[[6-[2,5-dioxo-1-pyrrolidinyl)oxy]-6-oxohexyl] amino]sulfonyl]-4(or 2)-sulfophenyl]-2,3,6,7,12,13,16, 17octahydro-inner salt (TR or Texas Red); BODIPY™ dyes; benzoxadiazoles; stilbenes; pyrenes; and the like. Many suitable forms of these fluorescent compounds are available and can be used. In some embodiments, the imaging or contrast agent is a coumarin.

Examples of fluorescent proteins suitable for use as imaging agents include, but are not limited to, green fluorescent protein, red fluorescent protein (e.g., DsRed), yellow fluorescent protein, cyan fluorescent protein, blue fluorescent protein, and variants thereof (see, e.g., U.S. Pat. Nos. 6,403,374, 6,800,733, and 7,157,566). Specific examples of GFP variants include, but are not limited to, enhanced GFP (EGFP), destabilized EGFP, the GFP variants described in Doan et al, Mol. Microbiol, 55:1767-1781 (2005), the GFP variant described in Crameri et al, Nat. Biotechnol., 14:315319 (1996), the cerulean fluorescent proteins described in Rizzo et al, Nat. Biotechnol, 22:445 (2004) and Tsien, Annu. Rev. Biochem., 67:509 (1998), and the yellow fluorescent protein described in Nagal et al, Nat. Biotechnol., 20:87-90 (2002). DsRed variants are described in, e.g., Shaner et al, Nat. Biotechnol., 22:1567-1572 (2004), and include mStrawberry, mCherry, mOrange, mBanana, mHoneydew, and mTangerine. Additional DsRed variants are described in, e.g., Wang et al, Proc. Natl. Acad. Sci. U.S.A., 101:16745-16749 (2004) and include mRaspberry and mPlum. Further examples of DsRed variants include mRFPmars described in Fischer et al, FEBS Lett., 577:227-232 (2004) and mRFPruby described in Fischer et al, FEBS Lett, 580:2495-2502 (2006).

Suitable echogenic gases include, but are not limited to, a sulfur hexafluoride or perfluorocarbon gas, such as perfluoromethane, perfluoroethane, perfluoropropane, perfluorobutane, perfluorocyclobutane, perfluropentane, or perfluorohexane.

Suitable non-metallic isotopes include, but are not limited to, $^{11}C$, $^{14}C$, $^{13}N$, $^{18}F$, $^{123}I$, $^{124}I$, and $^{125}I$.

Suitable radioisotopes include, but are not limited to, $^{99}Tc$, $^{95}Tc$, $^{111}In$, $^{62}Cu$, $^{64}Cu$, Ga, $^{68}Ga$, and $^{153}Gd$.

Suitable paramagnetic metal ions include, but are not limited to, Gd(III), Dy(III), Fe(III), and Mn(II).

Suitable X-ray absorbers include, but are not limited to, Re, Sm, Ho, Lu, Pm, Y, Bi, Pd, Gd, La, Au, Au, Yb, Dy, Cu, Rh, Ag, and Ir.

In some embodiments, the radionuclide is bound to a chelating agent. Suitable radionuclides for direct conjugation include, without limitation, $^{18}F$, $^{124}I$, $^{125}I$ $^{131}I$, and mixtures thereof. Suitable radionuclides for use with a chelating agent include, without limitation, $^{47}Sc$, $^{64}C$, $^{67}C$, $^{89}Sr$, $^{86}Y$, $^{87}Y$, $^{90}Y$, $^{105}Rh$, $^{111}Ag$, $^{111}In$, $^{7}Sn$, $^{149}Pm$, $^{153}Sm$, $^{166}Ho$, $^{177}Lu$, $^{186}Re$, $^{188}Re$, $^{211}At$, $^{212}Bi$, and mixtures thereof. Suitable chelating agents include, but are not limited to, DOTA, BAD, TETA, DTPA, EDTA, NTA, HDTA, their phosphonate analogs, and mixtures thereof.

In some embodiments of this and other aspects of the invention described herein, the reporter element comprises a Fluorescence Resonance Energy Transfer (FRET) based detection system. FRET requires at least two dye molecules: a first dye that serves as a FRET donor and a second dye that serves as a FRET acceptor. Typically, a FRET donor is an energy donor and a FRET acceptor is an energy acceptor. FRET is the energy transfer that takes place between the FRET donor and the FRET acceptor.

Fluorescent molecules having the proper emission and excitation spectra that are brought into close proximity with one another can exhibit FRET. FRET is the transfer of energy from a FRET donor to a FRET acceptor. This process occurs as follows: First, a FRET donor is excited, for example, using a picosecond laser pulse, and is converted, by absorption of energy in the form of a photon, from a ground state into an excited state. Second, the FRET donor emits this newly absorbed energy as fluorescent light. Third, if the excited donor molecule is close enough to a suitable acceptor molecule, the excited state can be transferred from the donor to the acceptor in the form of fluorescent light. This energy transfer is known as FRET. Fourth, FRET results in a decrease in the fluorescence or luminescence of the donor. Alternatively, if the acceptor is itself luminescent, results in an increased luminescence of the acceptor. The fluorescence or luminescence emitted by the acceptor can be measured.

In some embodiments of this and other aspects of the invention described herein, the reporter element comprises a fluorescent donor and an acceptor in close proximity to each other such that the acceptor quenches fluorescence of the donor. Exemplary donor-acceptor pairs include, but are not limited to, 5-FAM (visible range fluorophore)-QSY-7 (quencher) or Dylight 755 (neqar infrared fluorophore)-DyLight 766Q (quencher).

In some embodiments, the donor and the acceptor are linked to each other via the activator element.

In some embodiments, the donor and the acceptor are linked to each other via a linker, wherein the linker can under go cleavage only after a drug has induce an immunological, physiological or chemical change in a tumor or surrounding environment. Without wishing to be bound by a theory, cleavage of the linker releases the donor and acceptor from each other such that the acceptor no longer quenches the fluorescence of the donor.

In some embodiments of this and other aspects of the invention described herein, the reporter element comprises a magnetic resonance imaging (MRI) contrast agent or a positron emission tomography (PET) agent. An exemplary MRI contrast agent is a Gadolinium-DOTA based MRI contrast agent In some embodiments of this and other aspects of the invention, the activatable system is in the form of a nanoparticle.

As used herein, the term "nanoparticle" refers to particles that are on the order of $10^{-9}$ or one billionth of a meter and below $10^{-6}$ or 1 millionth of a meter in size. The term "nanoparticle" includes nanospheres; nanorods; nanoshells; and nanoprisms; and these nanoparticles may be part of a nanonetwork. The nanoparticle can be a regular or irregular shape. For example, the nanoparticle can be a spheroid, hollow spheroid, cube, polyhedron, prism, cylinder, rod, disc, lenticular, or other geometric or irregular shape.

In some embodiments of this and other aspects of the invention, the nanoparticles have an average diameter of from about 10 nm to about 500 nm. In some embodiments, the nanoparticles have an average diameter of from about 50 nm to about 250 nm. In one embodiment, the nanoparticles have an average diameter of from about 75 nm to about 250 nm. In some embodiments, the nanoparticles have an average diameter of about 100 nm. In some embodiments, the nanoparticles have an average diameter of about 200 nm.

In some embodiments of this and other aspects of the invention, the reporter nanoparticles are internalized in cancer cells and in tumor. In some embodiments, the reporter nanoparticles are not accumulated in the major reticuloendothelial organs, such as lung or spleen.

In another aspect, the invention provides a polymer reporter material platform. Generally, the polymer reporter material platform comprises a polymer, a drug and a reporter element. The drug and the reporter element are in close proximity to each other. The reporter element comprises a first cleavable linker such that the first cleavable linker is cleaved only after the drug has induced a physiological or chemical change in a tumor or surrounding environment and the reporter element generates a detectable signal upon cleavage of said cleavable linker.

In some embodiments, the polymer reporter material platform is in form of a particle, such as a nanoparticle. Without limitations, the polymer reporter material platform can self-assembles via supramolecular interactions to form a particle, e.g, a nanoparticle.

The cleavable linker comprised in the reporter element can be cleaved by an enzyme. For example, an enzyme whose expression or amount is increased by the drug. Exemplary such enzymes include, but are not limited to, caspases and granzymes. Accordingly, in some embodiments, the cleavable linker comprised in the reporter elements is cleaved by a caspase or granzyme.

The drug and the reporter element can be independently linked to the polymer. Accordingly, in some embodiments, the reporter element is covalently linked to the polymer. The linker connecting the reporter element to the polymer can be a cleavable linker, e.g., a second cleavable linker. In some embodiments, the first cleavable linker and the second cleavable linker are the same.

In some embodiments, the drug is covalently linked to the polymer. The linker connecting the reporter element to the polymer can be a cleavable linker, e.g. a third cleavable linker.

In some embodiments, the drug is covalently linked to the polymer by a linker or functional group selected from the group consisting of a PEG linker, maleimide linker, PASylation, HESylation, bis(sulfosuccinimidyl) suberate linker, nucleic acid linker, peptide linker, silane linker, polysaccharide linker, bond, amide bond, additions to carbon-carbon multiple bonds, azide alkyne Huisgen cycloaddition, Diels-Alder reaction, disulfide linkage, ester bond, Michael additions, silane bond, urethane, nucleophilic ring opening reactions: epoxides, non-aldol carbonyl chemistry, cycloaddition reactions: 1,3-dipolar cycloaddition, tosylation, temperature sensitive, radiation (IR, near-IR, UV) sensitive bond or linker, pH-sensitive bond or linker, and a hydrolyzable) linker.

In some embodiments, both the drug and the reporter element are covalently linked to the polymer.

Without limitations, any drug is amenable to use in the various aspects of the invention. For example, the drug can be a chemotherapeutic agent, targeted agent or immunotherapy agent.

As used herein the term "chemotherapeutic agent" refers to any chemical or biological agent with therapeutic usefulness in the treatment of diseases characterized by abnormal cell growth. Such diseases include tumors, neoplasms and cancer as well as diseases characterized by hyperplastic growth. These agents can function to inhibit a cellular activity upon which the cancer cell depends for continued proliferation. In some aspect of all the embodiments, a chemotherapeutic agent is a cell cycle inhibitor or a cell division inhibitor. Categories of chemotherapeutic agents that are useful in the methods of the invention include alkylating/alkaloid agents, antimetabolites, hormones or hormone analogs, and miscellaneous antineoplastic drugs. Most of these agents are directly or indirectly toxic to cancer cells. In one embodiment, a chemotherapeutic agent is a radioactive molecule. One of skill in the art can readily identify a chemotherapeutic agent of use (e.g. see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2nd ed. 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). In some embodiments, the chemotherapeutic agent can be a cytotoxic chemotherapeutic. The term "cytotoxic agent" as used herein refers to a substance that inhibits or prevents the function of cells and/or causes destruction of cells. The term is intended to include radioactive isotopes (e.g. At211, I131, I125, Y90, Re186, Re188, Sm153, Bi212, P32 and radioactive isotopes of Lu), chemotherapeutic agents, and toxins, such as small molecule toxins or enzymatically active toxins of bacterial, fungal, plant or animal origin, including fragments and/or variants thereof.

The term chemotherapeutic agent is a broad one covering many chemotherapeutic agents having different mechanisms of action. Generally, chemotherapeutic agents are classified according to the mechanism of action. Many of the available agents are anti-metabolites of development pathways of various tumors, or react with the DNA of the tumor cells. There are also agents which inhibit enzymes, such as topoisomerase I and topoisomerase II, or which are antimiotic agents.

Chemotherapeutic agents include, but are not limited to, an aromatase inhibitor; an antiestrogen, an anti-androgen (especially in the case of prostate cancer) or a gonadorelin agonist; a topoisomerase I inhibitor or a topoisomerase II inhibitor; a microtubule active agent, an alkylating agent, an anti-neoplastic anti-metabolite or a platin compound; a compound targeting/decreasing a protein or lipid kinase activity or a protein or lipid phosphatase activity, a further anti-angiogenic compound or a compound which induces cell differentiation processes; a bradykinin 1 receptor or an angiotensin II antagonist; a cyclooxygenase inhibitor, a bisphosphonate, a heparanase inhibitor (prevents heparan sulphate degradation), e.g., PI-88, a biological response modifier, preferably a lymphokine or interferons, e.g. interferon γ, an ubiquitination inhibitor or an inhibitor which blocks anti-apoptotic pathways; an inhibitor of Ras oncogenic isoforms or a farnesyl transferase inhibitor; a telomerase inhibitor, e.g., telomestatin; a protease inhibitor, a matrix metalloproteinase inhibitor, a methionine aminopeptidase inhibitor, e.g., bengamide or a derivative thereof; a proteasome inhibitor, e.g., PS-341 (bortezomib/Velcade); agents used in the treatment of hematologic malignancies or FMS-like tyrosine kinase inhibitors; an HSP90 inhibitors; histone deacetylase (HDAC) inhibitors; mTOR inhibitors; somatostatin receptor antagonists; integrin antagonists; anti-leukemic compounds; tumor cell damaging approaches, such as ionizing radiation; EDG binders; anthranilic acid amide class of kinase inhibitors; ribonucleotide reductase inhibitors; S-adenosylmethionine decarboxylase inhibitors; antibodies against VEGF or VEGFR; photodynamic therapy; angiostatic steroids; AT1 receptor antagonists; ACE inhibitors; and the like.

Other chemotherapeutic agents include, but are not limited to, plant alkaloids, hormonal agents and antagonists, biological response modifiers, preferably lymphokines or interferons, antisense oligonucleotides or oligonucleotide derivatives; or miscellaneous agents or agents with other or unknown mechanism of action.

The terms, "chemotherapeutic agents" and "chemotherapy agents" have been used interchangeably herein. In some embodiments, the chemotherapy agent is selected from the group consisting of paclitaxel; a platinum compound, carboplatin; bortezomib; vorinostat; rituximab; temozolomide; rapamycin; an alkylating agent; cyclosphosphamide; an alkyl sulfonate; busulfan; improsulfan; piposulfan; an aziridine; an ethylenimine; a methylamelamine; an acetogenin; a camptothecin; a cryptophycin; a nitrogen mustard; a nitrosurea; an antibiotic; a enediyne antibiotic; a bisphosphonate; doxorubicin; a mitomycin; an anti-metabolite; a folic acid analogue; a purine analog; a pyrimidine analog; an androgen; an anti-adrenal; an epothilone; a maytansinoid; a trichothecene; gemcitabine; 6-thioguanine; mercaptopurine; methotrexate; vinblastine; etoposide; ifosfamide; mitoxantrone; vincristine; vinorelbine; novantrone; teniposide; edatrexate; daunomycin; aminopterin; xeloda; ibandronate; irinotecan; a topoisomerase inhibitor; a retinoid; capecitabine; combretastatin; leucovorin; lapatinib; and erlotinib.

In some embodiments, the chemotherapeutic agent is a taxane. The term "Taxane" is generally referred to diterpene-containing compounds produced by the plants of the genus *Taxus* (e.g., yews, such as, but not limited to, *Taxus baccata*, Taxus brevifolia, Taxus canadensis, Taxus chinensis, Taxus cuspidata, Taxus floridana, Taxus globosa, Taxus sumatrana, Taxus walUchiana), and synthetic and semisynthetic forms thereof. The term denotes a compound containing the core structure

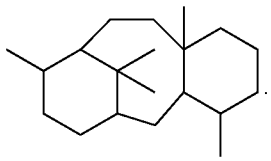 [SMILES: CC1CCCC2(C)CCC3C(C)CCC(CC12)C3(C)C]

The basic taxane core structure may further be substituted or may contain unsaturations in the ring to yield a number of compounds, generically known as taxanes. Generally, such compounds may block cell growth by stopping mitosis by interfering with microtubules. The term "diterpene," as used herein, means chemical compounds having a carbon skeleton derived from four isoprene units. The taxane group of compounds includes paclitaxel and docetaxel.

Taxanes can be isolated from natural sources, and can also be prepared synthetically from naturally occurring precursors. Paclitaxel (TAXOL®, Bnstol-Myers Squibb), for example, can be prepared from baccatin by attachment of protecting groups to the hydroxyl groups of baccatin that are to become the hydroxyl groups of paclitaxel, converting the precursor baccatin to paclitaxel, and then removing the protecting groups from the hydroxyl groups to obtain paclitaxel (see, e.g., WO93/10076. int. pub. date May 27, 1993; K. V. Rao, U.S. Pat. No. 5,200,534; R. A. Holton, U.S. Pat. No. 5,015,744; PCT US92/07990; V. J. Stella and A. E. Mathew, U.S. Pat. No. 4,960,790; K. C. Nicolau, Nature 3j54 (1993), pp. 464-466; Nicolau, K. C. et. al. Nature 367 (1994) pp. 630-634; Holton, R. A., et al. J. Am. Chem. Soc. H6 (1994) pp. 1597-1600; WO93/16059, int. pub. date Aug. 19, 1993; EP 528.729, published Feb. 24, 1993; EP 522,958, published Jan. 13, 1993; WO91/13053, int. pub. date Sep. 5, 1991; EP 414,610, int. pub. date Feb. 27, 1991; the contents of these documents are incorporated herein by reference). Non-limiting examples of taxanes can include paclitaxel and docetaxel, derivatives thereof, and mixtures thereof.

Taxanes can be used effectively to treat a variety of cancers. Paclitaxel, for example, has been found to have activity against ovarian and breast cancers, as well as against malignant melanoma, colon cancer, leukemias and lung cancer (see, e.g., Borman, Chemical & Engineering News, Sep. 2, 1991, pp. 11-18; The Pharmacological Basis of Therapeutics (Goodman Gilman et al., eds.), Pergamon Press, New York (1990), p. 1239; Suffness, Antitumor Alkaloids, in: "The Alkaloids, Vol. XXV," Academic Press, Inc. (1985), Chapter 1, pp. 6-18; Rizzo et al., J. Pharm. & Biomed. Anal. § (2):159-164 (1990); and Biotechnology 9:933-938 (October. 1991). Paclitaxel acts against cancer cells by binding to tubulin in the cells nuclei, thereby blocking the disassembly of microtubules and consequently, inhibiting cell division (Schiff et al., Nature 277:665 (1979). In one embodiment, the taxane is paclitaxel.

In some embodiments, the polymer reporter material platform further comprises a targeting agent or targeting ligand. The targeting ligand can be covalently linker to the polymer. For example, the targeting ligand can be covalently linker to the polymer via a cleavable or non-cleavable linker.

The terms "targeting ligand" and "targeting agent" are used interchangeably herein and refer to any molecule that provides an enhanced affinity for a selected target, e.g., a cell, cell type, tissue, organ, region of the body, or a compartment, e.g., a cellular, tissue or organ compartment. Some exemplary targeting ligands include, but are not limited to, antibodies, antigens, folates, receptor ligands, carbohydrates, aptamers, integrin receptor ligands, chemokine receptor ligands, transferrin, biotin, serotonin receptor ligands, PSMA, endothelin, GCPII, somatostatin, LDL and HDL ligands. In some embodiments, a targeting agent can bind to and/or penetrate a specific cell type(s) at a greater rate than to other cell types, e.g. cancer cells as compared to healthy cells.

Without limitation, the targeting agent is selected from the group consisting of peptides, polypeptides, proteins, enzymes, peptidomimetics, glycoproteins, antibodies (monoclonal or polyclonal) and portions and fragments thereof, lectins, nucleosides, nucleotides, nucleoside and nucleotide analogues, nucleic acids, monosaccharides, disaccharides, trisaccharides, oligosaccharides, polysaccharides, lipopolysaccharides, vitamins, steroids, hormones, cofactors, receptors, receptor ligands, and analogs and derivatives thereof.

In some embodiments, the immunotherapy agent is selected from the group consisting of anti-cancer agent, an anti-angiogenesis agent, a pro-angiogenesis agent, a vasodilator, a vasoconstrictor, an anti-neoplastic agent, an anti-proliferative agent, an anti-mitotic agent, an anti-migratory agent, an anti-adhesive agent, an anti-platelet agent, anti-thrombotic agent, a thrombolytic agent, a thrombogenic agent, an anti-inflammatory agent, anti-atherosclerosis agent, anti-infective agent, anti-sepsis agent, or an anti-polymerization agent.

The polymer reporter material can comprise additional components. Such additional components can include, but are not limited to, lipids, additional drugs, charged molecules and the like.

In some embodiments, the drug is a hydrophobic drug or a hydrophilic drug.

In some embodiments, the distance between the drug and the reporter element is 0.5 nm-10 nm.

As used herein, the term "polymer" refers to oligomers, co-oligomers, polymers and co-polymers, e.g., random block, multiblock, star, grafted, gradient copolymers and combination thereof. The average molecular weight of the polymer, as determined by gel permeation chromatography, can range from 20,000 to about 500,000. Without limitation, any polymeric material known in the art can be used in the invention. Accordingly, in some embodiments, the polymer is selected from the group consisting of polysaccharides, polypeptides, polynucleotides, copolymers of fumaric/sebacic acid, poloxamers, polylactides, polyglycolides, polycaprolactones, copolymers of polylactic acid and polyglycolic acid, polyanhydrides, polyepsilon caprolactone, polyamides, polyurethanes, polyesteramides, polyorthoesters, polydioxanones, polyacetals, polyketals, polycarbonates, polyorthocarbonates, polydihydropyrans, polyphosphazenes, polyhydroxybutyrates, polyhydroxyvalerates, polyalkylene oxalates, polyalkylene succinates, poly(malic acid), poly(amino acids), polyvinylpyrrolidone, polyethylene glycol, polyhydroxycellulose, polymethyl methacrylate, chitin, chitosan, copolymers of polylactic acid and polyglycolic acid, poly(glycerol sebacate) (PGS), gelatin, collagen, silk, alginate, cellulose, poly-nucleic acids, cellulose acetates (including cellulose diacetate), polyethylene, polypropylene, polybutylene, polyethylene terphthalate (PET), polyvinyl chloride, polystyrene, polyamides, nylon, polycarbonates, polysulfides, polysulfones, hydrogels (e.g., acrylics), polyacrylonitrile, polyvinylacetate, cellulose acetate butyrate, nitrocellulose, copolymers of urethane/carbonate, copolymers of styrene/maleic acid, poly(ethylenimine), hyaluron, heparin, agarose, pullulan, and copolymers, terpolymers, and copolymers comprising any combinations thereof.

In some embodiments, the polymer is a biocompatible polymer. As used herein, the term "biocompatible" means exhibition of essentially no cytotoxicity or immunogenicity while in contact with body fluids or tissues. The term "biocompatible polymer" refers to polymers which are non-toxic, chemically inert, and substantially non-immunogenic when used internally in a subject and which are substantially insoluble in blood. The biocompatible polymer can be either non-biodegradable or preferably biodegradable. Preferably, the biocompatible polymer is also noninflammatory when employed in situ.

Biodegradable polymers are disclosed in the art. Examples of suitable biodegradable polymers include, but are not limited to, linear-chain polymers such as polypeptides, polynucleotides, polysaccharides, polylactides, polyglycolides, polycaprolactones, copolymers of polylactic acid and polyglycolic acid, polyanhydrides, polyepsilon caprolactone, polyamides, polyurethanes, polyesteramides, polyorthoesters, polydioxanones, polyacetals, polyketals, polycarbonates, polyorthocarbonates, polydihydropyrans, polyphosphazenes, polyhydroxybutyrates, polyhydroxyvalerates, polyalkylene oxalates, polyalkylene succinates, poly(malic acid), poly(amino acids), polyvinylpyrrolidone, polyethylene glycol, polyhydroxycellulose, polymethyl methacrylate, chitin, chitosan, copolymers of polylactic acid and polyglycolic acid, poly(glycerol sebacate) (PGS), fumaric acid, sebacic acid, and copolymers, terpolymers including one or more of the foregoing. Other biodegradable polymers include, for example, gelatin, collagen, silk, chitosan, alginate, cellulose, poly-nucleic acids, etc.

Suitable non-biodegradable biocompatible polymers include, by way of example, cellulose acetates (including cellulose diacetate), polyethylene, polypropylene, polybutylene, polyethylene terphthalate (PET), polyvinyl chloride, polystyrene, polyamides, nylon, polycarbonates, polysulfides, polysulfones, hydrogels (e.g., acrylics), polyacrylonitrile, polyvinylacetate, cellulose acetate butyrate, nitrocellulose, copolymers of urethane/carbonate, copolymers of styrene/maleic acid, poly(ethylenimine), Poloxamers (e.g. Pluronic such as Poloxamers 407 and 188), Hyaluron, heparin, agarose, Pullulan, and copolymers including one or more of the foregoing, such as ethylene/vinyl alcohol copolymers (EVOH).

In some embodiments, the biocompatible polymer is a copolymer of polylactic acid and polyglycolic acid, poly(glycerol sebacate) (PGS), poly(ethylenimine), Pluronic (Poloxamers 407, 188), Hyaluron, heparin, agarose, or Pullulan In some embodiments, the polymer is a homopolymer, a copolymer or a block polymer.

In some embodiments, the polymer comprises sidechains selected from the group consisting of amide or ester groups. In some embodiments, the polymer is biodegradable, biocompatible and non-toxic.

In some embodiments, the polymer comprises maleic acid monomers. In some embodiments, the polymer is poly(isobutylene-alt-maleic acid) (PIMA).

The polymer can be derivatized with a second polymer and the first polymer and the second polymer can be the same or different. For example, the polymer can be derivatized with a polyethylene glycol (PEG). In some embodiments, the ratio of PIMA to PEG is 1:10. In some preferred embodiments, the ratio of PIMA to PEG to reporter element is 1:9:1.

As used herein, the term "linker" refers to a moiety that connects two parts of a compound. Linkers typically comprise a direct bond or an atom such as oxygen or sulfur, a unit such as $NR_1$, $C(O)$, $C(O)O$, $C(O)NR_1$, SO, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, $N(R_1)_2$, C(O), cleavable linking group, substituted or unsubstituted aryl, substituted or unsubstituted heteroaryl, substituted or unsubstituted heterocyclic; where $R_1$ is hydrogen, acyl, aliphatic or substituted aliphatic.

The linker can be a branched linker. The branch-point of the branched linker can be at least trivalent, but can be a tetravalent, pentavalent or hexavalent atom, or a group presenting such multiple valencies. In certain embodiments, the branch-point can be, —N, —N(Q)-C, —O—C, —S—C, —SS—C, —C(O)N(Q)-C, —OC(O)N(Q)-C, —N(Q)C(O)—C, or —N(Q)C(O)O—C; wherein Q is independently for each occurrence H or optionally substituted alkyl.

In various embodiments, the linker is a cleavable linker. A cleavable linker means that the linker can be cleaved to release the two parts the linker is holding together. A cleavable linker can be susceptible to cleavage agents, such as, but not limited to, enzymes, pH, redox potential or the presence of degradative molecules. As such, the cleavable linker is sufficiently intact until the drug induces an immunological response or a physiological or chemical change at the desired site. Generally, the cleavable linker is cleaved at least 1.25, 1.5, 1.75, 2, 3, 4, 5, 10, 25, 50, or 100 times faster after the drug induces an immunological response or a physiological or chemical change at the desired site. Generally, the drug elevates or increases the amount or expression of the cleavage agent. Examples of such agents: redox agents which are selected for particular substrates or which have no substrate specificity, including, e.g., oxidative or reductive enzymes or reductive agents such as mercaptans, present in cells, that can degrade a redox cleavable linking group by reduction; esterases; amidases; endosomes or agents that can create an acidic environment, e.g., those that result in a pH of five or lower; enzymes that can hydrolyze or degrade an acid cleavable linking group by acting as a general acid, peptidases (which can be substrate specific) and proteases, and phosphatases.

In some embodiments, the linker is polyethylene glycol.

In some embodiments, the linker is a peptide comprising the sequence DEVD (SEQ ID NO: 1). In a further embodiment, the linker is a peptide comprising the sequence KDEVDAP (SEQ ID NO: 2). In still a further embodiment, the linker is a peptide comprising the sequence GKDEVDAP (SEQ ID NO: 3).

In some embodiments, the cleavable linker is cleavable by an enzyme. For example, the cleavable linker can be cleaved by a caspase or granzyme.

In some embodiments, the cleavable linker is selected from a group consisting of small molecules. In some preferred embodiments, the cleavable linker is selected from a group consisting of peptides or polypeptides.

In another aspect, the invention provides a lipid-based reporter material platform. Generally, the lipid-based reporter material platform comprises a drug covalently linked to a first lipid and a reporter element covalently linked to a second lipid. The drug and the reporter element are in close proximity to each other. The reporter element comprises a first cleavable linker such that the first cleavable linker is cleaved only after the drug has induced a physiological or chemical change in a tumor or surrounding environment and the reporter element generates a detectable signal upon cleavage of said cleavable linker.

In some embodiments, the lipid-based reporter material platform is in form of a particle, such as a nanoparticle. Without limitations, the lipid-based reporter material platform can self-assembles via supramolecular interactions to form a particle, e.g., a nanoparticle.

In some embodiments, the drug is either a hydrophobic drug or a hydrophilic drug.

The drug can be covalently linked to the first lipid.

For example, the drug can be covalently linked to the first lipid by a linker or functional group selected from the group consisting of a PEG linker, maleimide linker, PASylation, HESylation, bis(sulfosuccinimidyl) suberate linker, nucleic acid linker, peptide linker, silane linker, polysaccharide linker, bond, amide bond, additions to carbon-carbon multiple bonds, azide alkyne Huisgen cycloaddition, Diels-Alder reaction, disulfide linkage, ester bond, Michael additions, silane bond, urethane, nucleophilic ring opening reactions: epoxides, non-aldol carbonyl chemistry, cycloaddition reactions: 1,3-dipolar cycloaddition, tosylation, temperature sensitive, radiation (IR, near-IR, UV) sensitive bond or linker, pH-sensitive bond or linker, and a hydrolyzable) linker.

In some preferred embodiments, the hydrophobic drugs can be conjugated to lipids including cholesterol. In some preferred embodiments, hydrophilic drugs such as antibodies and peptides can be conjugated to DSPE-PEG.

In some embodiments, the first cleavable linker comprised in the reporter element is cleaved by an enzyme. In some embodiments, the reporter element is covalently linked to the second lipid by a second cleavable linker. In some embodiments, the first cleavable linker and the second cleavable linker are the same.

An exemplary cleavable linker in the reporter element is a peptide comprising the amino acid sequence DEVD (SEQ ID NO: 1), KDEVDAP (SEQ ID NO: 2), and/or GKDEVDAP (SEQ ID NO: 3).

In some embodiments, the drug is covalently linked to the first lipid via a third cleavable linker.

In some embodiments, the first lipid and the second lipid are the same. In some embodiments, the first lipid and/or the second lipid is conjugated with polyethylene glycol. In some embodiments, the PEG conjugated lipid is selected from the group consisting of PEG conjugated diacylglycerols and dialkylglycerols, PEG-conjugated phosphatidylethanolamine and phosphatidic acid, PEG conjugated ceramides, PEG conjugated dialkylamines, PEG conjugated 1,2-diacyloxypropan-3-amines, and any combinations thereof. In some embodiments, the PEG conjugated lipid is 1,2-distearoyl-sn-glycem-3-phosphoethanolamine-N-[amino(polyethylene glycol)-2000](DSPE-PEG2000).

The lipid-based reporter material platform can also comprise further components. For example, the lipid-based reporter material platform can comprise a targeting agent or targeting ligand.

In some embodiments, the lipid-based reporter material platform can comprise additional lipids. For example, a third lipid in addition to the first and second lipid molecules that are covalently linked with the drug or the reporter element.

The term "lipid" as used herein means a substance that is soluble in organic solvents and includes, but is not limited to, oils, fats, sterols, triglycerides, fatty acids, phospholipids, and the like. The chemotherapeutic agent and the lipid can be covalently conjugated with each other using a reactive functional group present in their respective structures. The term "reactive functional group" refers to a functional group that is capable of reacting with another functional group. Exemplary reactive functional groups include, but are not limited to, hydroxyls, amines, thiols, thials, sulfinos, carboxylic acids, amides, and the like. The reactive functional group on the lipid and the chemotherapeutic agent can be the same or different. In some embodiments, the reactive group on the lipid is a hydroxyl, an amine, a thiol, or a carboxylic acid. In some embodiments, the reactive group on the chemotherapeutic agent is a hydroxyl, an amine, a thiol, or a carboxylic acid.

Without limitations the lipid can be selected from the group consisting of sterol lipids, fatty acids, fatty alcohols, glycerolipids (e.g., monoglycerides, diglycerides, and triglycerides), phospholipids, glycerophospholipids, sphingolipids, prenol lipids, saccharolipids, polyketides, and any combination thereof. The lipid can be a polyunsaturated fatty acid or alcohol. The term "polyunsaturated fatty acid" or "polyunsaturated fatty alcohol" as used herein means a fatty acid or alcohol with two or more carbon-carbon double bonds in its hydrocarbon chain. The lipid can also be a highly unsaturated fatty acid or alcohol. The term "highly polyunsaturated fatty acid" or "highly polyunsaturated fatty alcohol" as used herein means a fatty acid or alcohol having at least 18 carbon atoms and at least 3 double bonds. The lipid can be an omega-3 fatty acid. The term "omega-3 fatty acid" as used herein means a polyunsaturated fatty acid whose first double bond occurs at the third carbon-carbon bond from the end opposite the acid group.

In some embodiments, the lipid can be selected from the group consisting of cholesterol; 1,3-Propanediol Dicaprylate/Dicaprate; 10-undecenoic acid; 1-dotriacontanol; 1-heptacosanol; 1-nonacosanol; 2-ethyl hexanol; Androstanes; Arachidic acid; Arachidonic acid; arachidyl alcohol; Behenic acid; behenyl alcohol; Capmul MCM C10; Capric acid; capric alcohol; capryl alcohol; Caprylic acid; Caprylic/Capric Acid Ester of Saturated Fatty Alcohol C12-C18; Caprylic/Capric Triglyceride; Caprylic/Capric Triglyceride; Ceramide phosphorylcholine (Sphingomyelin, SPH); Ceramide phosphorylethanolamine (Sphingomyelin, Cer-PE); Ceramide phosphorylglycerol; Ceroplastic acid; Cerotic acid; Cerotic acid; ceryl alcohol; Cetearyl alcohol; Ceteth-10; cetyl alcohol; Cholanes; Cholestanes; cholesterol; cis-11-eicosenoic acid; cis-11-octadecenoic acid; cis-13-docosenoic acid; cluytyl alcohol; Dihomo-γ-linolenic; Docosahexaenoic acid; egg lecithin; Eicosapentaenoic acid; Eicosenoic acid; Elaidic acid; elaidolinolenyl alcohol; elaidolinoleyl alcohol; elaidyl alcohol; Erucic acid; erucyl alcohol; Estranes; Ethylene glycol distearate (EGDS); Geddic acid; geddyl alcohol; glycerol distearate (type I) EP (Precirol ATO 5); Glycerol Tricaprylate/Caprate; Glycerol Tricaprylate/Caprate (CAPTEX® 355 EP/NF); glyceryl monocaprylate (Capmul MCM C8 EP); Glyceryl Triacetate; Glyceryl Tricaprylate; Glyceryl Tricaprylate/Caprate/Laurate; Glyceryl Tricaprylate/Tricaprate; glyceryl tripalmitate (Tripalmitin); Henatriacontylic acid; Heneicosyl alcohol; Heneicosylic acid; Heptacosylic acid; Heptadecanoic acid; Heptadecyl alcohol; Hexatriacontylic acid; isostearic acid; isostearyl alcohol; Lacceroic acid; Lauric acid; Lauryl alcohol; Lignoceric acid; lignoceryl alcohol; Linoelaidic acid; Linoleic acid; linolenyl alcohol; linoleyl alcohol; Margaric acid; Mead; Melissic acid; melissyl alcohol; Montanic acid; montanyl alcohol; myricyl alcohol; Myristic acid; Myristoleic acid; Myristyl alcohol; neodecanoic acid; neoheptanoic acid; neononanoic acid; Nervonic; Nonacosylic acid; Nonadecyl alcohol; Nonadecylic acid; Nonadecylic acid; Oleic acid; oleyl alcohol; Palmitic acid; Palmitoleic acid; palmitoleyl alcohol; Pelargonic acid; pelargonic alcohol; Pentacosylic acid; Pentadecyl alcohol; Pentadecylic acid; Phosphatidic acid (phosphatidate, PA); Phosphatidylcholine (lecithin, PC); Phosphatidylethanolamine (cephalin, PE); Phosphatidylinositol (PI); Phosphatidylinositol bisphosphate (PIP2); Phosphatidylinositol phosphate (PIP); Phosphatidylinositol triphosphate (PIP3); Phosphatidylserine (PS); polyglyceryl-6-distearate; Pregnanes; Propylene Glycol Dicaprate; Propylene Glycol Dicaprylocaprate; Propylene Glycol Dicaprylocaprate; Psyllic acid; recinoleaic acid; recinoleyl alcohol; Sapienic acid; soy lecithin; Stearic acid; Stearidonic; stearyl alcohol; Tricosylic acid; Tridecyl alcohol; Tridecylic acid; Triolein; Undecyl alcohol; undecylenic acid; Undecylic acid; Vaccenic acid; α-Linolenic acid; and γ-Linolenic acid.

In some embodiments, the lipid is a neutral lipid, a cationic lipid, an anionic lipid, an amphiphilic lipid, a sterol, or a programmable fusion lipid.

Neutral lipids can be any of a number of lipid species which exist either in an uncharged or neutral zwitterionic form at physiological pH. Such lipids include, but are not limited to, diacylphosphatidylcholine, diacylphosphatidylethanolamine, ceramide, sphingomyelin, dihydrosphingomyelin, cephalin, and cerebrosides. Preferably, the neutral lipid component is a lipid having two acyl groups, (i.e., diacylphosphatidylcholine and diacylphosphatidylethanolamine). Lipids having a variety of acyl chain groups of varying chain length and degree of saturation are available or can be isolated or synthesized by well-known techniques. In one group of embodiments, lipids containing saturated or unsaturated fatty acids with carbon chain lengths in the range of $C_6$ to $C_{22}$ (e.g., $C_6$, $C_8$, $C_{10}$, $C_{12}$, $C_{14}$, $C_{16}$, $C_{18}$, $C_{22}$, or $C_{22}$) are preferred. Additionally, lipids having mixtures of saturated and unsaturated fatty acid chains can be used. In some embodiments, the neutral lipids can be phosphatidylcholine, DOPE, DSPC, POPC, DMPC, DPPC or any related phosphatidylcholine. The neutral lipids useful in the present invention can also be composed of sphingomyelin, dihydrosphingomyeline, or phospholipids with other head groups, such as serine and inositol.

The sterol component can be any of those sterols conventionally used in the field of liposome, lipid vesicle or lipid particle preparation. A preferred sterol is cholesterol.

The cationic lipids can be any of a number of lipid species which carry a net positive charge at about physiological pH. Such lipids include, but are not limited to, N,N-dioleyl-N,N-dimethylammonium chloride ("DODAC"); N-(2,3-dioleyloxy)propyl-N,N—N-triethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 1,2-Dioleyloxy-3-trimethylaminopropane chloride salt ("DOTAP.Cl"); 3β-(N—(N',N'-dimethylaminoethane)-carbamoyl)cholesterol ("DC-Chol"), N-(1-(2,3-dioleyloxy)propyl)-N-2-(sperminecarboxamido)ethyl)-N,N-dimethylammonium trifluoroacetate ("DOSPA"), dioctadecylamidoglycyl carboxyspermine ("DOGS"), 1,2-dileoyl-sn-3-phosphoethanolamine ("DOPE"), 1,2-dioleoyl-3-dimethylammonium propane ("DODAP"), N, N-dimethyl-2,3-dioleyloxy)propylamine ("DODMA"), N-(1,2-dimyristyloxyprop-3-yl)-N,N-dimethyl-N-hydroxyethyl ammonium bromide ("DMRIE"), 5-carboxyspermylglycine diocaoleyamide ("DOGS"), and dipalmitoylphosphatidylethanolamine 5-carboxyspermylamide ("DPPES"). Additionally, a number of commercial preparations of cationic lipids can be used, such as, e.g., LIPOFECTIN (including DOTMA and DOPE, available from GIBCO/BRL), and LIPOFECTAMINE (comprising DOSPA and DOPE, available from GIBCO/BRL). Other cationic lipids suitable for lipid particle formation are described in WO98/39359, WO96/37194. Other suitable cationic lipids are described, for example in US Patent Application Publication No. 2011/0997720 and PCT Patent Application Publication No. WO 2009/132131 and No. WO 2009/13213 1, content of all of which is incorporated herein by reference in its entirety.

When present in the reporter platform material, the anionic lipid can be any of a number of lipid species which carry a net negative charge at about physiological pH. Such lipids include, but are not limited to, phosphatidylglycerol, cardiolipin, diacylphosphatidylserine, diacylphosphatidic acid, N-dodecanoyl phosphatidylethanoloamine, N-succinyl phosphatidylethanolamine, N-glutaryl phosphatidylethanolamine, lysylphosphatidylglycerol, and other anionic modifying groups joined to neutral lipids.

As used herein, the term "amphipathic lipids" refer to any suitable material, wherein the hydrophobic portion of the lipid material orients into a hydrophobic phase, while the hydrophilic portion orients toward the aqueous phase. Such compounds include, but are not limited to, phospholipids, aminolipids, and sphingolipids.

Without limitations, the phospholipids can be of natural origin, such as egg yolk or soybean phospholipids, or synthetic or semisynthetic origin. The phospholipids can be partially purified or fractionated to comprise pure fractions or mixtures of phosphatidyl cholines, phosphatidyl cholines with defined acyl groups having 6 to 22 carbon atoms, phosphatidyl ethanolamines, phosphatidyl inositols, phosphatidic acids, phosphatidyl serines, sphingomyelin or phosphatidyl glycerols. Suitable phospholipids include, but are not limited to, phosphatidylcholine, phosphatidylglycerol, lecithin, β,γ-dipalmitoyl-α-lecithin, sphingomyelin, phosphatidylserine, phosphatidic acid, N-(2,3-di(9-(Z)-octadecenyloxy))-prop-1-yl-N,N,N-trimethylammonium chloride, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, palmitoyl-oleoyl-phosphatidylcholine, di-stearoyl-phosphatidylcholine, stearoyl-palmitoyl-phosphatidylcholine, di-palmitoyl-phosphatidylethanolamine, di-stearoyl-phosphatidylethanolamine, di-myrstoyl-phosphatidylserine, di-oleyl-phosphatidylcholine, dimyristoyl phosphatidyl choline (DMPC), dioleoylphosphatidylethanolamine (DOPE), palmitoyloleoylphosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), -phosphatidylethanolamine (POPE), dioleoyl-phosphatidylethanolamine 4-(N-maleimidomethyl)-cyclohexane-1-carboxylate (DOPE-mal), and the like. Non-phosphorus containing lipids can also be used. These include, e.g., stearylamine, docecylamine, acetyl palmitate, fatty acid amides, and the like. Other phosphorus-lacking compounds, such as sphingolipids, glycosphingolipid families, diacylglycerols, and 3-acyloxyacids, can also be used.

Also suitable for inclusion in the reporter platform material described herein are programmable fusion lipids. Particles containing programmable fusion lipids have little tendency to fuse with cell membranes and deliver their payload until a given signal event occurs. This allows the composition to distribute more evenly after administration into an organism or disease site before it starts fusing with cells. The signal event can be, for example, a change in pH, temperature, ionic environment, or time. In the latter case, a fusion delaying or "cloaking" component, such as an ATTA-lipid conjugate or a PEG-lipid conjugate, can simply exchange out of the particle membrane over time. By the time the particle is suitably distributed in the body, it has lost sufficient cloaking agent so as to be fusogenic. With other signal events, it is desirable to choose a signal that is associated with the disease site or target cell, such as lower pH at a site of tumor.

In some embodiments, the lipid-based reporter material platform further comprises a targeting agent or targeting ligand. The targeting ligand can be covalently linker to component of the lipid-based reporter material platform. For example, the targeting ligand can be covalently linker to a lipid in the reporter material platform via a cleavable or non-cleavable linker.

In yet another aspect, the invention provides a theranostic composition comprising an activatable system, a polymer reporter material platform or a lipid-based reporter material platform described herein. The term "theranostic" refers to the ability to determine the outcomes of a therapeutic procedure by using diagnostic devices and methods. Theranostics (a portmanteau of therapeutics and diagnostics) is a process of diagnostic therapy for individual patients—to test them for possible reaction to taking a medication and to tailor a treatment for them based on the test results. Theranostics can be a key part of personalized medicine and usually requires considerable advances in predictive medicine, and usually rely on pharmacogenomics, drug discovery using genetics, molecular biology and microarray chips technology. However, the compositions and methods described herein can be used for theranostic purposes without requiring any significant advances in predictive medicine or equipment.

In some embodiments, the technology described herein relates to a pharmaceutical composition comprising an activatable system, a polymer reporter material platform or a lipid-based reporter material platform described herein, and optionally a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. a composition as described herein.

In some embodiments, the pharmaceutical composition comprising a composition described herein, e.g. a nanoparticle as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of a composition as described herein are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt can also be incorporated into the parenteral dosage forms of the disclosure, including conventional and controlled-release parenteral dosage forms.

Pharmaceutical compositions as described herein can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug.

In certain embodiments, an effective dose of a composition as described herein can be administered to a patient once. In certain embodiments, an effective dose of a composition as described herein can be administered to a patient repeatedly. For systemic administration, subjects can be administered a therapeutic amount of a composition as described herein, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to a composition as described herein. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition as described herein can be administered over a period of time, such as over a 5 minute, 10 minute, 15 minute, 20 minute, or 25 minute period.

The dosage ranges for the administration of a composition as described herein, according to the methods described herein depend upon, for example, the form of a composition as described herein, its potency, and the extent to which symptoms, markers, or indicators of a condition described herein are desired to be reduced, for example the percentage reduction desired for tumor growth. The dosage should not be so large as to cause adverse side effects. Generally, the dosage will vary with the age, condition, and sex of the patient and can be determined by one of skill in the art. The dosage can also be adjusted by the individual physician in the event of any complication.

In yet another aspect, the invention provides a kit comprising an activatable system, a polymer reporter material platform or a lipid-based reporter material platform described herein, and packaging materials therefor.

In addition to the above mentioned components, the kit can include informational material. The informational material can be descriptive, instructional, marketing or other material that relates to the methods described herein. For example, the informational material describes methods for administering the composition to a subject. The kit can also include a delivery device.

In one embodiment, the informational material can include instructions to administer the formulation in a suitable manner, e.g., in a suitable dose, dosage form, or mode of administration (e.g., a dose, dosage form, or mode of administration described herein). In another embodiment, the informational material can include instructions for identifying a suitable subject, e.g., a human, e.g., an adult human. The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is a link or contact information, e.g., a physical address, email address, hyperlink, website, or telephone number, where a user of the kit can obtain substantive information about the formulation and/or its use in the methods described herein. Of course, the informational material can also be provided in any combination of formats.

In yet another aspect, the invention provides a method for treatment of a disease to a subject, the method comprising administering to a subject in need thereof an activatable system, a polymer reporter material platform or a lipid-based reporter material platform described herein.

In yet another aspect, the invention provides a method of monitoring efficacy of a drug, comprising administering an activatable system, a polymer reporter material platform or a lipid-based reporter material platform described herein; and measuring or detecting a detectable signal produced by the reporter element.

In still yet another aspect, the invention provides a method for determining susceptibility of a subject to the treatment regime, comprising administering an activatable system, a polymer reporter material platform or a lipid-based reporter material platform described herein; and measuring or detecting a detectable signal produced by the reporter element, wherein an increase in the detectable signal indicates that the subject is susceptible to treatment with the drug.

In one aspect, described herein is a method of treating cancer, comprising, administering a composition as described herein to a patient in need of treatment for cancer. In some embodiments, the cancer is selected from the group consisting of: breast cancer; ovarian cancer; glioma; gastrointestinal cancer; prostate cancer; carcinoma, lung carcinoma, hepatocellular carcinoma, testicular cancer; cervical cancer; endometrial cancer; bladder cancer; head and neck cancer; lung cancer; gastro-esophageal cancer, and gynecological cancer.

In some embodiments, the methods described herein relate to treating a subject having or diagnosed as having cancer. Subjects having cancer can be identified by a physician using current methods of diagnosing cancer. Symptoms and/or complications of cancer which characterize these conditions and aid in diagnosis are well known in the art and include but are not limited to, growth of a tumor, impaired function of the organ or tissue harboring cancer cells, etc. Tests that may aid in a diagnosis of, e.g. cancer include, but are not limited to, tissue biopsies and histological examination. A family history of cancer, or exposure to risk factors for cancer (e.g. tobacco products, radiation, etc.) can also aid in determining if a subject is likely to have cancer or in making a diagnosis of cancer.

Cancer can include, but is not limited to, carcinoma, including adenocarcinoma, lymphoma, blastoma, melanoma, sarcoma, leukemia, squamous cell cancer, small-cell lung cancer, non-small cell lung cancer, gastrointestinal cancer, Hodgkin's and non Hodgkin's lymphoma, pancreatic cancer, glioblastoma, basal cell carcinoma, biliary tract cancer, bladder cancer, brain cancer including glioblastomas and medulloblastomas; breast cancer, cervical cancer, choriocarcinoma; colon cancer, colorectal cancer, endometrial carcinoma, endometrial cancer; esophageal cancer, gastric cancer; various types of head and neck cancers, intraepithelial neoplasms including Bowen's disease and Paget's disease; hematological neoplasms including acute lymphocytic and myelogenous leukemia; Kaposi's sarcoma, hairy cell leukemia; chromic myelogenous leukemia, AIDS-associated leukemias and adult T-cell leukemia lymphoma; kidney cancer such as renal cell carcinoma, T-cell acute lymphoblastic leukemia/lymphoma, lymphomas including Hodgkin's disease and lymphocytic lymphomas; liver cancer such as hepatic carcinoma and hepatoma, Merkel cell carcinoma, melanoma, multiple myeloma; neuroblastomas; oral cancer including squamous cell carcinoma; ovarian cancer including those arising from epithelial cells, sarcomas including leiomyosarcoma, rhabdomyosarcoma, liposarcoma, fibROS1arcoma, and osteosarcoma; pancreatic cancer; skin cancer including melanoma, stromal cells, germ cells and mesenchymal cells; pROS1tate cancer, rectal cancer; vulval cancer, renal cancer including adenocarcinoma; testicular cancer including germinal tumors such as seminoma, non-seminoma (teratomas, choriocarcinomas), stromal tumors, and germ cell tumors; thyroid cancer including thyroid adenocarcinoma and medullar carcinoma; esophageal cancer, salivary gland carcinoma, and Wilms' tumors.

The compositions and methods described herein can be administered to a subject having or diagnosed as having cancer. In some embodiments, the methods described herein comprise administering an effective amount of compositions described herein to a subject in order to alleviate a symptom of a cancer. As used herein, "alleviating a symptom of a cancer" is ameliorating any condition or symptom associated with the cancer. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, injection, or intratumoral administration. Administration can be local or systemic.

The term "effective amount" as used herein refers to the amount of a composition described herein needed to alleviate at least one or more symptom of the disease or disorder, and relates to a sufficient amount of pharmacological composition to provide the desired effect. The term "therapeutically effective amount" therefore refers to an amount of a composition described herein that is sufficient to provide a particular anti-tumor effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of a composition described herein, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for tumor size and/or growth, among others. The dosage can be determined by a physician and adjusted, as necessary, to suit observed effects of the treatment.

The efficacy of a composition as described herein in, e.g. the treatment of a condition described herein, or to induce a response as described herein can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. tumor size and/or growth. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g. tumor size and/or growth). It is well within the ability of one skilled in the art to monitor efficacy of administration and/or treatment by measuring any one of such parameters, or any combination of parameters. Efficacy can be assessed in animal models of a condition described herein, for example treatment of cancer. When using an experimental animal model, efficacy of treatment is evidenced when a statistically significant change in a marker is observed, e.g. a decreased in tumor size and/or growth.

In vitro and animal model assays are provided herein which allow the assessment of a given dose of a composition as described herein. By way of non-limiting example, the effects of a dose of a composition can be assessed by an in vitro cell viability assay.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of cancer. A subject can be male or female.

A subject can be one who has been previously diagnosed with or identified as suffering from or having a condition in need of treatment (e.g. cancer) or one or more complications related to such a condition, and optionally, have already undergone treatment for cancer or the one or more complications related to cancer. Alternatively, a subject can also be one who has not been previously diagnosed as having cancer or one or more complications related to cancer. For example, a subject can be one who exhibits one or more risk factors for cancer or one or more complications related to cancer or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. cancer. The term "treating" includes reducing or alleviating at least one adverse effect or symptom of a condition, disease or disorder associated with a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

As used herein, the term "amphiphilic" refers to a molecule that has both a hydrophobic portion and a lipophobic portion, i.e. at least one a polar, water-soluble group and at least one a nonpolar, water-insoluble group. Typically, in a two phase system having a polar, aqueous phase and a non-polar, non-aqueous phase, an amphiphilic molecule will partition to the interface of the two phases. In simpler non limiting terms, an amphiphile is a molecule that is soluble in both an aqueous environment and a non-aqueous environment. The term "amphiphile" refers to an amphiphilic molecule.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Some embodiments of the technology described herein can be defined according to any of the following numbered paragraphs:

1. An activatable system comprising an activator element, wherein the activator element undergoes a chemical change in response to an immunonological response to a drug, and wherein said chemical change can be detected using a reporter element.
2. The activatable system of paragraph 1, wherein the activator element comprises a substrate that is transformed by a biological change in an immune cell in response to a drug or a cancer cell in response to an activated immune cell.
3. The activatable system of paragraph 1 or 2, wherein the activator element undergoes said chemical change in response to an enzyme.
4. The activatable system of any one of paragraphs 1-3, wherein the drug directly or indirectly increases the expression or amount of the enzyme.
5. The activatable system of any one of paragraphs 1-4, wherein the activatable system comprises the reporter element.
6. The activatable system of any one of paragraphs 1-5, wherein the activator element and the reporter element are covalently linked to each other.
7. The activatable system of any one of paragraphs 1-6, wherein the activatable system is in the form of a nanoparticle.
8. The activatable system of any one of paragraphs 1-7, wherein the reporter element comprises a fluorescent molecule, an optical reporter, a paramagnetic metal ion, a ferromagnetic metal, a gamma-emitting radioisotope, a positron-emitting radioisotope, an x-ray absorber, an echogenic substance, a non-metallic isotope, or a boron neutron absorber.
9. The activatable system of any one of paragraphs 1-8, wherein the reporter element comprises a fluorescent donor and an acceptor in close proximity to each other such that the acceptor quenches fluorescence of the donor.
10. The activatable system of any one of paragraphs 1-9, wherein the fluorescent donor and the acceptor are linked to each other via the activator element.
11. A polymer reporter material platform comprising a polymer, a drug and a reporter element, wherein the drug and the reporter element are in close proximity to each other, and wherein the reporter element comprises a first cleavable linker such that the first cleavable linker is cleaved only after the drug has induced a physiological or chemical change in a tumor or surrounding environment and the reporter element generates a detectable signal upon cleavage of said cleavable linker.
12. The polymer reporter material platform of paragraph 11, wherein the distance between the drug and the reporter element is 0.5 nm-10 nm.
13. The polymer reporter material platform of paragraph 11 or 12, wherein the reporter material platform is in the form of a nanoparticle.
14. The polymer reporter material platform of any one of paragraphs 11-13, wherein said cleavable linker comprised in the reporter elements is cleaved by an enzyme.
15. The polymer reporter material platform of paragraph 14, wherein the drug increases the expression or amount of the enzyme.
16. The polymer reporter material platform of any one of paragraphs 11-15, wherein the reporter element is covalently linked to the polymer.
17. The polymer reporter material platform of any one of paragraphs 11-16, wherein the reporter element is covalently linked to the polymer by a second cleavable linker.
18. The polymer reporter material platform of paragraph 17, wherein the first cleavable linker and the second cleavable linker are the same.
19. The polymer reporter material platform of any one of paragraphs 11-18, wherein the reporter element comprises a fluorescent molecule, an optical reporter, a paramagnetic metal ion, a ferromagnetic metal, a gamma-emitting radioisotope, a positron-emitting radioisotope, an x-ray absorber, an echogenic substance, a non-metallic isotope, or a boron neutron absorber.
20. The polymer reporter material platform of any one of paragraphs 11-19, wherein the reporter element comprises a fluorescent donor and an acceptor in close proximity to each other such that the acceptor quenches fluorescence of the donor.
21. The polymer reporter material platform of paragraph 20, wherein the fluorescent donor and the acceptor are linked to each other via the first cleavable linker.
22. The polymer reporter material platform of any one of paragraphs 11-19, wherein the reporter element comprises a magnetic resonance imaging (MRI) contrast agent or a positron emission tomography (PET) agent.
23. The polymer reporter material platform of any one of paragraphs 11-22, wherein the drug is covalently linked to the polymer.
24. The polymer reporter material platform of any one of paragraphs 11-23, wherein the drug is covalently linked to the polymer via a third cleavable linker.
25. The polymer reporter material platform of any one of paragraphs 11-24, wherein the drug is a chemotherapy agent or an immunotherapy agent.
26. The polymer reporter material platform of any one of paragraphs 11-25, further comprising a targeting ligand or a targeting agent.
27. The polymer reporter material platform of any one of paragraphs 11-26, wherein the polymer is a homopolymer, a copolymer or a block polymer.
28. The polymer reporter material platform of any one of paragraphs 11-27, wherein said polymer comprises maleic acid monomers.
29. The polymer reporter material platform of any one of paragraphs 11-28, wherein the polymer is poly(isobutylene-alt-maleic acid) (PIMA).
30. The polymer reporter material platform of any one of paragraphs 11-29, wherein the polymer is derivatized with a polyethylene glycol (PEG).
31. A lipid-based reporter material platform comprising a drug covalently linked to a first lipid and a reporter element covalently linked to a second lipid, wherein the drug and the reporter element are in close proximity to each other, and wherein the reporter element comprises a first cleavable linker such that the first cleavable linker is cleaved only after the drug has induced a physiological or chemical change in a tumor or surrounding environment and the reporter element generates a detectable signal upon cleavage of said cleavable linker.
32. The lipid-based reporter material platform of paragraph 31, wherein the distance between the drug and the reporter element is 0.5 nm-10 nm.
33. The lipid-based reporter material platform of paragraph 31 or 32, wherein the reporter material platform is in the form of a nanoparticle.
34. The lipid-based reporter material platform of any one of paragraphs 31-33, wherein said cleavable linker comprised in the reporter elements is cleaved by an enzyme.
35. The lipid-based reporter material platform of paragraph 34, wherein the drug increases the expression or amount of the enzyme.
36. The lipid-based reporter material platform of any one of paragraphs 31-35, wherein the reporter element is covalently linked to the second lipid by a second cleavable linker.
37. The lipid-based reporter material platform of paragraph 36, wherein the first cleavable linker and the second cleavable linker are the same.
38. The lipid-based reporter material platform of any one of paragraphs 31-37, wherein the reporter element comprises a fluorescent molecule, an optical reporter, a paramagnetic metal ion, a ferromagnetic metal, a gamma-emitting radioisotope, a positron-emitting radioisotope, an x-ray absorber, an echogenic substance, a non-metallic isotope, or a boron neutron absorber.
39. The lipid-based reporter material platform of any one of paragraphs 31-38, wherein the reporter element comprises a magnetic resonance imaging (MRI) contrast agent or a positron emission tomography (PET) agent.
40. The lipid-based reporter material platform of any one of paragraphs 31-39, wherein the reporter element comprises a fluorescent donor and an acceptor in close proximity to each other such that the acceptor quenches fluorescence of the donor.
41. The lipid-based reporter material platform of paragraph 40, wherein the fluorescent donor and the acceptor are linked to each other via the first cleavable linker.

42. The lipid-based reporter material platform of any one of paragraphs 31-41, wherein the drug is covalently linked to the lipid.
43. The lipid-based reporter material platform of any one of paragraphs 31-42, wherein the drug is covalently linked to the lipid via a third cleavable linker.
44. The lipid-based reporter material platform of any one of paragraphs 31-43, wherein the drug is a chemotherapy agent or an immunotherapy agent.
45. The lipid-based reporter material platform of any one of paragraphs 31-44, further comprising a targeting ligand or a targeting agent.
46. The lipid-based reporter material platform of any one of paragraphs 31-45, wherein the first lipid and the second lipid are the same.
47. The lipid-based reporter material any one of paragraphs 31-46, wherein the first lipid and/or the second lipid is conjugated with polyethylene glycol.
48. The lipid-based reporter material platform of any one of paragraphs 31-47, wherein the drug is selected from the group consisting of chemotherapy agent, targeted agent or immunotherapy agent.

To the extent not already indicated, it will be understood by those of ordinary skill in the art that any one of the various embodiments herein described and illustrated may be further modified to incorporate features shown in any of the other embodiments disclosed herein.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

EXAMPLES

Figure 1B:
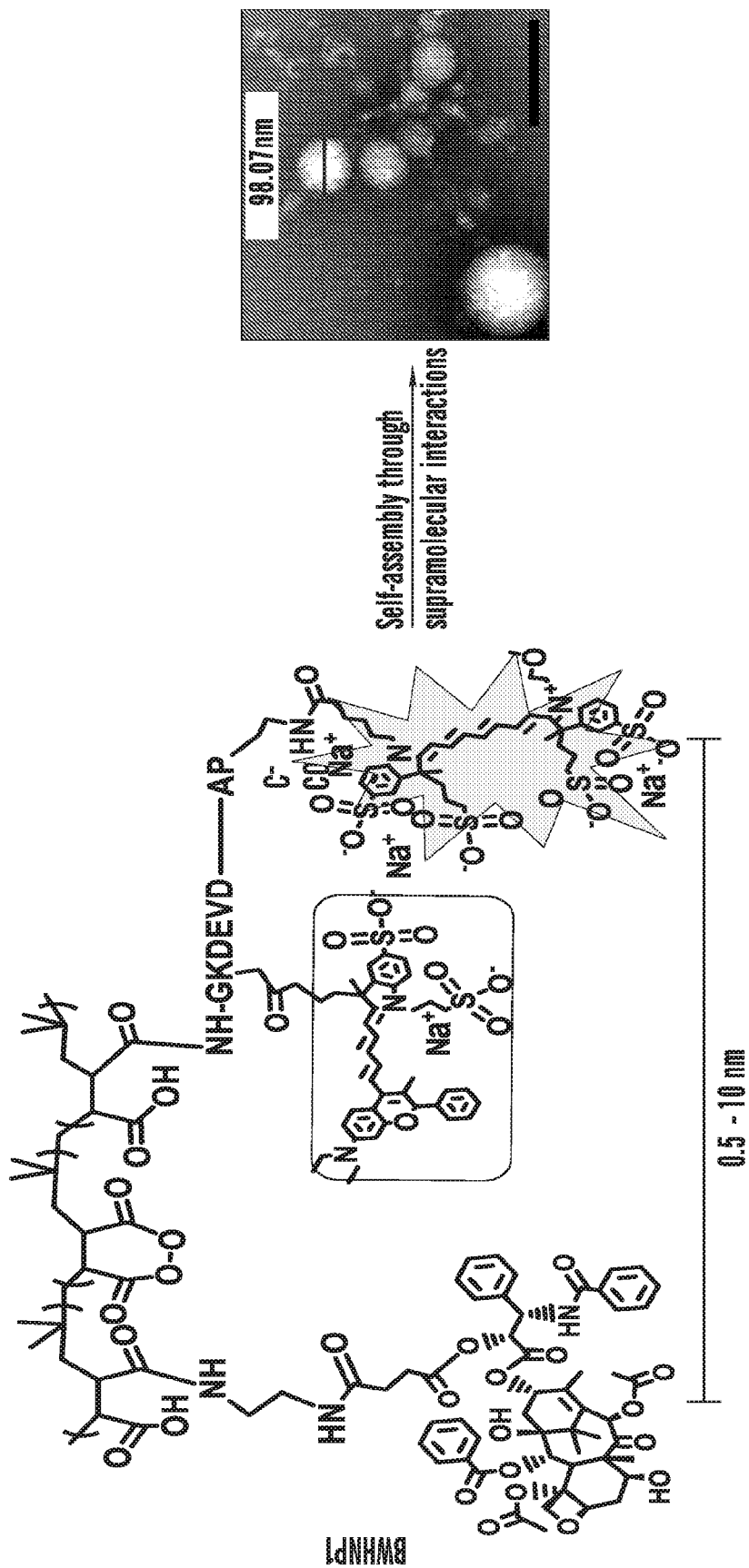
FIG. 1B is a schematic showing synthesis of reporter material with chemotherapy drug and caspase activatable FRET-based reporter element conjugated to PIMA polymer. At the optimal drug to reporter element ratio, this polymer self-assembles into a nanoparticle of 100 nm size. The reporter element is a caspase-3 cleavable sequence consisting of L-amino acids GKDEVDAPC-CONH$_2$ to which a NIR FRET-pair is conjugated such that cleavage of the DEVD sequence results in removal of the quenching of the fluorescent signal.

Example 1: Reporter Material from poly[iso-butylene-alt-(maleic anhydride)} (PIMA) polymer A reporter material from poly[iso-butylene-alt-(maleic anhydride)] (PIMA) polymer has been designed as shown in FIG. 1A. The reporter material can self-assemble via supramolecular interactions to any structure or any shape. The close proximity of the drug and activatable reporter element is maintained by covalent conjugation and supramolecular interactions. The drug can be any anticancer agent including chemotherapy agent, targeted agent or immunotherapy agent. The enzymes can be caspases or granzymes. The activatable imaging agent includes fluorescent, MRI or PET imaging agents. In normal condition, the signal from the reporter element is in "Off" state, since the drug is intact inside the reporter material. The reporter material is in the tumor once the material is internalized by cancer cell. In a drug-sensitive cell, the released drug initiates physiological changes in tumor such as apoptosis resulting in activation of caspase-3 levels or immune activation resulting in higher granzyme B levels, which then cleaves the enzyme responsive linker and activating the signal ("On" state). However, in a non-responder cell, the failure of the released drug to induce physiological changes means the reporter element remains in "Off" state. This distinction between Off and On states allows the visualization of a therapy response in action. In an example, the cytotoxic drug and reporter element are covalently conjugated to the PIMA polymer at optimized ratios to maintain the close proximity and show that the polymer construct self-assembles to nanostructure (termed as BWHNP1) via supramolecular interactions (FIG. 1B). The reporter element was designed using a short peptide containing a caspase-3-cleavable Asp-Glu-Val-Asp (DEVD) sequence inserted between either the Forster resonance energy transfer (FRET) pair of 5-FAM (visible-range fluorophore) and QSY-7 (quencher) or the pair of DyLight 755 (near-infrared fluorophore) and DyLight 766Q (quencher).

Example 2: Internalization of Reporter Nanoparticle in the Cancer Cells

Figure 2:
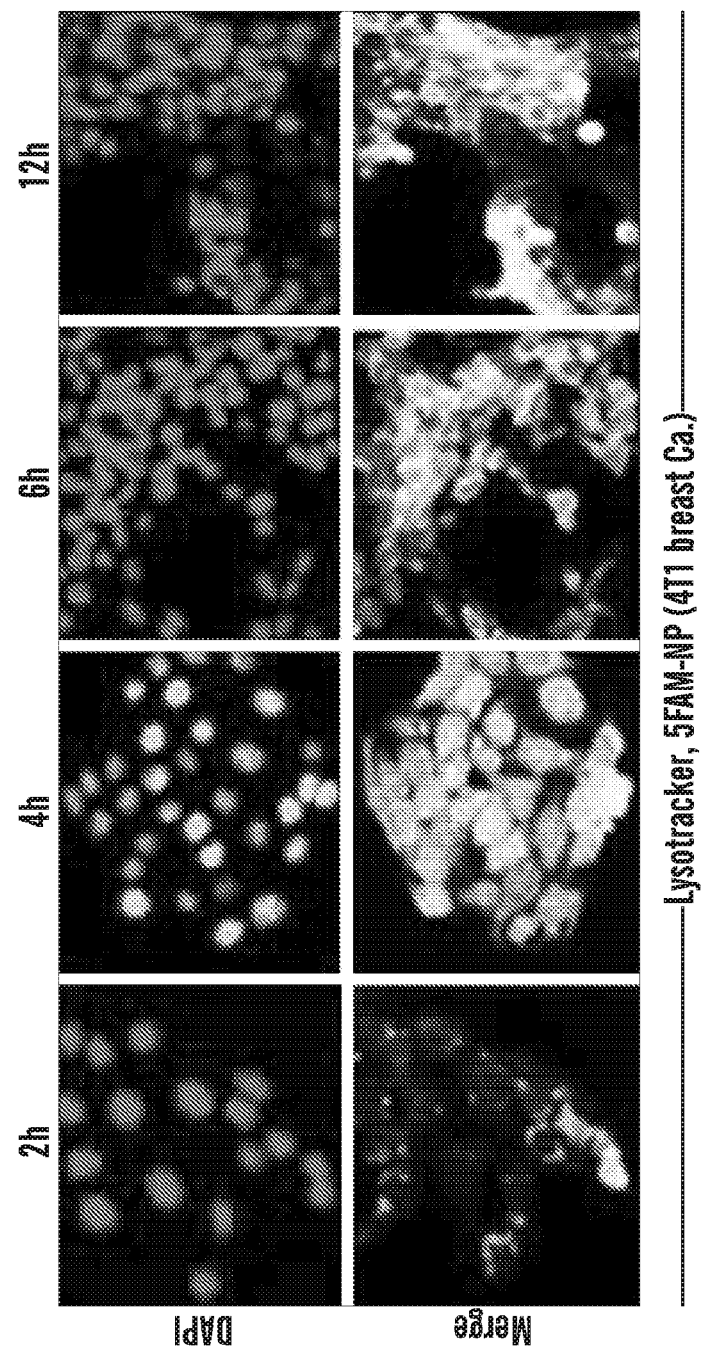
FIG. 2 is a representative fluorescence merge-image showing the internalization of 5-FAM-labeled nanoparticles at different time points in 4T1 breast cancer cells. Nuclei of the cells were labeled with DAPI (blue) and acidic endolysosomes were labeled with LysoTracker (Red). The overlay indicates that the reporter nanoparticles are rapidly internalized via an endolysosomal pathway.

The 4T1 breast cancer cells were incubated with reporter nanoparticles for different time points to study their internalization in cancer cells. Monitoring the internalization of FAM-tagged nanoparticles into the cancer cells revealed a temporal uptake of the nanoparticles via the endolysosomal pathway (FIG. 2). This could lead to higher efficacy and real time monitoring of drug response.

Example 3: In Vitro Validation of BWHNP1 Reporter Nanoparticles

Figure 3A:
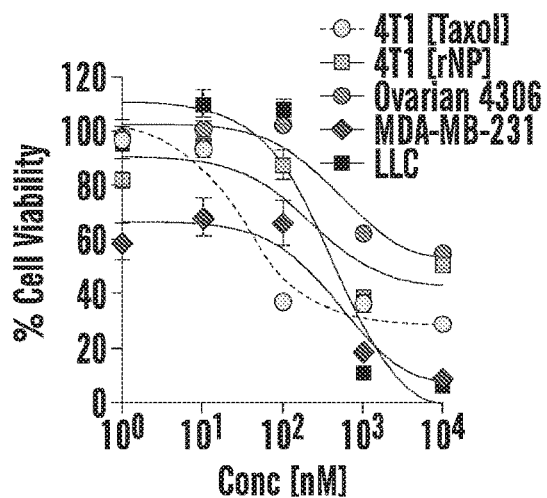
FIG. 3A is a graph showing the log concentration-effect of the BWHNP1 reporter nanoparticle on cell viability. Different cancer cells (breast—4T1, MDA-MB-231; Ovarian—4306; Lungs—Lewis Lung Carcinoma) were incubated with the reporter nanoparticle (at cytotoxic drug Paclitaxel-equivalent concentrations) for 48 h. Broken line represents a control group treated with paclitaxel. Cell lines exhibit different degrees of susceptibility to the reporter nanoparticle. Data is expressed relative to 100% viability in the absence of the reporter nanoparticle.
Figure 3B:
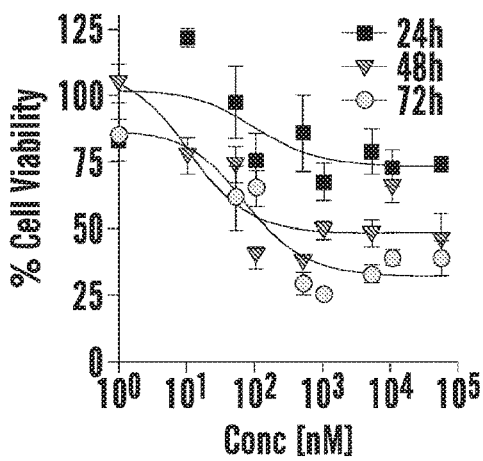
FIG. 3B is a graph showing the effect of treatment duration with reporter nanoparticles (20 µM paclitaxel-equivalent concentration) on the viability of 4T1 breast cancer cells. The shift in the concentration-response curves to the left with time is consistent to increased exposure to released drug over time.
Figure 3C:
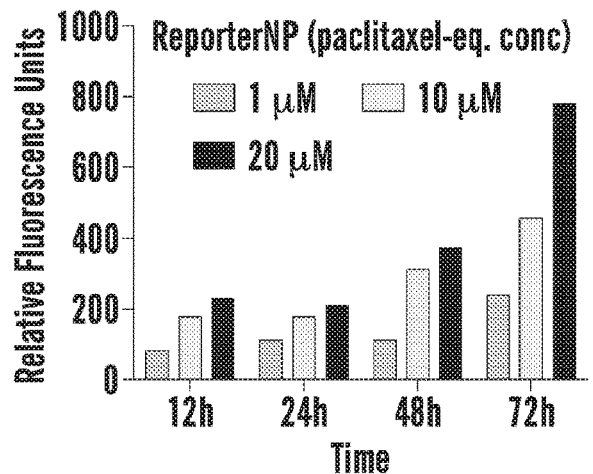
FIG. 3C is a graph showing the effect of increasing concentration of BWHNP1 reporter nanoparticle (cytotoxic drug Paclitaxel-molar equivalent) and exposure time on the increase in fluorescent intensity, consistent with reduction in cell viability.

The in vitro efficacy of BWHNP1 reporter nanoparticles was evaluated using multiple cancer cell lines, including breast (4T1 and MDA-MB-231), ovarian (4306) and lung (LLC). As shown in FIG. 3A, the BWHNP1 nanoparticles induced tumor cell kill across all the cell lines, with IC50 values ranging from 217.6±5.8 to 517.0±4.2 nM. While, the potency of BWHNP1 reporter nanoparticles at 48h post-incubation was lower compared to paclitaxel, an increase in potency, i.e. shift of concentration-response curve to the left, was observed with time, consistent with the temporal release of paclitaxel in the cells. To explore the possibility of using the reporter nanoparticles for temporal imaging of drug efficacy, cancer cells were incubated with different concentrations of BWHNP1 reporter nanoparticles and monitored the change in fluorescence intensity. As shown in FIG. 3C, a concentration- and time-dependent increase in the fluorescence signal was observed, which correlated with the reduction in cell viability.

Figure 4:
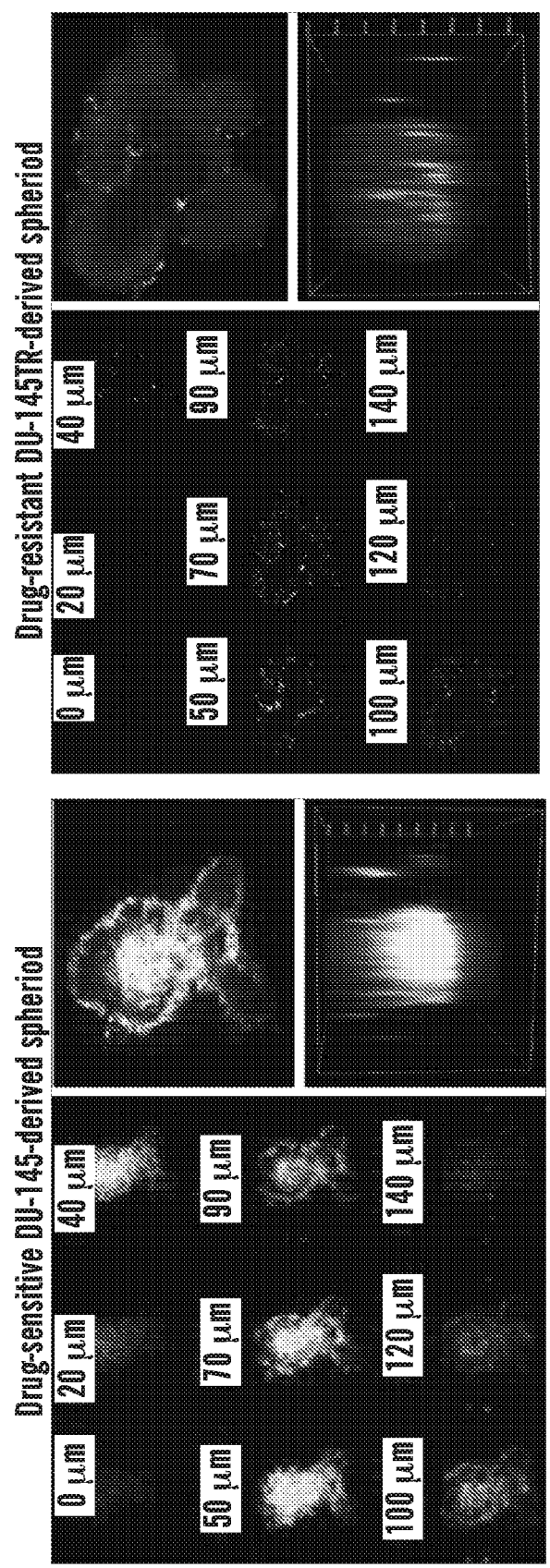
FIG. 4 is image showing the response in drug sensitive and drug resistant cells in vitro after treatment with BWHNP1 reporter nanoparticle. Paclitaxel-sensitive (DU-145) and -resistant (DU-145 TR) prostate cancer cells were allowed to form spheroids, which were incubated with reporter nanoparticles (equivalent to 20 µM paclitaxel) for 24h. The reporter nanoparticles used in this study were synthesized by using reporter element with FRET pair of 5-FAM as donor and QSY-7 as acceptor. The representative images were captured using confocal microscopy with Z-stack imaging at 10 µm intervals (all experiments were performed in triplicates). Scale bar represents 200 µm. Left panels show the signal from the reporter nanoparticles following Z-stack reconstruction of a DU-145 spheroid after treatment with reporter nanoparticles. Right panel shows Z-stack reconstruction of DU-145TR spheroid, highlighting the absence of signal from the reporter nanoparticles in the resistant cells.

Example 4: Monitoring the Response in Drug Sensitive and Drug Resistance Cells In Vitro by BWHNP1 Reporter Nanoparticles Recent studies have shown that in vitro 3D culture systems better mimic in vivo tumor microenvironment as compared to 2D monolayer cultures. Such systems model drug penetration and also conserve distinct signaling mechanisms that can influence the response to drug treatment (Nature Protocols, 2009, 4:309). Therefore, taxane-sensitive DU-145 and -resistant DU-145TR prostate cancer cells-derived 3D spheroids were treated with BWHNP1 reporter nanoparticles (at ~20 μM paclitaxel equivalent) for 24h. Z-stack reconstruction and images for DU145 spheroids showed activation of fluorescence signal even at a depth of 70 pm, indicating that the nanoparticles can penetrate into the core and induce cell death (FIG. 4). In contrast, minimal signal was observed from DU-145TR spheroids, indicating that the reporter nanoparticle could distinguish between sensitive and resistant tumors. The absence of any signal from the resistant spheroids further validated the absence of non-specific activation of the reporter element.

Example 5: NIR Dye Tagged BWHNP1 Show Higher Accumulation in Tumor

Figure 5:
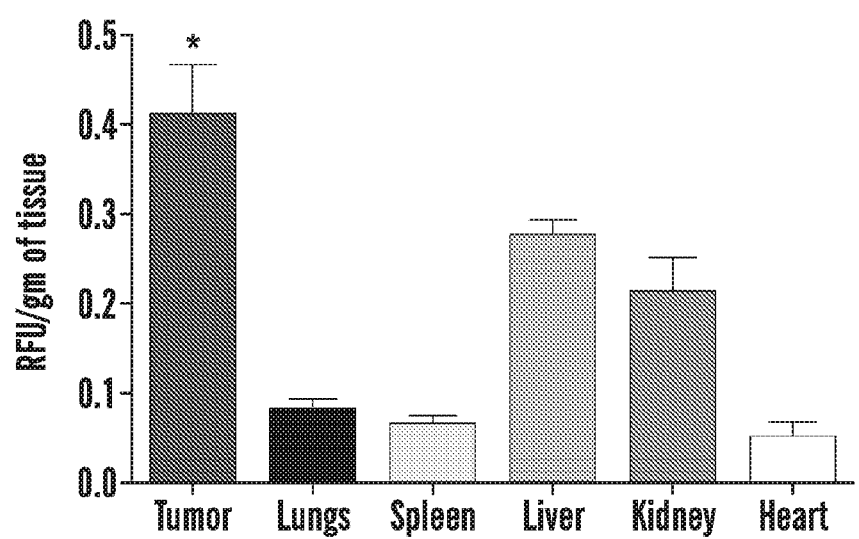
FIG. 5 is a graph quantitative analysis of reporter nanoparticles accumulation in different organs. Organs were excised from 4T1 tumor bearing mice 24h after tail vein injection of NIR dye-labeled BWHNP1 reporter nanoparticles. Images were captured at same resolution.

The biodistribution of the NIR dye tagged BWHNP1 reporter nanoparticles was studied in 4T1 tumor-bearing mice. As shown in FIG. 5, a preferential accumulation of the reporter nanoparticles in the tumor was observed, consistent with the notion that nanoparticles can home into tumors through an 'enhanced permeability and retention' (EPR) effect (Nature Reviews Drug Discovery, 2008, 7:771). Significant concentrations in the liver and the kidney were also observed, which could indicate clearance routes. It should be noted that the cut off for glomerular clearance of nanoparticles is ~5 nm (Nature Biotechnology, 2007, 25:1165), indicating that the reporter nanoparticles likely breakdown into smaller fractions in circulation. Interestingly, minimal accumulation in the major reticuloendothelial organs (RES), including lungs or spleen was observed, consistent with the large hydrodynamic radii as opposed to the actual electron microscopy measurements, which means that the nanoparticles are masked from the RES. This can increase the efficacy of reporter nanoparticle and also increases the detection sensitivity.

Figure 6A:
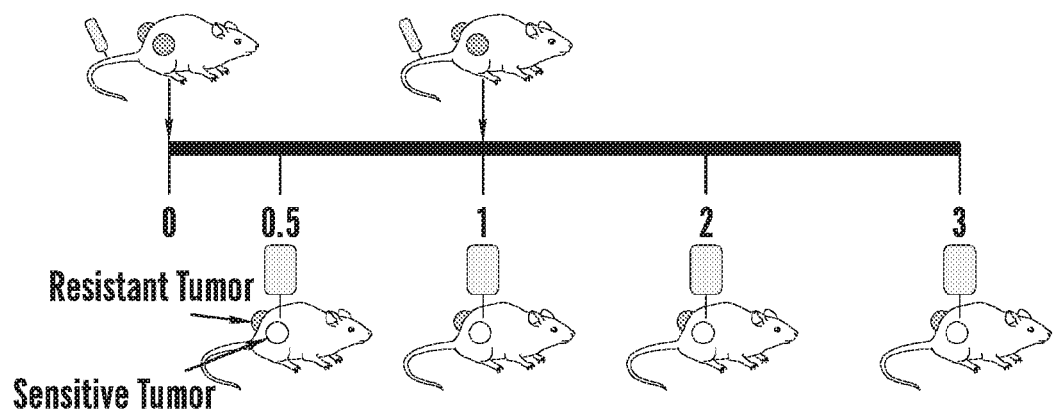
FIG. 6A is a schematic showing the experimental design. Paclitaxel-sensitive and -resistant tumors were inoculated in the right flank and left flank of the same mice. When the tumor volume reached ~500 mm$^3$, the animals were injected with two doses of reporter NPs (dose equivalent of 15 mg/kg paclitaxel). The live mice images were captured at different time points using a Maestro (CRI) in vivo fluorescence imaging system.
Figure 6B:
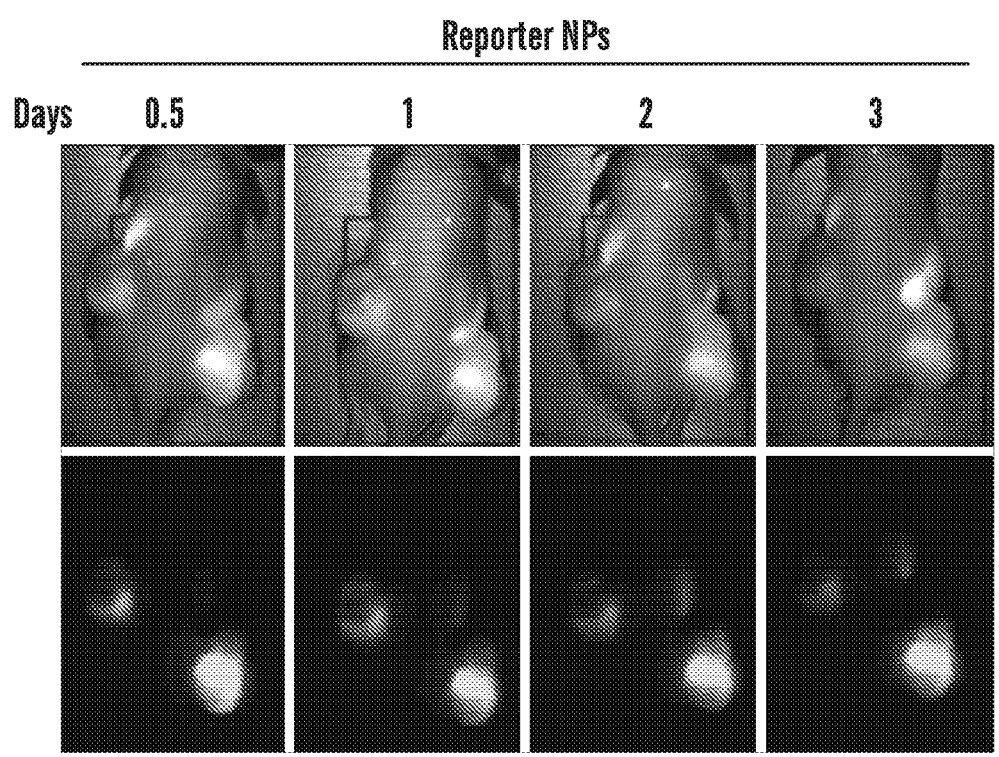
FIG. 6B is representative images showing sensitive (solid circle) and resistant tumors (dashed circle) from the treatment group at different time points.
Figure 6C:
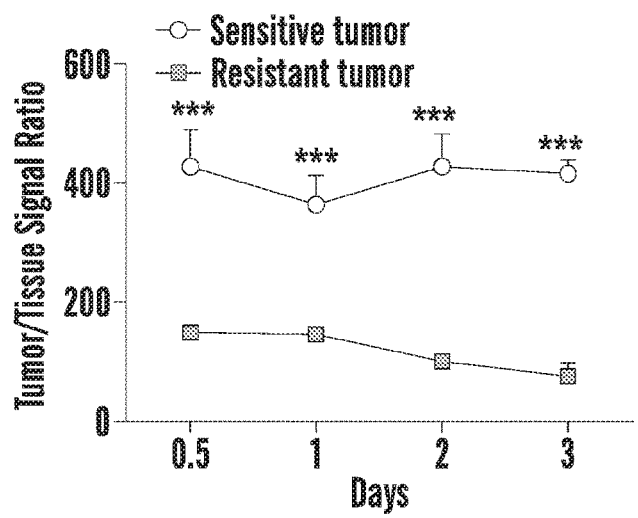
FIG. 6C is a graph showing the quantification of drug response to tumor as measured in terms of near infrared fluorescence intensity ratio between tumor and normal tissues at different time intervals. Data represents mean±SEM (n=3, *p<0.05; ***p<0.001 vs corresponding temporal value in resistant tumor, ANOVA followed by Bonferroni's post hoc test).
Figure 6D:
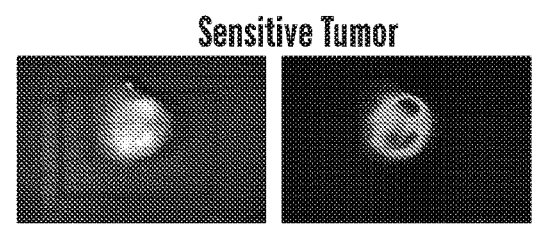
FIG. 6D is Ex vivo images of the excised tumors from the tumor bearing mice after the treatments using pseudocolor to show fluorescence emission.
Figure 6D:
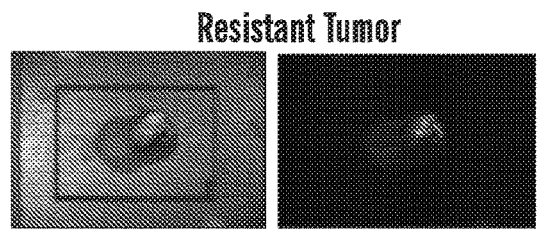
Figure 6E:
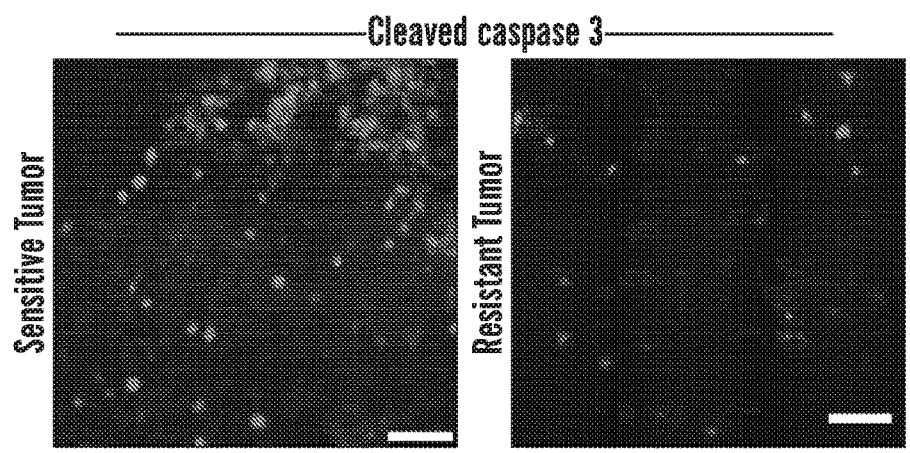
FIG. 6E shows representative fluorescence images of the sections from reporter NP-treated taxane-sensitive and taxane-resistant tumors stained with a cleaved caspase-3 antibody.

Example 6: Real Time Imaging of Drug Efficacy and Drug Resistance in In Vivo DU145 and DU-145TR Dual Prostate Cancer BALB/c Nude Mice Model In order to test if reporter nanoparticles BWHNP1 could be used to distinguish between drug-sensitive and drug-resistant tumors in mice early on during chemotherapy, a dual human tumor xenograft model was used, where paclitaxel-sensitive (DU-145) and paclitaxel-resistant (DU-145TR) prostate cancer cells were implanted in the either flanks of the same mouse, respectively. The animals were injected with two doses of reporter NPs (dose equivalent to 15 mg/kg of paclitaxel) via the tail vein and imaged as previously described (FIG. 6A). As shown in FIGS. 6B-6D, the sensitive tumor showed ~400 percent increase in fluorescence activation as compared to resistant tumor, which was detected as early as 12h after the first treatment. Furthermore, immunolabeling the tumor sections for cleaved caspase-3 confirmed that the mechanism of action of the reporter nanoparticle efficacy and fluorescent signal in sensitive tumor is due to drug-mediated caspase activation.

Example 7: Synthesis of PD-L1 Reporter Nanoparticles

Figure 7:
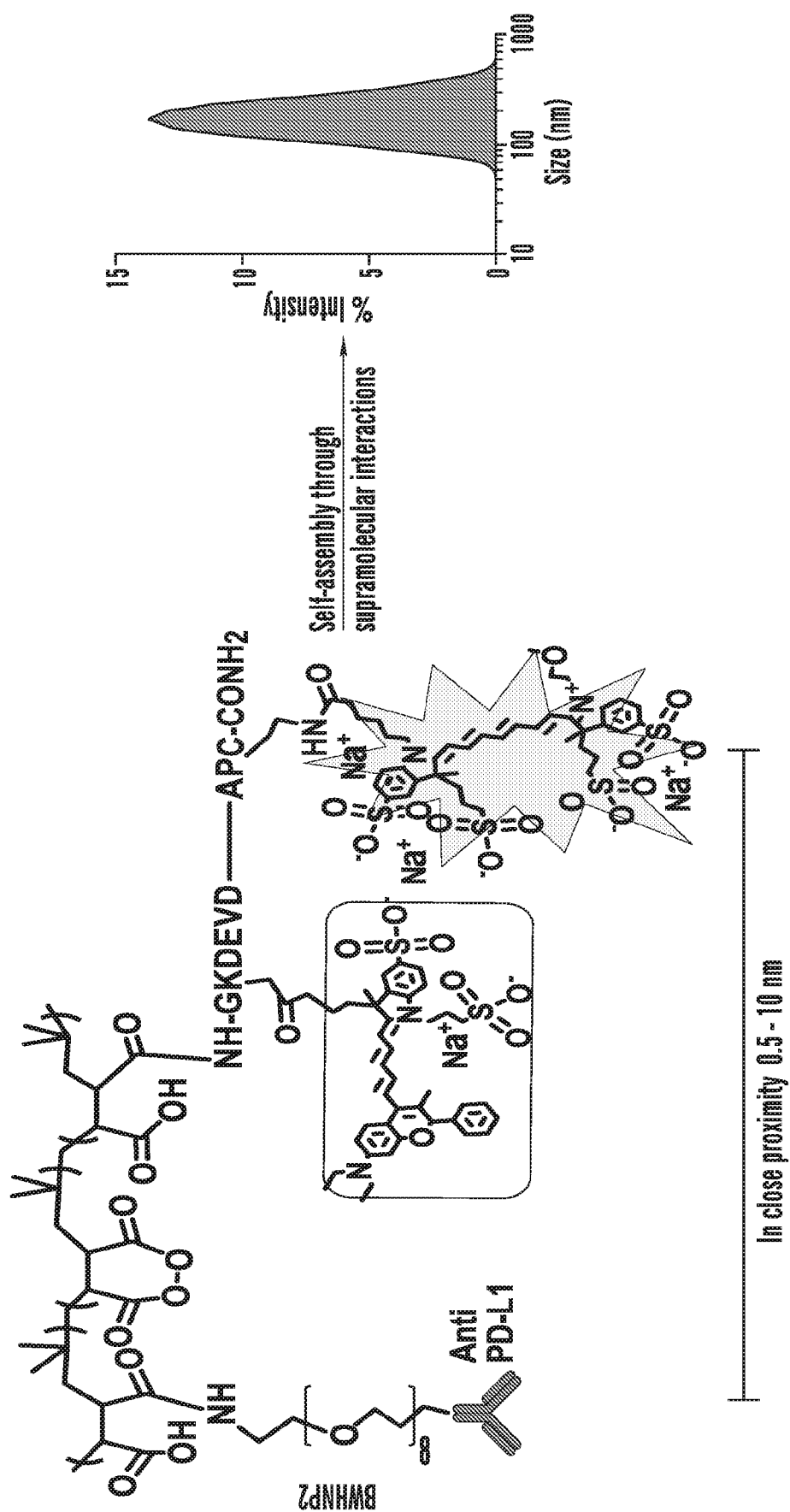
FIG. 7 is a schematic showing the synthesis of PD-L1 reporter NPs. The reporter NPs were synthesized by conjugating Carboxy-(PEG)$_8$-amine and reporter element in optimized ratio to PIMA polymer followed by self-assembly in water. Then, PD-L1 antibody or control IgG antibody is conjugated to NPs using EDC-NHS conjugation chemistry. The size distribution of PD-L1 reporter NPs is shown as DLS graphs.

Next, it was studied whether the reporter material can be adapted to immunotherapy. To engineer a reporter material that can act as an immune checkpoint inhibitor, PIMA was first derivatized with different ratio of carboxy-PEG$_8$. At an optimal ratio of 1:10, i.e. 10 PEG$_8$s per molecule of PIMA, self assembly of the material into defined nanoparticles with a hydrodynamic diameter of 231+22 nm was observed, while higher or lower ratio resulted in particles of larger size. Using the 10:1 PEG to polymer ratio, the reporter element was conjugated to PIMA, such that the ratio of PIMA:PEG$_8$: Reporter element was 1:9:1. The antibody against PD-L1 was then conjugated to the PEG resulting in supramolecular self-assembly to reporter nanoparticles (BWHNP2) that had a hydrodynamic diameter of 242±37 nm (FIG. 7). A control IgG-conjugated reporter nanoparticle was similarly engineered, and was found to be similar in dimension as the anti-PD-L1-reporter nanoparticle.

Example 8: Binding of the Antibody to PD-L1

Figure 8B:
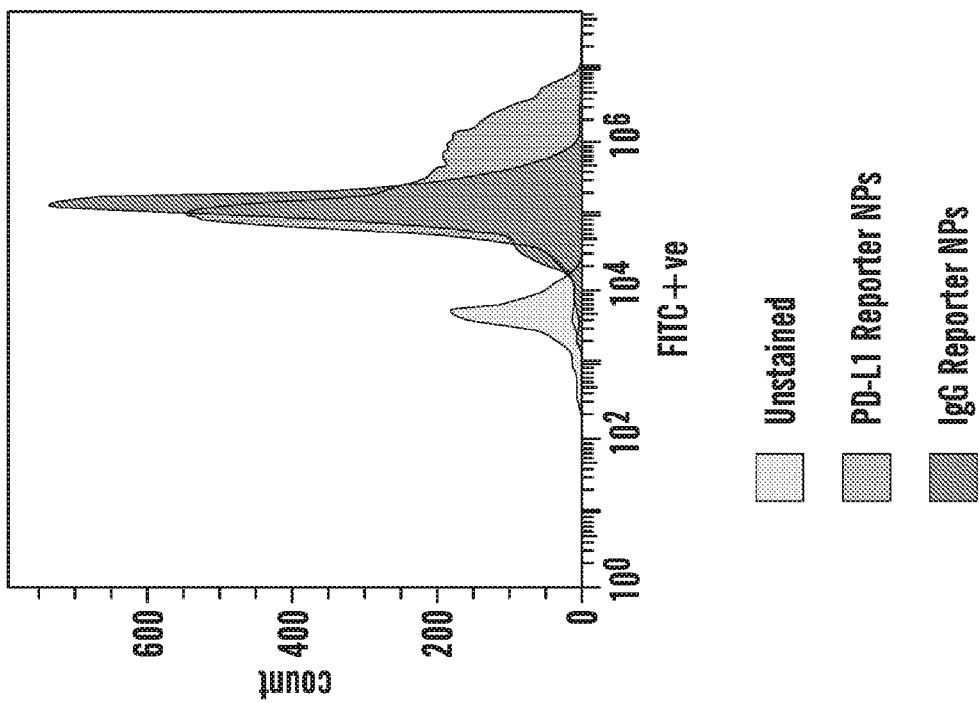
FIG. 8B is FACS data showing internalization of PD-L1 reporter NPs in PD-L1 overexpressing B16/F10 melanoma cells as compared to control IgG-reporter NPs.
Figure 8A:
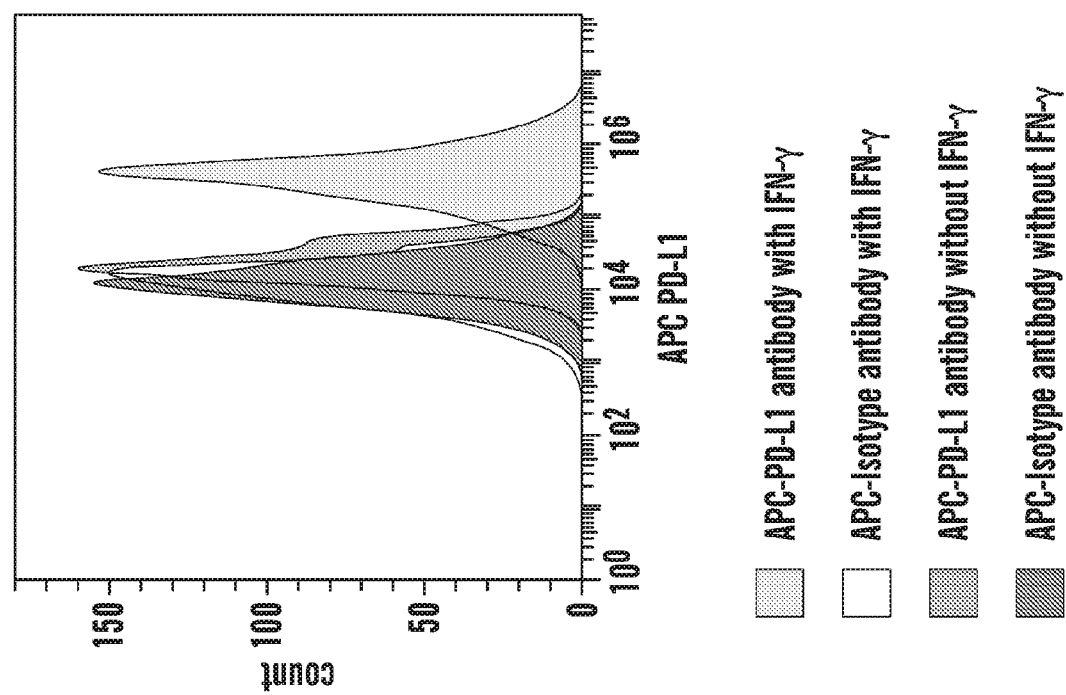
FIG. 8A is FACS analysis showing expression of PD-L1 on B16/F10 melanoma cells after treatment with IFN-γ.

To test whether the bioconjugation conserves the binding of the antibody to PD-L1, the B16/F10 melanoma cells were first treated with IFNγ for 24 h, which resulted in an over-expression of PD-L1 compared with controls, as quantified using flow cytometry (FIG. 8A). These cells were then incubated with FAM-labeled reporter nanoparticles conjugated with either anti-PD-L1 antibody or control IgG. As shown in FIG. 8B, the anti-PD-L1-reporter nanoparticle was found to bind to the cells to a greater degree as compared with the controls.

Figure 9A:
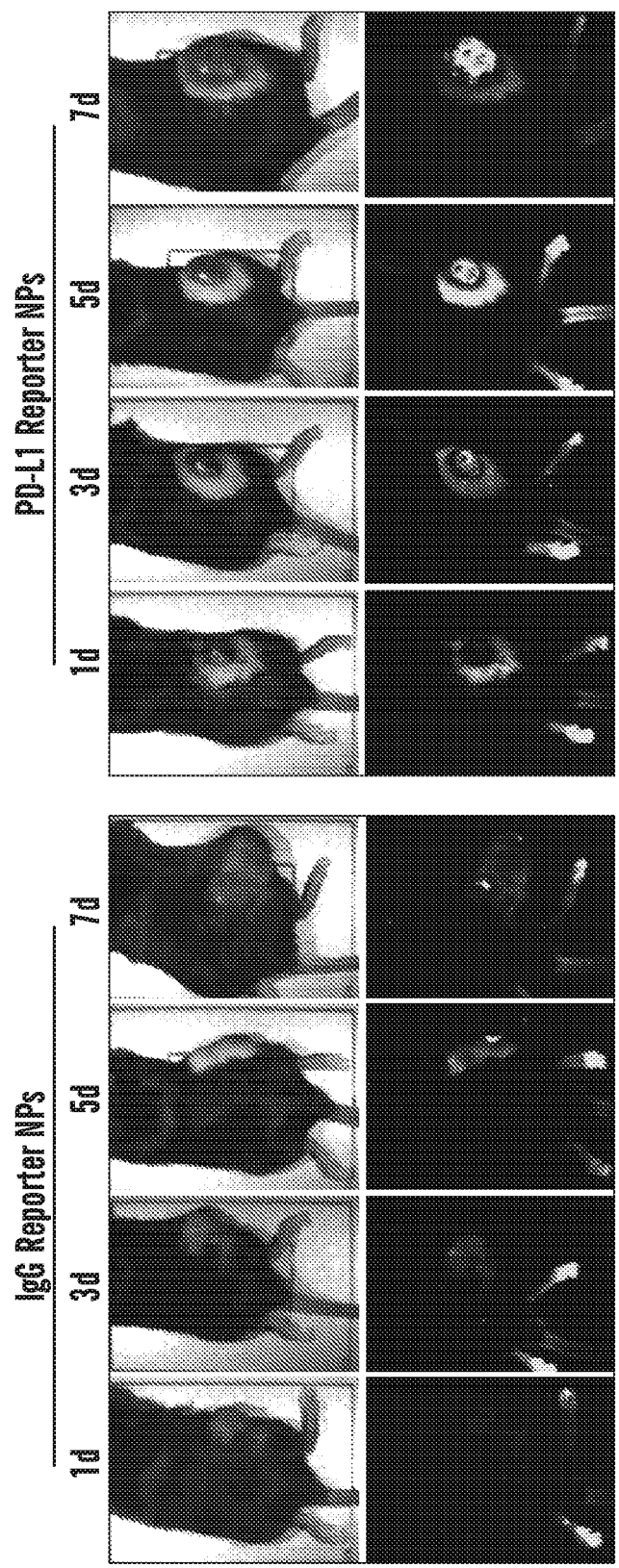
FIG. 9A is representative images of IgG-reporter NPs and PD-L1 reporter NPs treated groups at different days after the initial treatment. The treatments were administered when the tumor volume reached ~100 mm$^3$ and live mice images were captured using a Maestro (CRI) in vivo fluorescence imaging system.
Figure 9B:
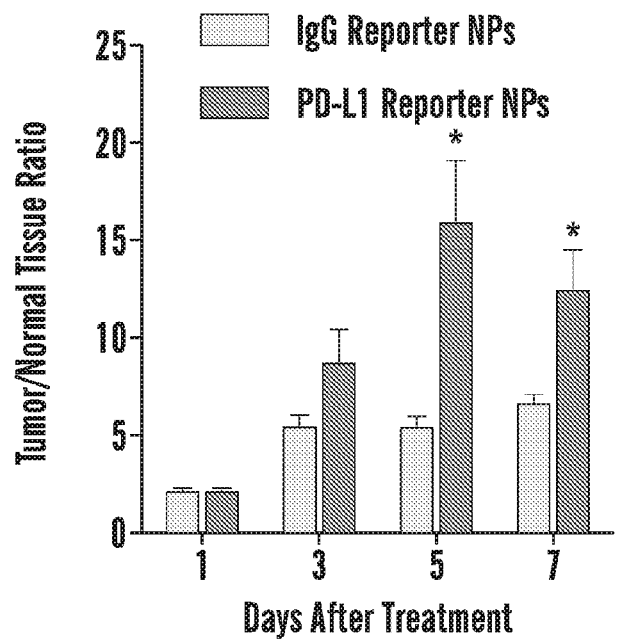
FIG. 9B is a graph showing the quantification of immunotherapy response to tumor as measured in terms of near infrared fluorescence intensity ratio between tumor and normal tissues at different days after the treatment. Data represents mean±SEM (n=3, *p<0.05 vs corresponding temporal value in IgG-reporter NPs groups, ANOVA followed by Bonferroni's post hoc test).
Figure 9C:
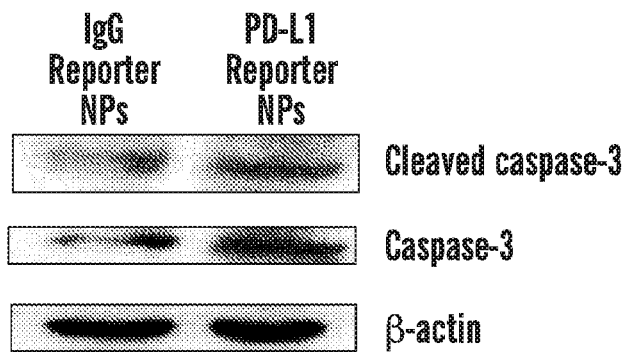
FIG. 9C is western blot analysis showing expressions of caspase-3 and cleaved caspase-3 in tumors treated with different Reporter NPs.
Figure 9D:
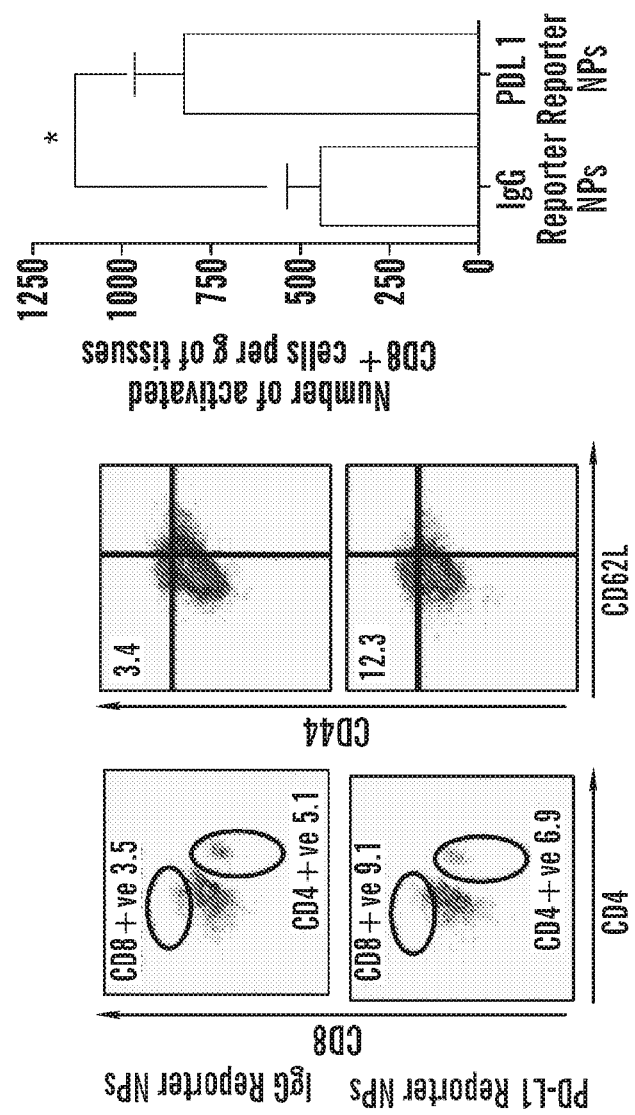
FIG. 9D is representative FACS data from the B16/F10 tumor-bearing mice after different treatments. The left panel shows percentage of CD8+ vs CD4+ T cells in the isolated lymphocyte population. The right panel shows the percentage of activated CD8+ T cells (CD44+CD62L–). The graph shows quantification of number of activated CD8+ T cells per gram of tumor in different treatments. Data represents mean±SEM (n=3, *p<0.05 vs corresponding value in IgG-reporter NPs groups, statistics was performed using student's t-test).
Figure 9E:
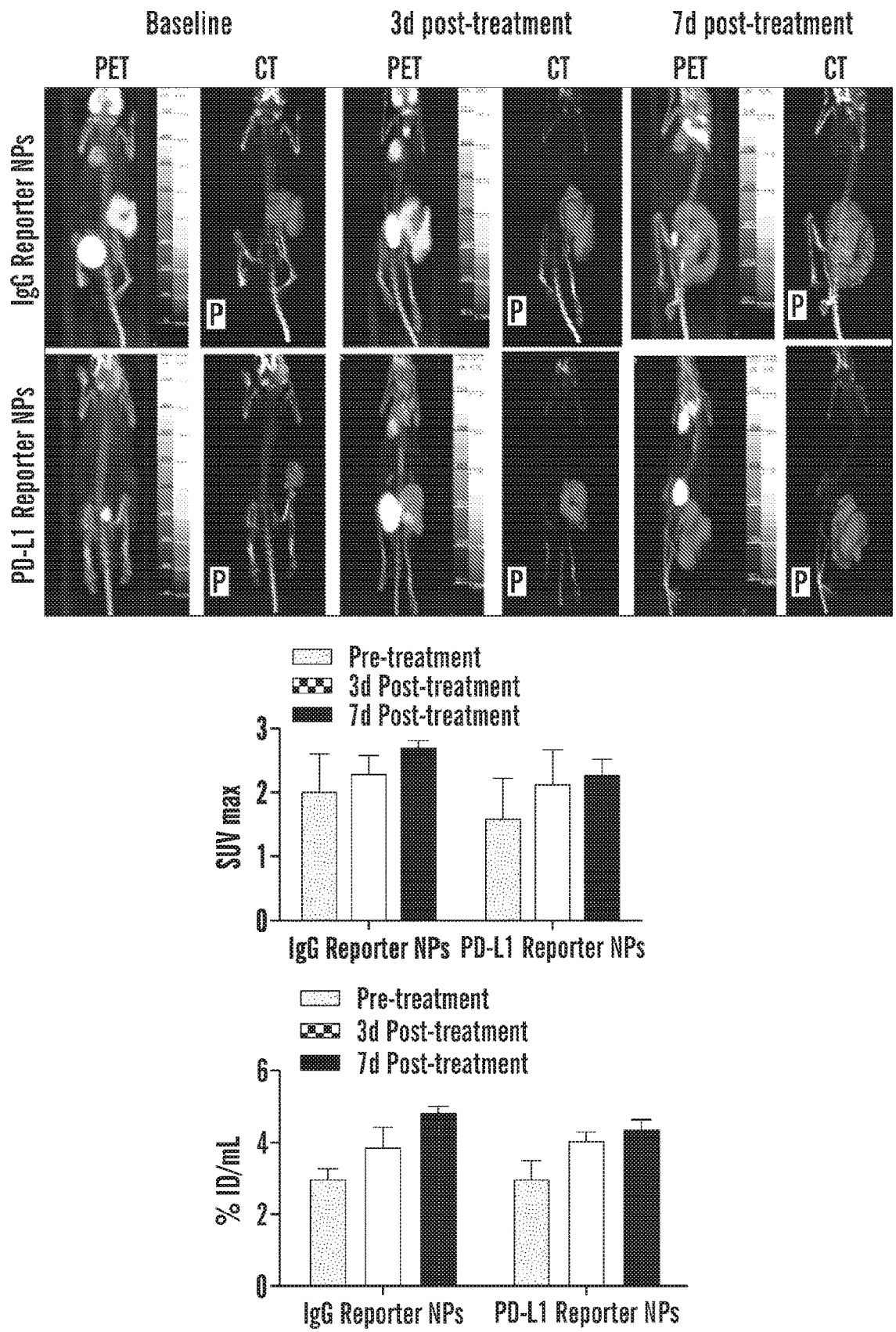
FIG. 9E shows [$^{18}$F]FDG PET and CT images of representative animals in IgG reporter NPs- and PD-L1 reporter NPs-treated groups before, 3 and 7 days after the treatment. B16/F10 melanoma tumor-bearing mice were treated with IgG reporter NPs or PD-L1 reporter NPs. Graphs show SUV max and % ID/mL for different treatment groups from the above study.

Example 9: Reporter Nanoparticles Enable Imaging of Immunotherapy Response in a B16/F10 Melanoma Mouse Model It was tested whether the anti-PD-L1 reporter nanoparticles BWHNP2 enabled the monitoring of drug response in real time in vivo. The reporter nanoparticles were injected in a B16/F10 melanoma bearing mice and the response was monitored over different times. As shown in FIGS. 9A and 9B, as compared with the IgG-control reporter nanoparticles, a significant increase in the fluorescent signal was observed by Day 5 in the anti-PD-L1 reporter nanoparticles-treated group. This is consistent with the indirect mechanisms of induction of cell death following treatment with an immune checkpoint inhibitor. Indeed, western blotting revealed an increased caspase activation in the cells isolated from the anti-PD-L1 reporter nanoparticles-treated tumor as opposed to the control group (FIG. 9C). Furthermore, quantifying $CD44^{Hi}$ $CD62L^{Lo}$ CD8+ve cells in the tumor revealed that the treatment with anti-PD-L1 reporter nanoparticles indeed enhanced activated T cell infiltration by ~200% as compared with IgG-reporter nanoparticles (FIG. 9D). Currently, response monitoring for immunotherapy treatments is performed using FDG-PET. It was further investigated if [$^{18}$F] FDG-PET or CT imaging could similarly detect the early treatment response as achieved using the reporter nanoparticles. However, no reduction in the standard uptake value (SUV) or [$^{18}$F]FDG uptake in tumor was observed even at 7 days post-treatment between control nanoparticles and reporter nanoparticles-treated groups. This shows that reporter nanoparticles can monitor the immunotherapy response early where current imaging techniques lack the sensitivity.

Example 10: MRI Activatable Reporter Materials

Figure 10:
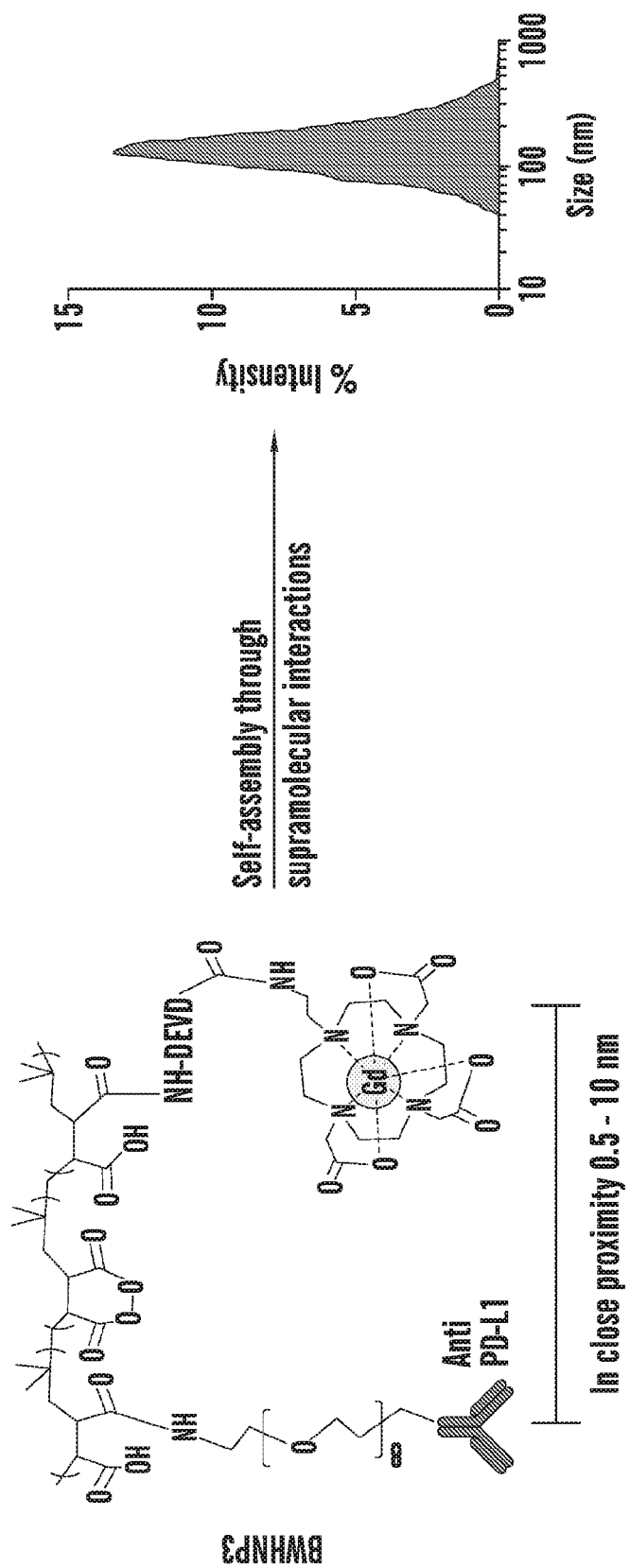
FIG. 10 is a schematic showing synthesis of reporter nanoparticle with immunotherapy drug and caspase activatable MRI-based reporter element conjugated to PIMA polymer. At the optimal drug to reporter element ratio, this polymer self-assembles into a nanoparticle of ~100 nm size. The size distribution is shown as DLS graph.

Design of clinically relevant MRI activatable reporter materials was then investigated. Design of MRI-activatable probes is chosen, since it provides high spatial resolution, the best soft-tissue contrast, low toxicity and the absence of ionizing radiations. A paramagnetic gadolinium ($Gd^{3+}$) based contrast agent is used, since it exhibits positive (bright) contrast which is more preferable for activatable systems compared to the agents that provide negative contrast (dark). A reporter element was synthesized by conjugating Gadolinium-DOTA cage to DEVD peptide (FIG. 10). Conjugation of MRI-based reporter element and immunotherapy drug to PIMA polymer results in self-assembled MRI-responsive reporter nanoparticles (BWHNP3). The conjugation includes immune checkpoint inhibitor PD-L1 antibody and MRI activatable reporter element to PIMA polymer. It was anticipated that Gd-based contrast agent conjugated to caspase-responsive peptide would change it's relaxivity significantly in response to peptide cleavage by caspase enzyme thereby enabling real-time imaging of immune therapy response. The size distribution of the reporter nanoparticle is shown as Dynamic Light Scattering (DLS) graph.

Figure 11:
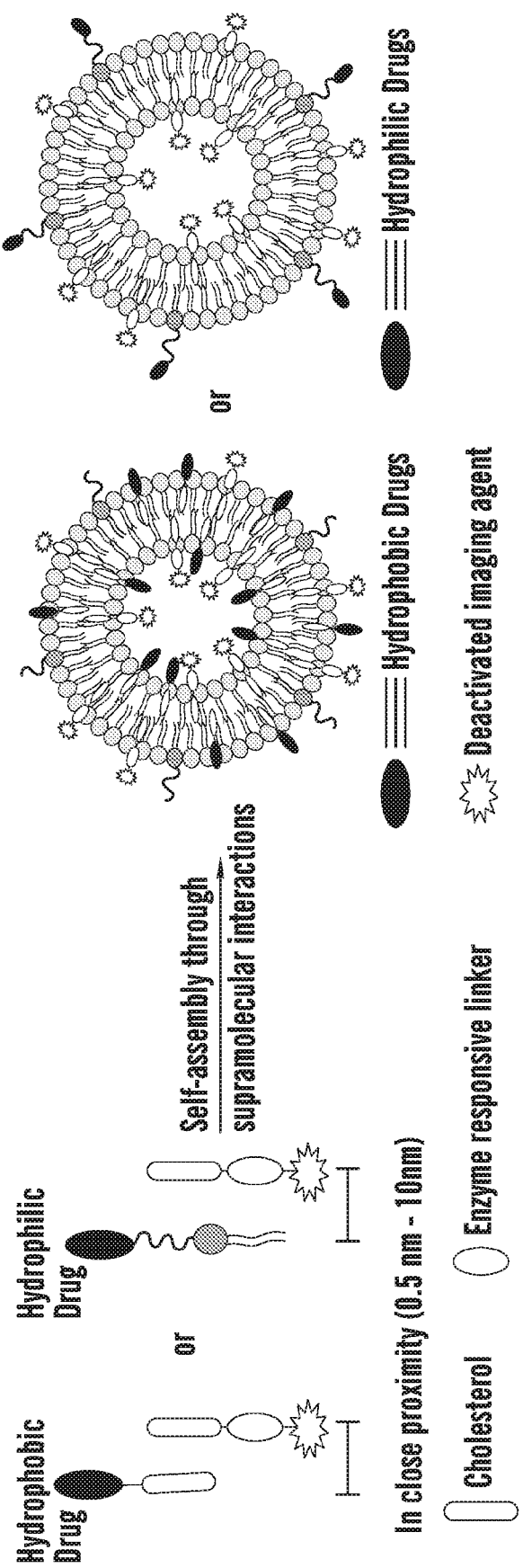
FIG. 11 is a schematic showing the synthesis of self-assembling reporter materials facilitated by co-lipids. The hydrophobic drugs can be conjugated to lipids including cholesterol and hydrophilic drugs such as antibodies, peptides can be conjugated to DSPE-PEG. The activatable reporter element comprises of an imaging agent conjugated to cholesterol or lipids through enzyme responsive linker.

Example 11: Synthesis of Self-Assembling Reporter Materials Facilitated by Co-Lipids The possibility of adapting the reporter platform to FDA approved components that are biodegradable and biocompatible was then explored. The self-assembling reporter materials was engineered from amphiphilic, biodegradable and biocompatible components including lipid-drug conjugate, Phosphaidylcholine (PC) and 1,2 distearoyl-sn-glycero-3-phospho-ethanolamine-N-[amino (polyethylene glycol)-2000] (DSPE-PEG) which will ensure the close proximity of drug and activatable reporter element in the reporter nanoparticle (FIG. 11). Cholesterol-drug conjugates were used for hydrophobic drugs and DSPE-PEG-drug conjugates were used for hydrophilic drugs. The rationale for choosing cholesterol, PC and DSPE-PEG as the building blocks for the nanomaterials are, (i) cholesterol and PC are components of biological cellular membranes, as a result they are biodegradable, non-toxic, and approved by FDA, (ii) the 3β-OH groups of cholesterol are easily amenable to conjugation with drugs of choice to improve their pharmacodynamic/pharmacokinetic profile as well as cellular uptake, (iii) all reagents used in the study are commercially available in high purity and allows easy scale up for IND enabling studies, (iv) cholesterol, PC and DSPE-PEG self-assemble into novel structures as a result of hydrophilic-hydrophobic interactions, and (v) DSPE-PEG inducts "stealth" property in materials by decreasing surface interaction with opsonin and thereby reduces clearance by the reticuloendothelial system. Activated imaging agent is conjugated to cholesterol through an enzyme responsive linker. The self-assembly can be achieved by using lipid-film hydration method. Further, the 'plug and play' nature of the self-assembly offers flexibility and compatibility to encapsulate multiple agents with diverse physicochemical properties in desired ratios to engineer multimodality materials.

Figure 12:
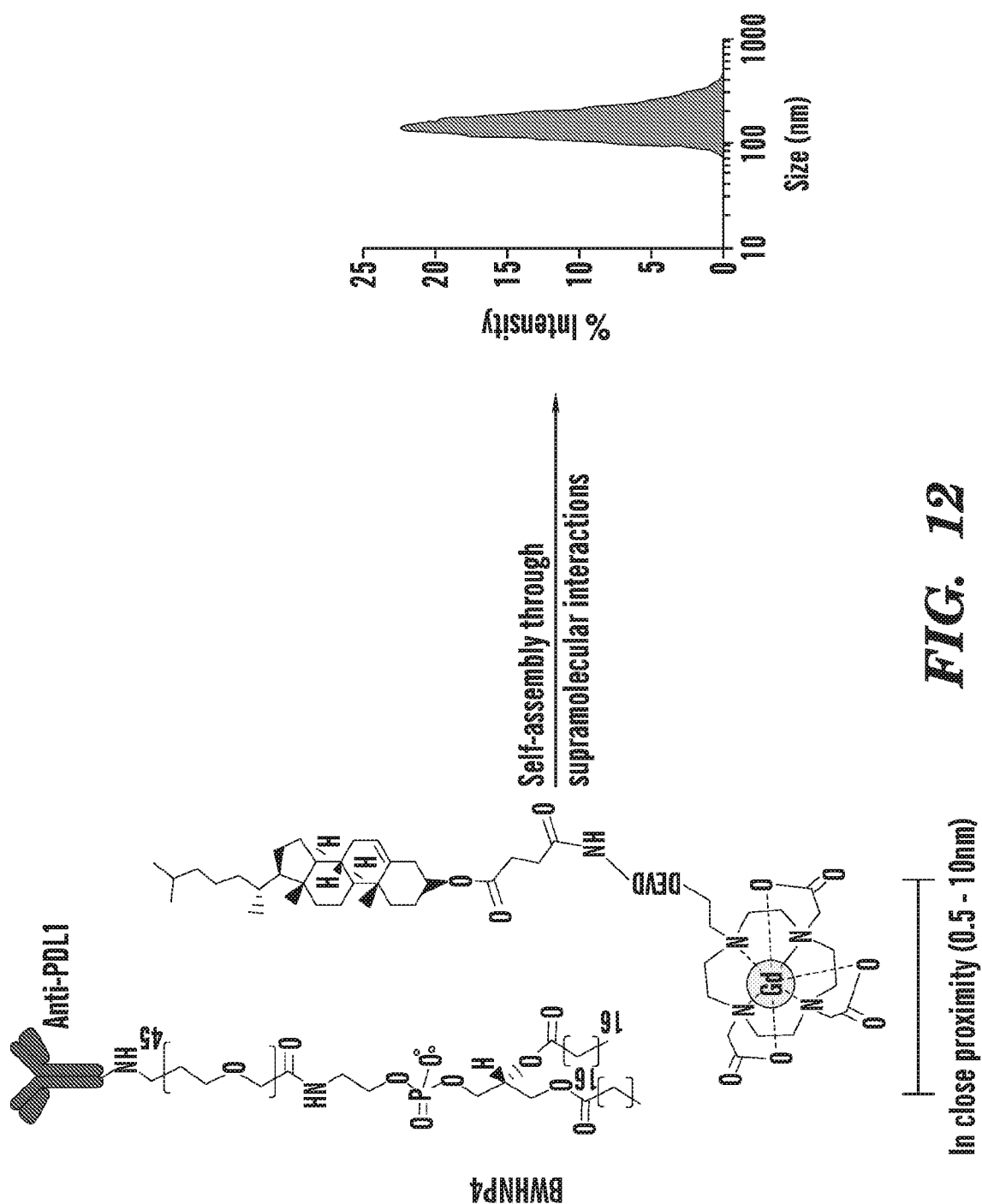
FIG. 12 is a schematic showing the synthesis of lipid based reporter material with immunotherapy drug and MRI activatable imaging agent. The self-assembly results in nanostructures of ~200 nm size as measured by DLS.

Example 12: Synthesis of Lipid Based Reporter Material with Immunotherapy Drug and MRI Activatable Imaging Agent The self-assembly of lipid-immunotherapy drug conjugate (DSPE-PEG conjugated to anti-PDL1 antibody) and reporter element with PC as co-lipid resulted in a nanosize material (BWHNP4). The reporter element is synthesized by first conjugating gadolinium-DOTA cage to DEVD peptide which is then conjugated to cholesterol (FIG. 12). The self-assembly results in reporter nanoparticles of ~200 nm size as shown in DLS graph.

Figure 13:
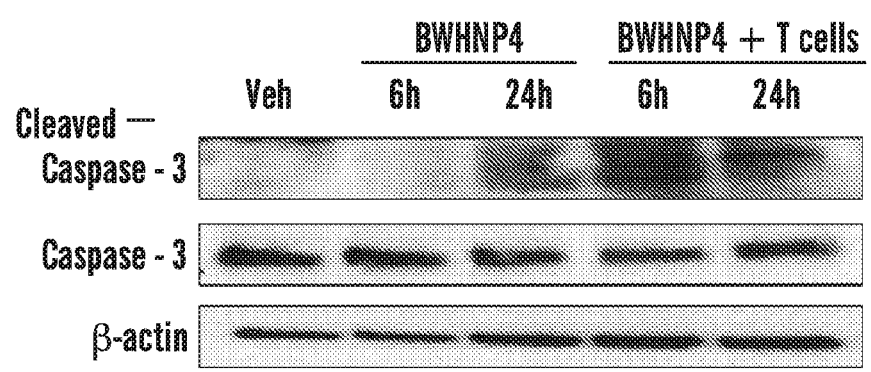
FIG. 13 is western blot analysis showing higher expression of cleaved caspase-3 in B16F10 melanoma cells after treatment with BWHNP4 in T cell—cancer cells co-culture model.
Figure 14:
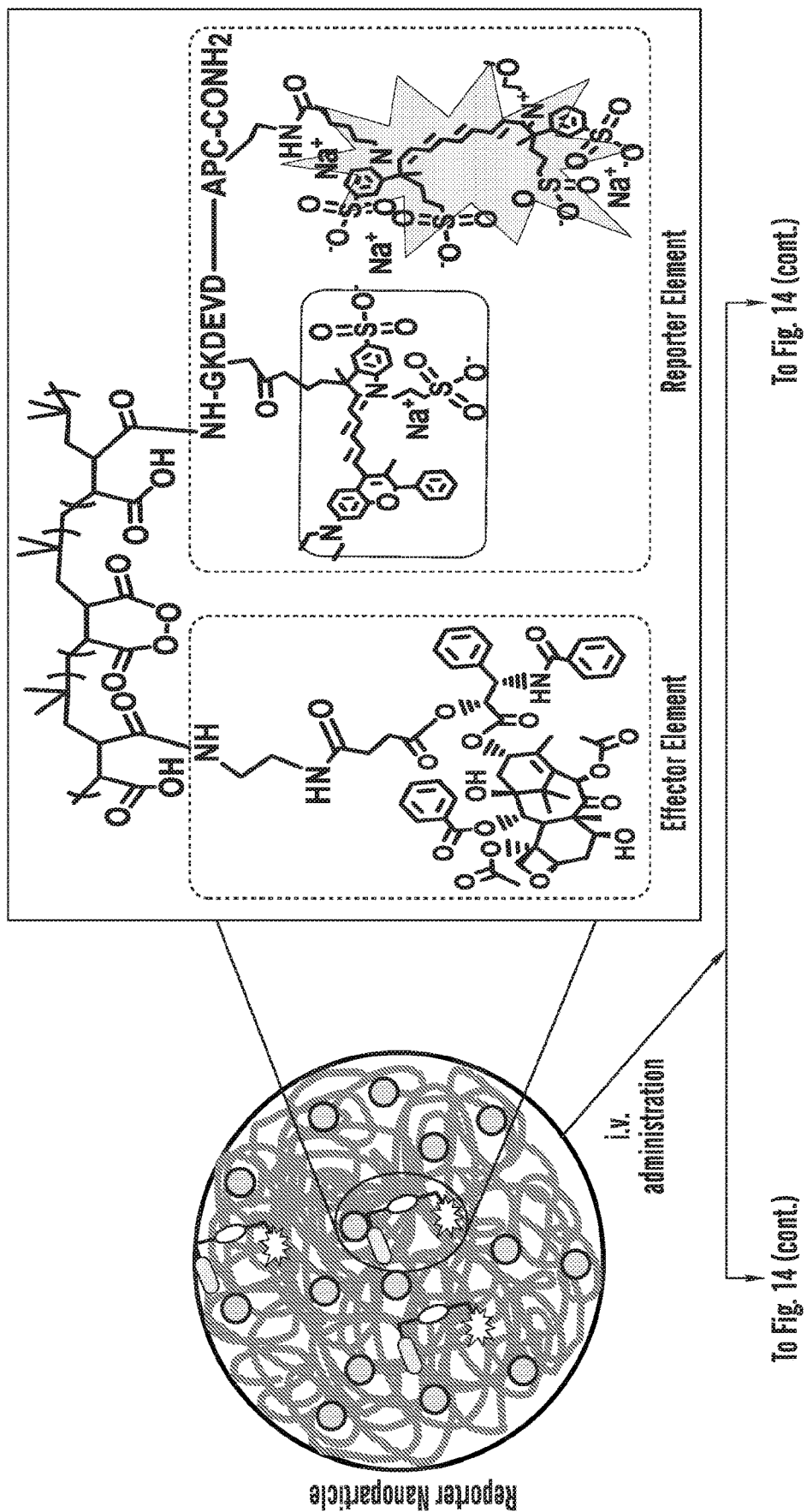
FIG. 14 is a schematic showing construct of a reporter nanoparticle. The reporter nanoparticle comprises three components: a polymeric back-bone, an esterase-cleavable prodrug synthesized from an anticancer drug (effector element (EE)), and an activatable reporter element (RE). At the optimal ratio of EE:RE, this stimuli-responsive polymer self-assembles into a nanoparticle. In normal condition, the fluorescent signal from the reporter element is in the off state because the drug is intact inside the nanoparticle. In a drug-sensitive cell (lower right of the schematic), the released drug initiates apoptosis via the activation of caspase-3 enzyme, which then cleaves the DEVD peptide, unquenching the fluorescent signal (on state). However, in a nonresponder cell (lower left of the schematic), the failure of the released drug to induce apoptosis means the reporter element remains in the off state. The distinction between off and on states allows the visualization of a nanoparticle in action.
Figure 14:
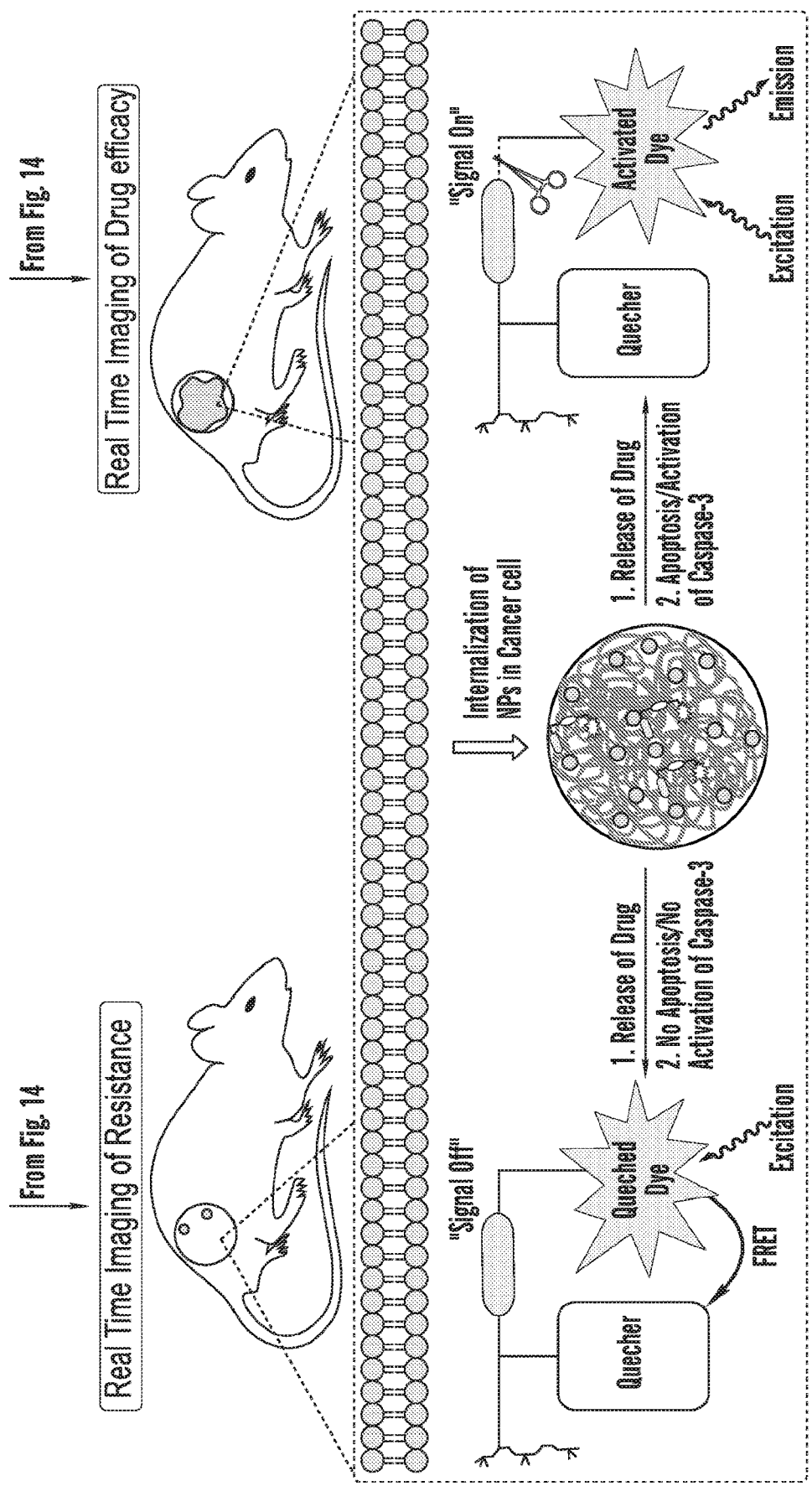
Figure 15E:
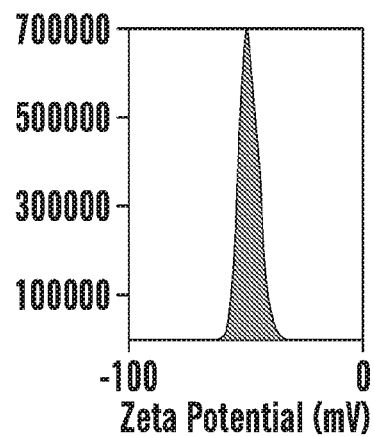
FIG. 15E is a graph showing zeta potential of the reporter nanoparticle at pH 7.
Figure 15F:
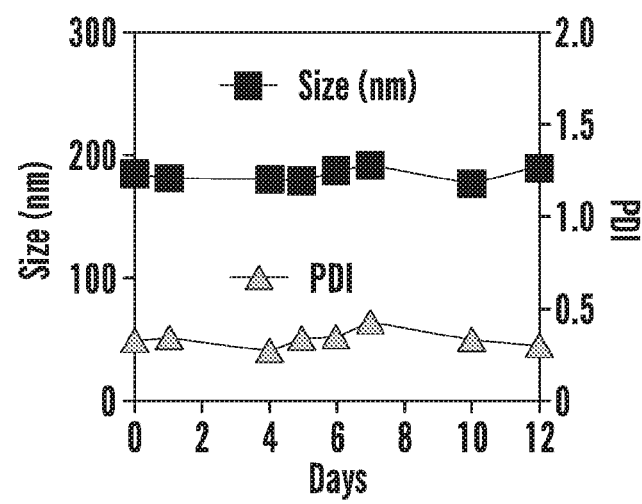
FIG. 15F is a graph showing the changes in size and polydispersity index (PDI) of the nanoparticles over time during storage at 4 C as a measure of stability.
Figure 15G:
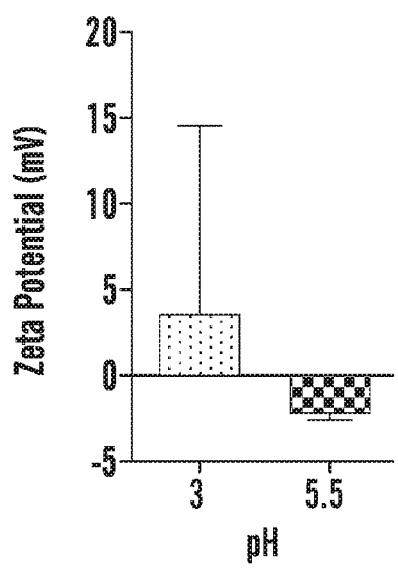
FIG. 15G is a graph showing effect of pH on zeta potential of reporter nanoparticles.
Figure 15H:
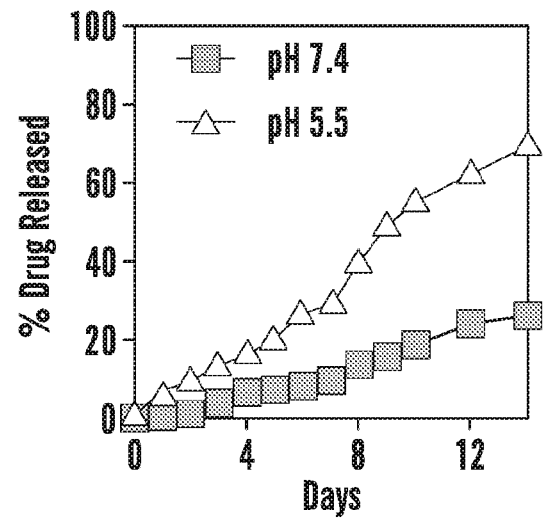
FIG. 15H is a graph showing the release kinetics profiles of paclitaxel from the nanoparticles when incubated at either pH 7.4 or 5.5. All experiments were performed in at least triplicate.
Figure 16:
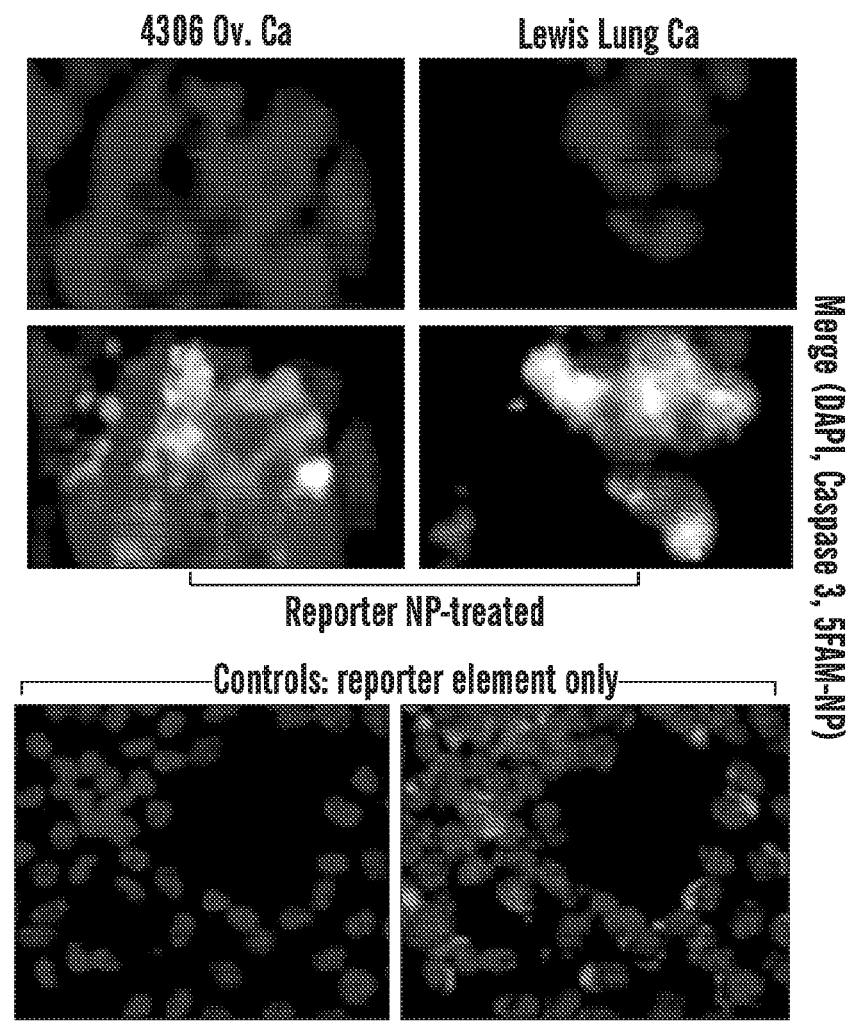
FIG. 16 is a representative image showing that reporter nanoparticles read out caspase-3-mediated apoptosis. The 4306 ovarian cancer cells and Lewis lung carcinoma cells were incubated with FAM5-QSY7-based reporter nanoparticles. Cleaved caspase-3 was immunolabeled with rabbit mAb antibody followed by anti-rabbit Alexa Fluor 594 antibody and overlays with the activated 5-FAM signal (Upper). Incubating the cancer cells with a control nanoparticle with reporter element alone shows that in absence of the effector element, no FAM5 fluorescent signal is evident, and serves as controls for nonspecific activation of reporter signal (Lower).
Figure 17A:
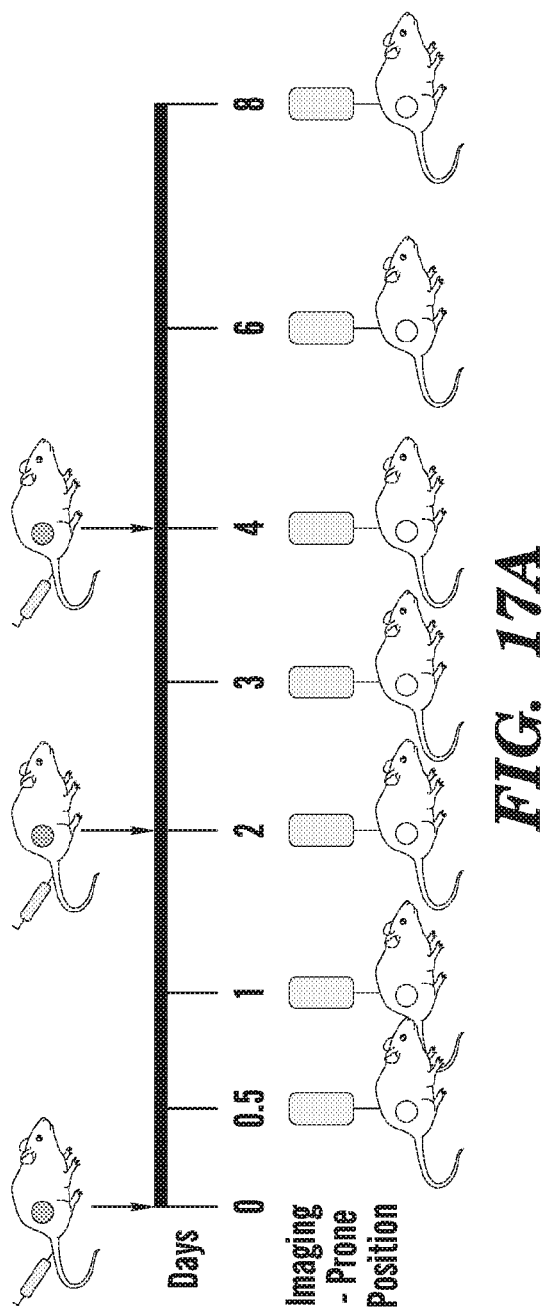
FIG. 17A is a schematic showing reporter nanoparticle treatment and imaging schedule. The 4T1 breast cancer-bearing animals were injected with control nanoparticles (NPs) or reporter NPs. The control NPs were synthesized by conjugation of reporter element to the polymer backbone without paclitaxel-based effector element. When the tumor volume reached 500 mm$^3$, the animals were injected with three doses of control NPs or reporter NPs (dose equivalent to 15 mg/kg paclitaxel) every alternate day (days 0, 2, and 4). The reporter element concentrations in both control NPs and reporter NPs were kept constant. The live mice imaging was done at different time points using a Maestro (CRI) in vivo fluorescence imaging system.
Figure 17B:
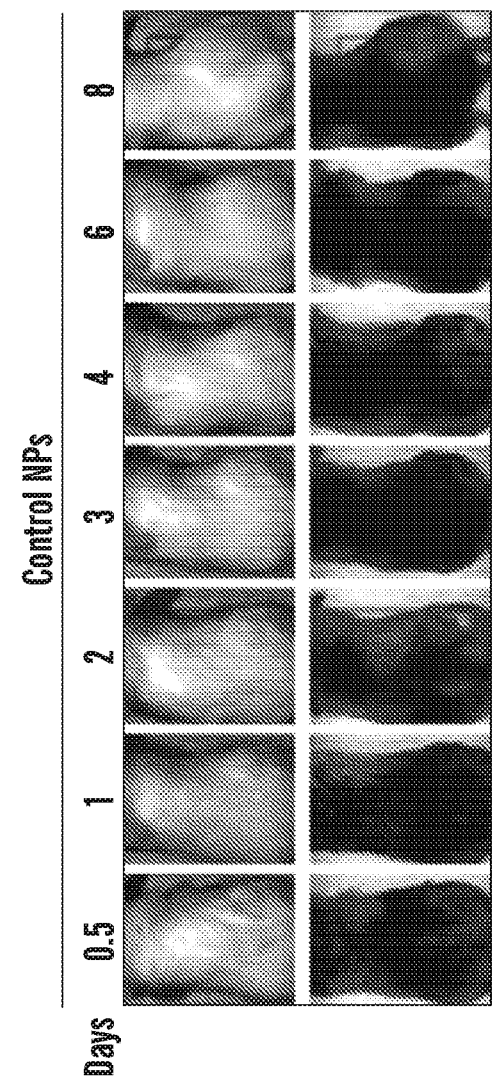
FIG. 17B is a representative image showing control NP-treated groups at different time points.
Figure 17F:
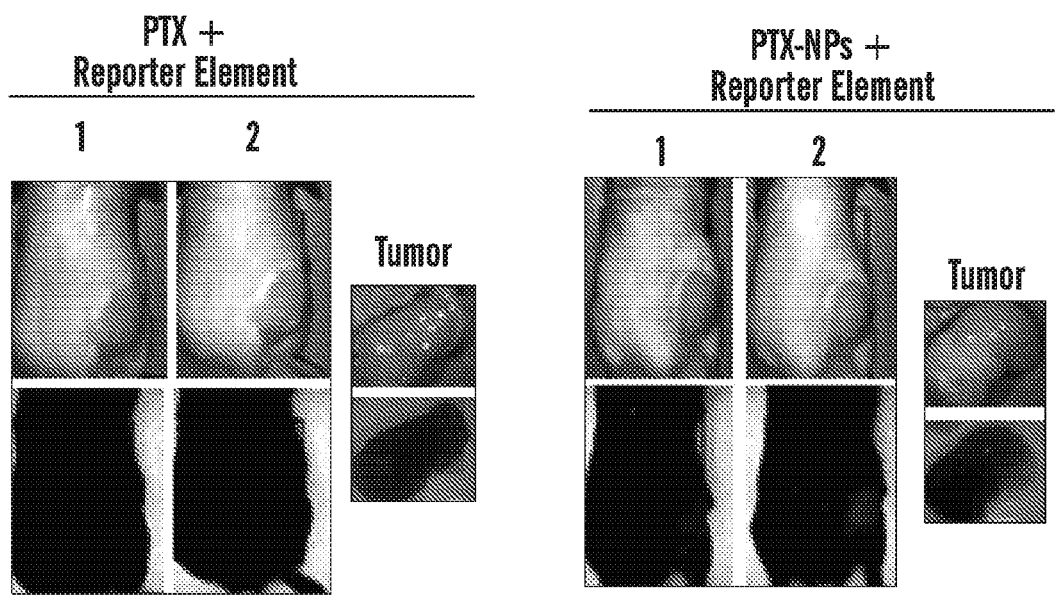
FIG. 17F is a representative image showing tumor-bearing mice imaged at 24 and 48 h after treatment with a combination of either paclitaxel (PTX)+ reporter element or PTX-NP+ reporter element. Side panels show ex vivo images of the tumor from the tumor bearing mice after the treatments. Lower panels capture fluorescent emission images.
Figure 17G:
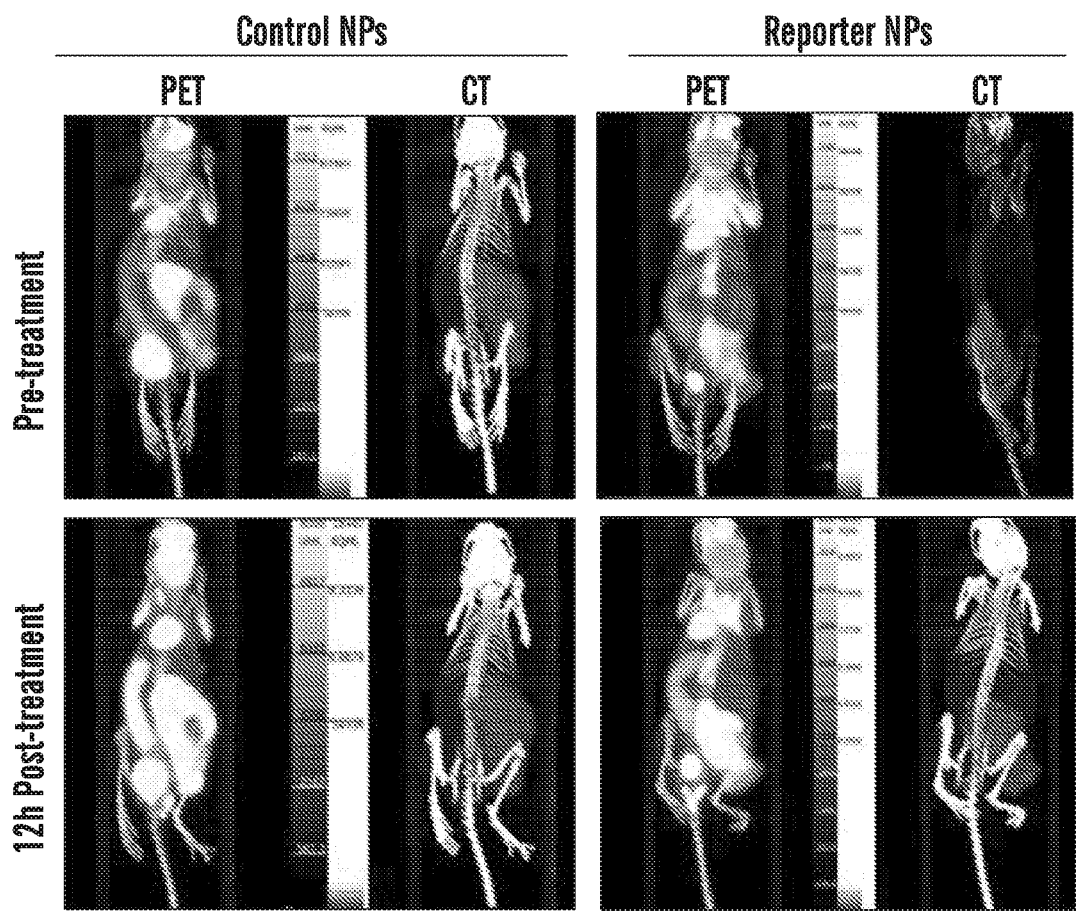
FIG. 17G is [$^{18}$F]FDG PET and CT images of representative animals in control NPs- and reporter NPs-treated groups before and 12 h after the treatment. The 4T1 breast tumor-bearing mice were treated with reporter NPs (equivalent to 15 mg/kg of paclitaxel) or control NPs (NPs with only the reporter element).
Figure 17H:
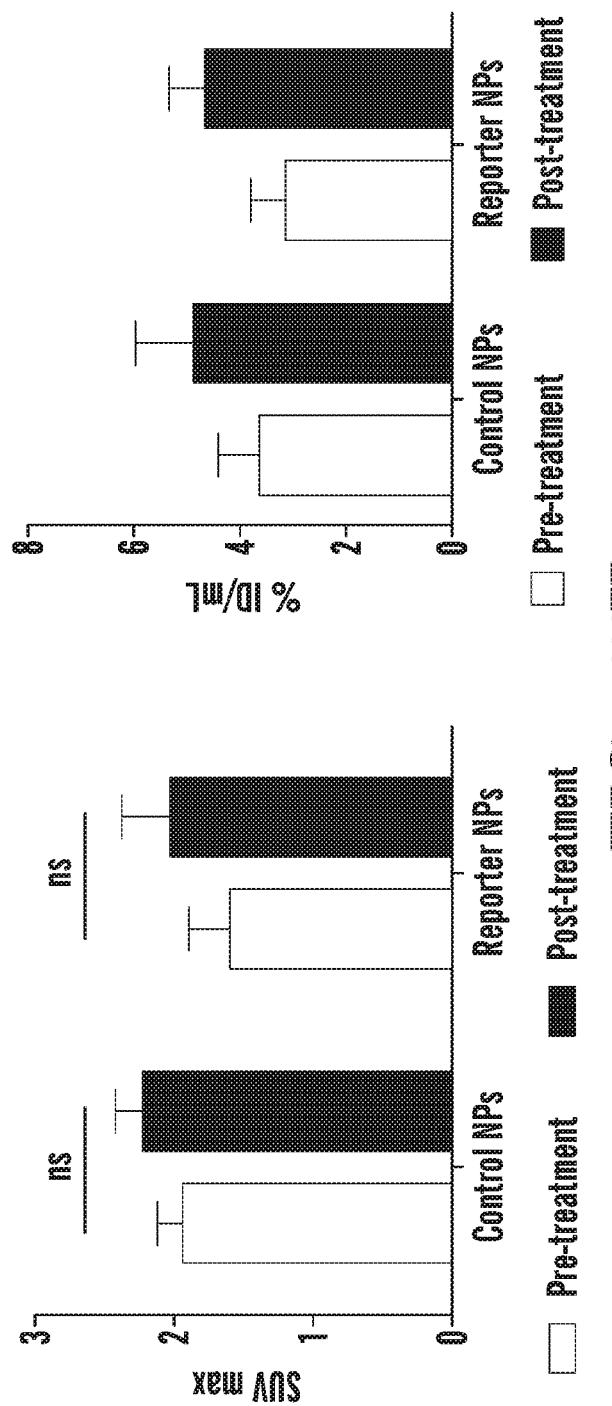
FIG. 17H are graphs showing maximum SUV (SUV max) and % injected dose per mL (% ID/mL) for different treatment groups from the study. Data represent mean±SEM (n=3-10, *P<0.05; ***P<0.001 vs. corresponding control NP-treated values for that time point, ANOVA followed by Bonferroni's post hoc test).
Figure 18A:
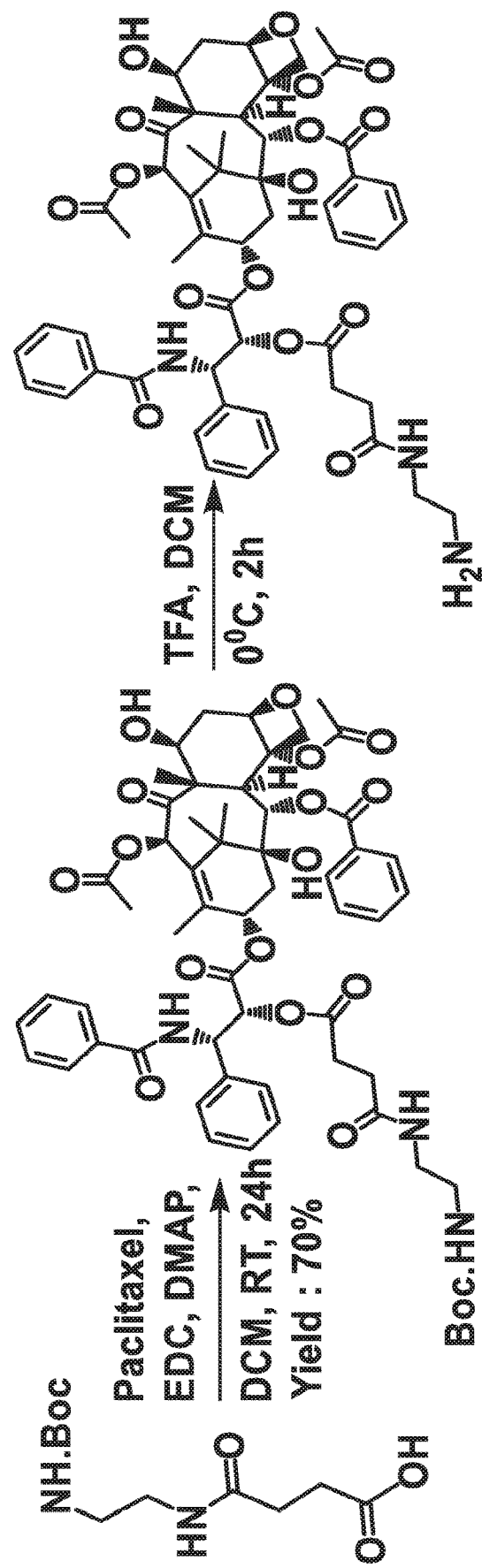
FIG. 18A is a scheme showing synthesis of effector element with flexible labile linker.
Figure 18B:
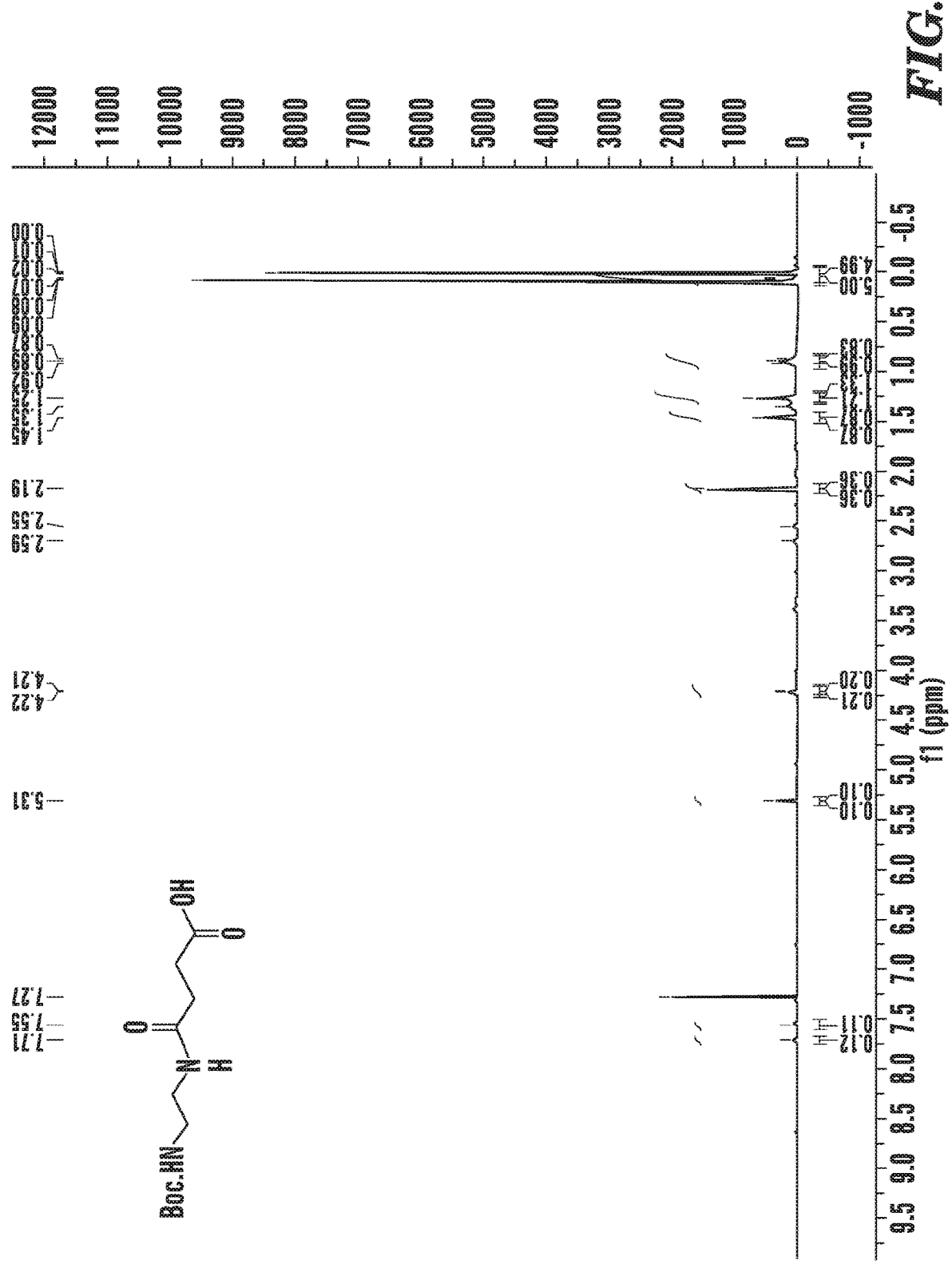
FIG. 18B shows $^1$H NMR spectrum of Boc protected linker.
Figure 18C:
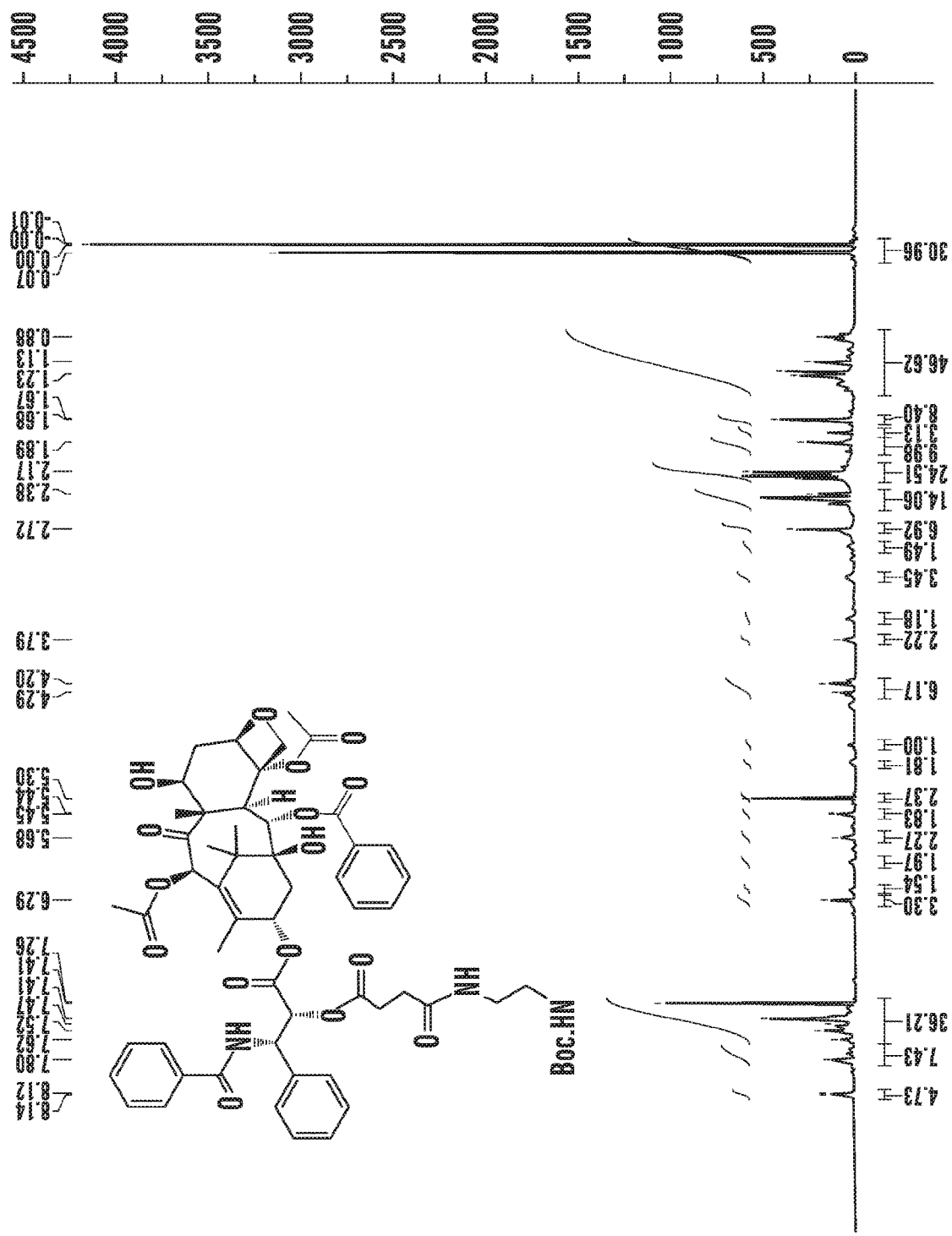
FIG. 18C shows $^1$H NMR spectrum of compound 1.
Figure 18D:
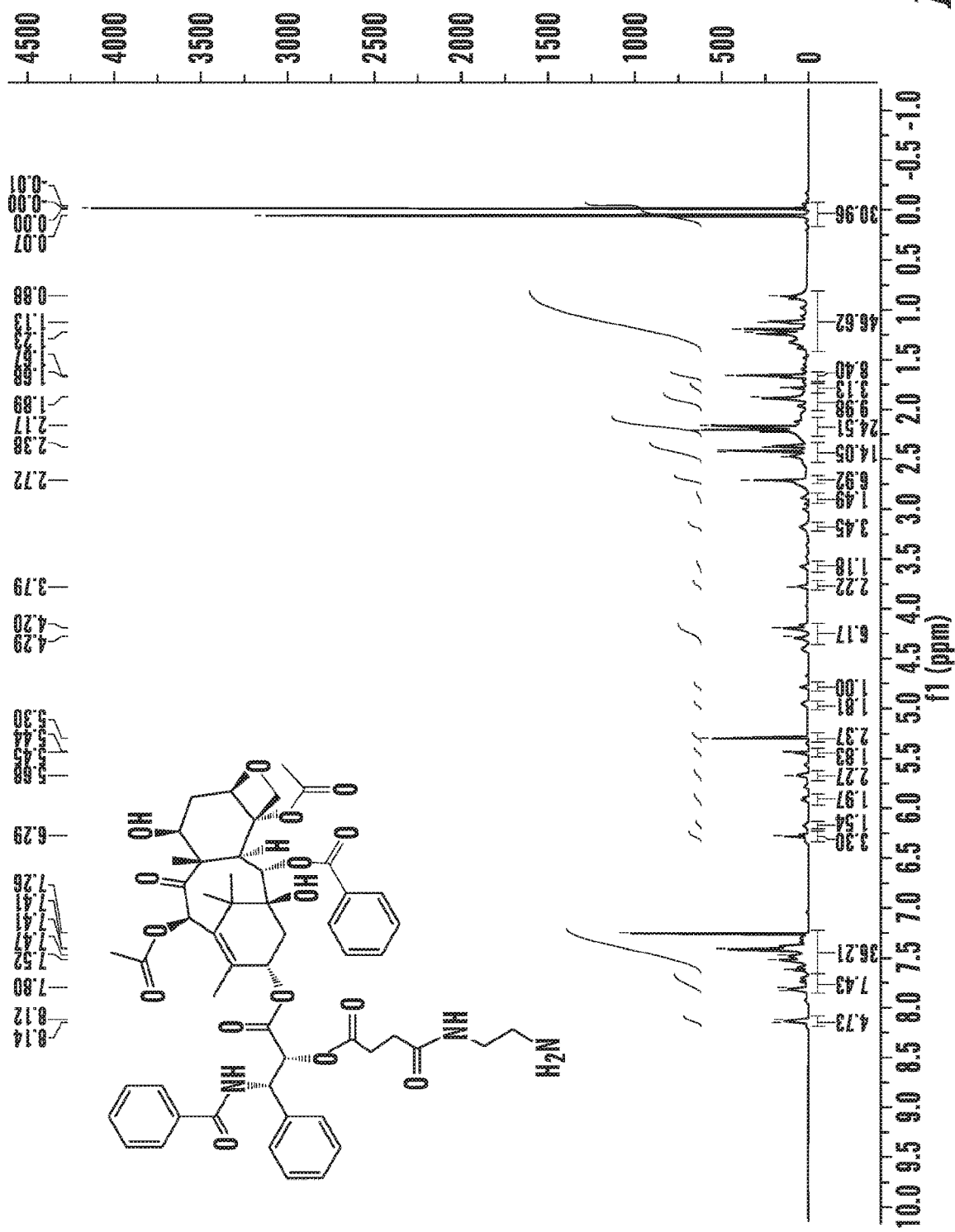
FIG. 18D shows $^1$H NMR spectrum of effector element.
Figure 18E:
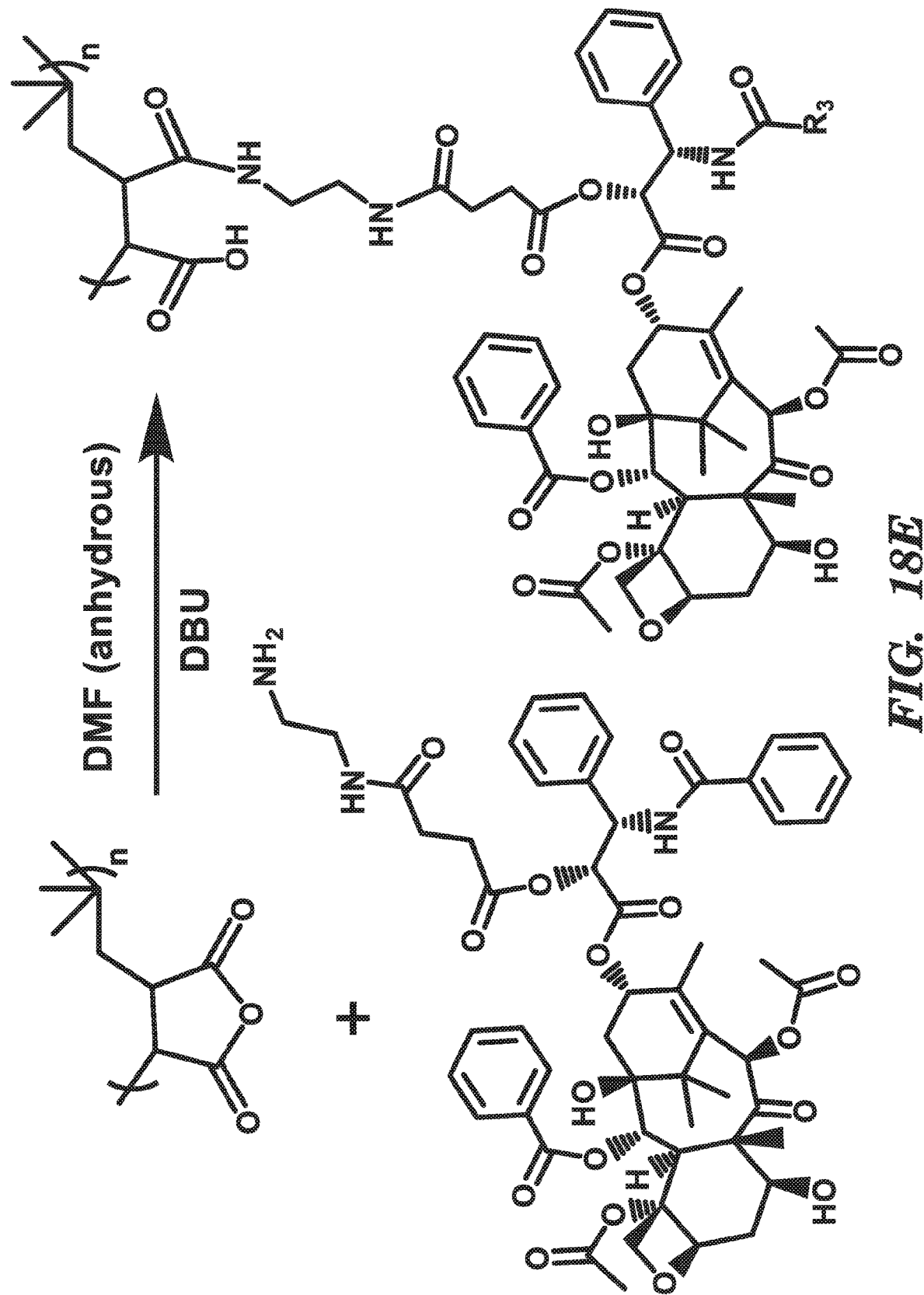
FIG. 18E is a schematic showing synthesis of effector element conjugated polymeric NPs.
Figures 18F, 18G:
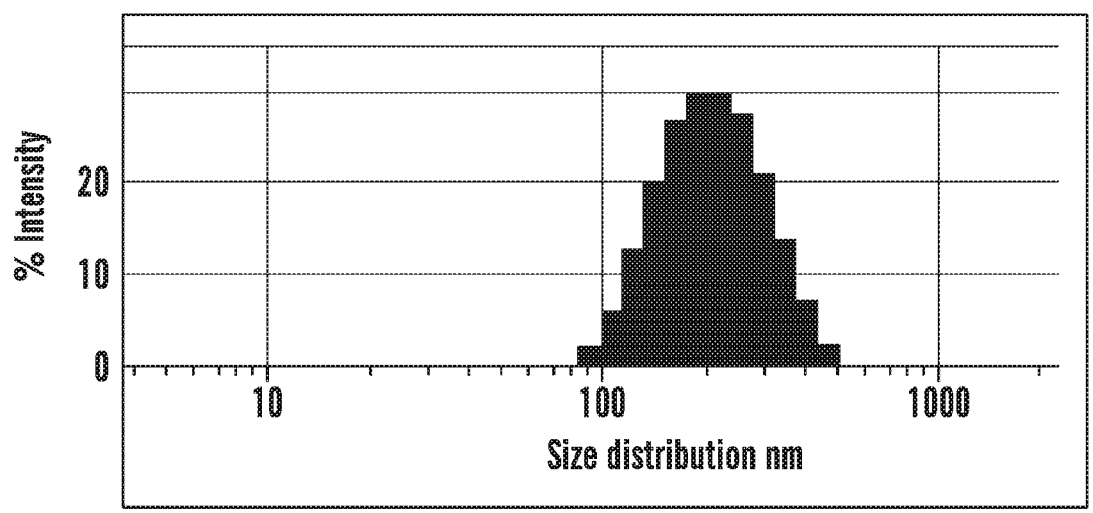
FIG. 18F is a table showing the optimization of polymer to effector element molar ratio to obtain the NPs with desired size range. The polymer was conjugated to different molar concentrations of effector element, and the NPs were synthesized by ultrasonication of the polymer construct in water for 10 min. The size and stability of resulting NPs was evaluated by measuring size by using DLS. Increase in polymer to effector element ratio resulted in higher size distribution, whereas at an optimized ration of 1:15, optimized size was obtained.
FIG. 18G is a graph showing size distribution of the effector element-NPs at an optimized molar ratio of polymer:effector element 1:15 as measured by DLS.
Figure 19A:
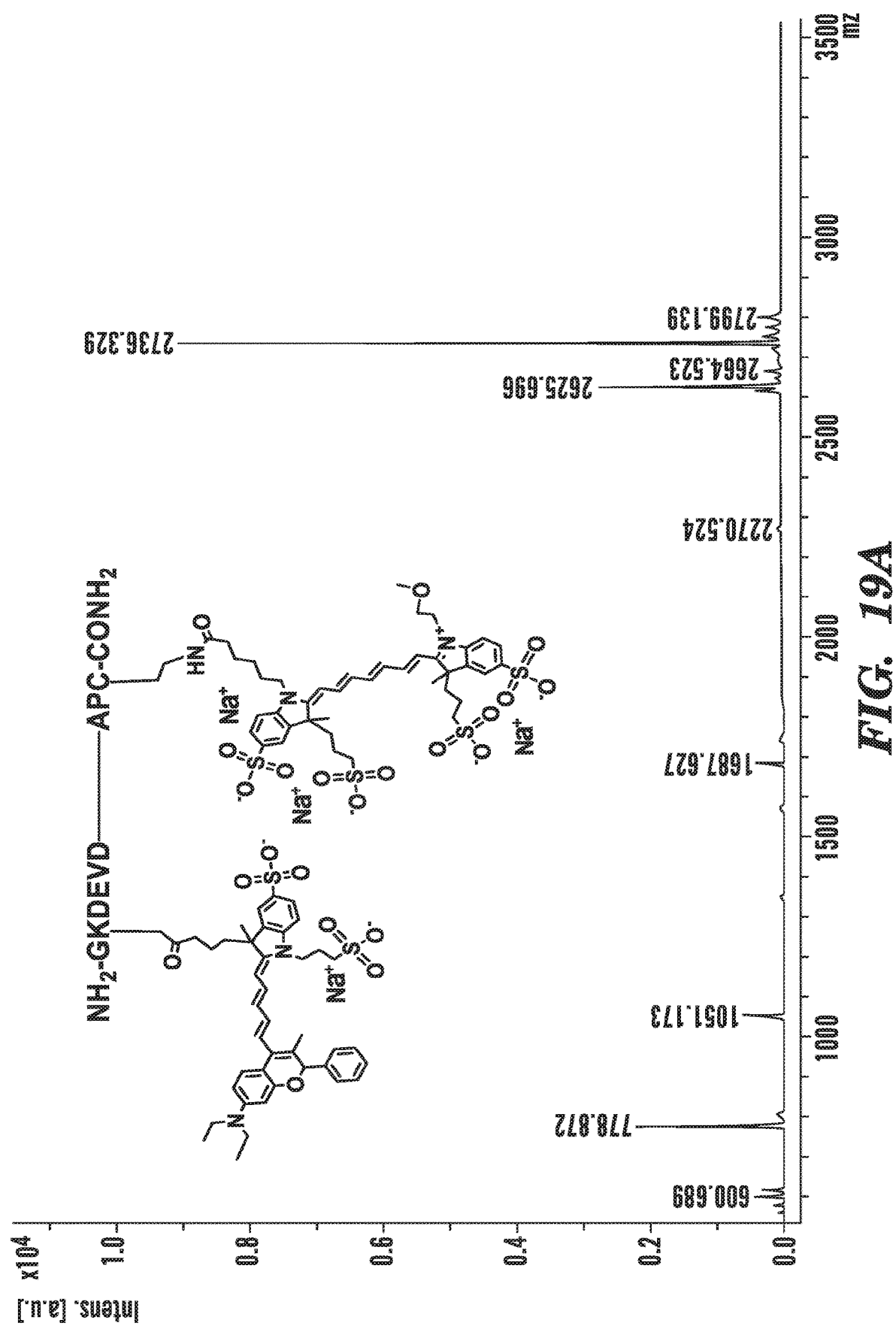
FIG. 19A shows mass spectrometric analysis of NIR FRET pair conjugated reporter element.
Figure 19B:
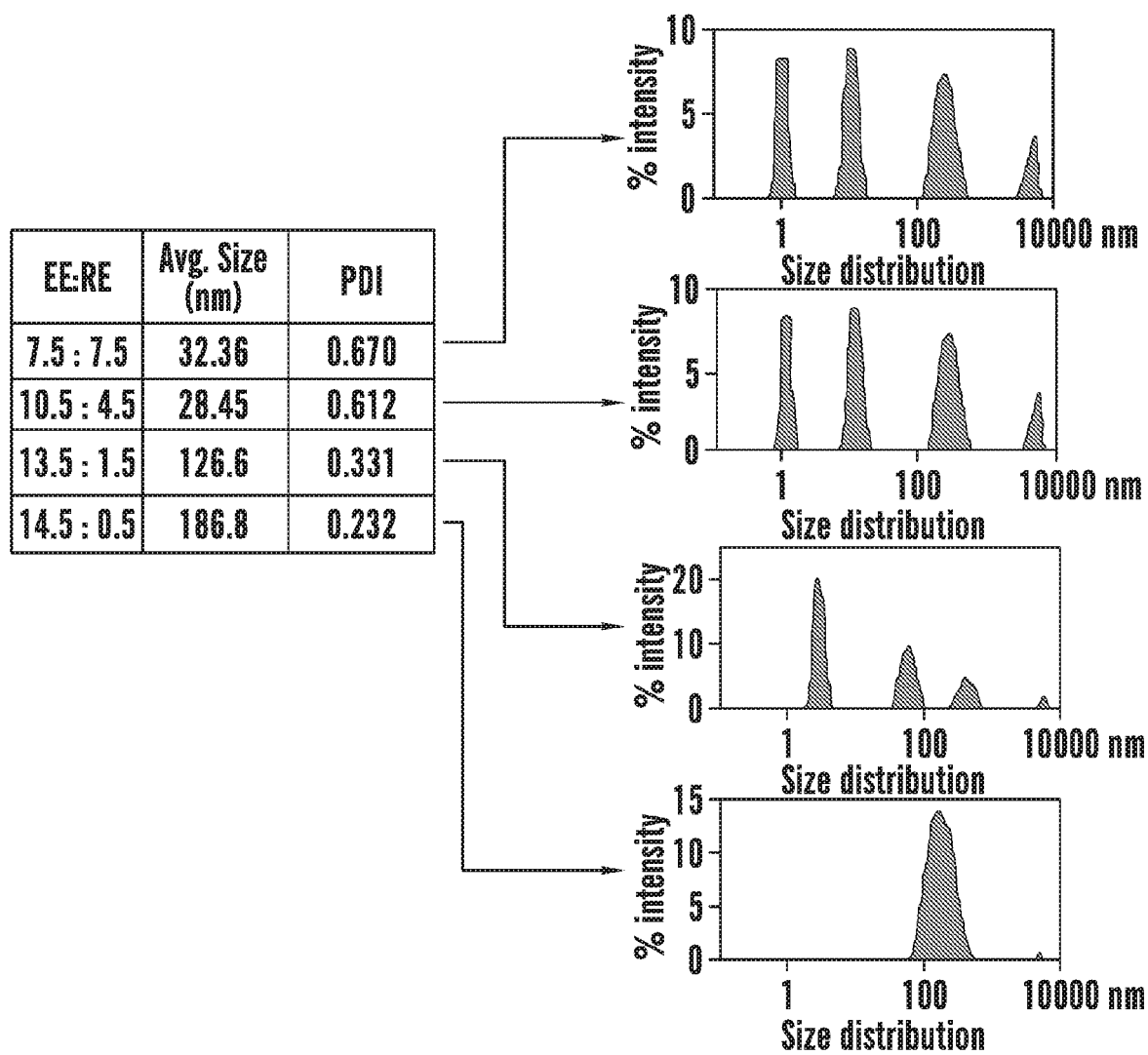
FIG. 19B is a table showing the optimization of ratio of effector elements (EE) and reporter elements (RE) at a constant stimuli-responsive elements to polymer ratio of 15:1. DLS shows the size distribution of reporter NPs with different effector element:reporter element ratio. Optimized size of 186.8 was obtained at a ratio of 14.5:0.5.
Figure 20A:
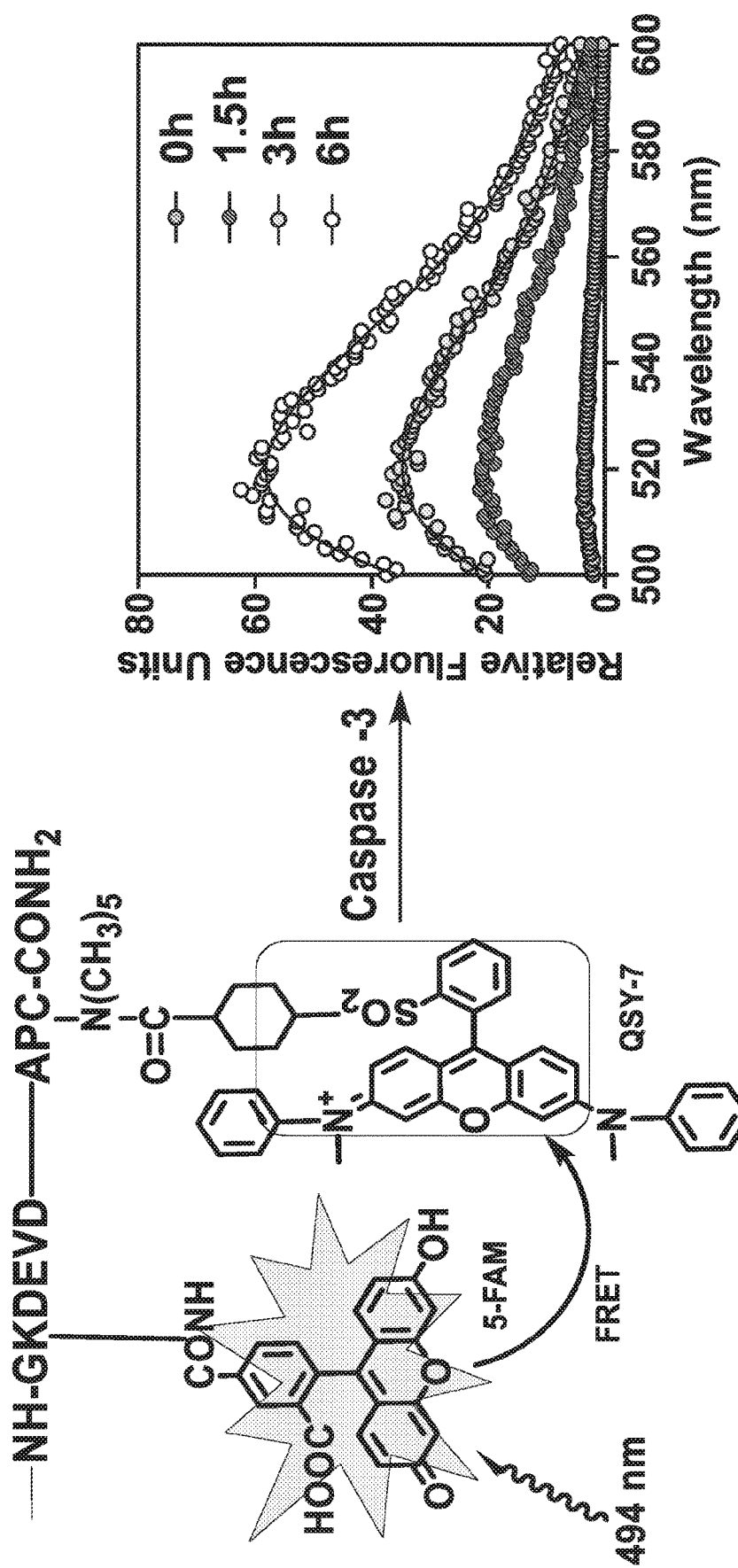
FIG. 20A shows in vitro characterization of reporter element conjugated with 5-FAM (green dye) and QSY7 (quencher) FRET pair. The graph shows time-dependent fluorescence activation of reporter element in presence of caspase-3. Reporter element (50 µM) was incubated in the presence of 50U caspase-3 enzyme at 37° C., which results in the cleavage of the DEVD sequence and removing the quenching effect of QSY7 on the fluorophore 5-FAM. The increase in fluorescence over time was monitored.
Figure 20B:
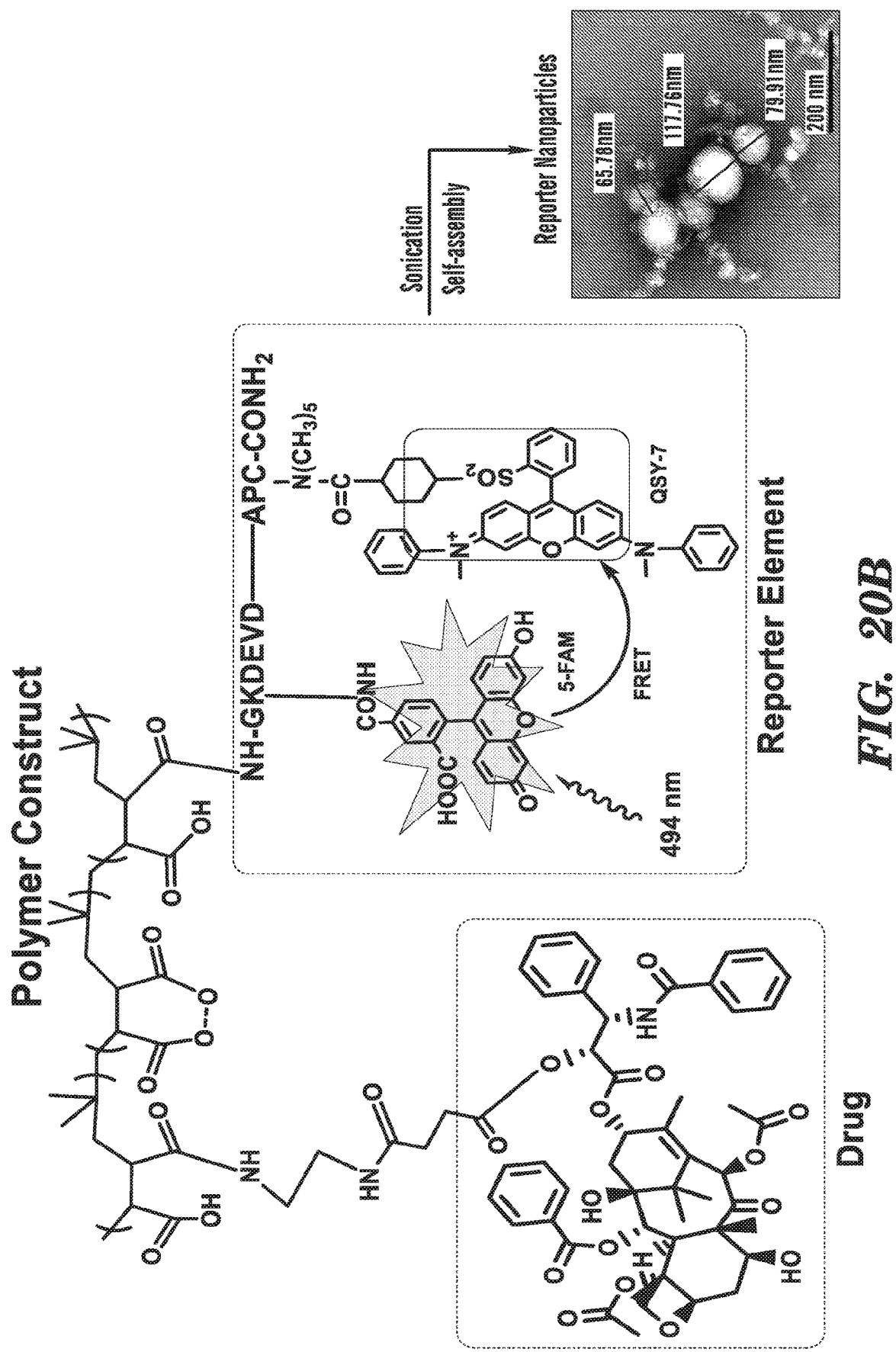
FIG. 20B shows synthesis and characterization of reporter NPs with 5-FAM (green dye) and QSY7 (quencher) FRET pair conjugated reporter element. The schematic shows the synthesis of reporter nanoparticle by ultrasonication of the polymer construct in water for 10 min at room temperature resulting in self assembled NPs. The polymer construct is synthesized by incubating effector element and a reporter element in the optimized molar ratio of 13.5:1.5. Representative high-resolution TEM shows the morphology and the size of the NPs. (Scale bar, 200 nm.)
Figure 21A:
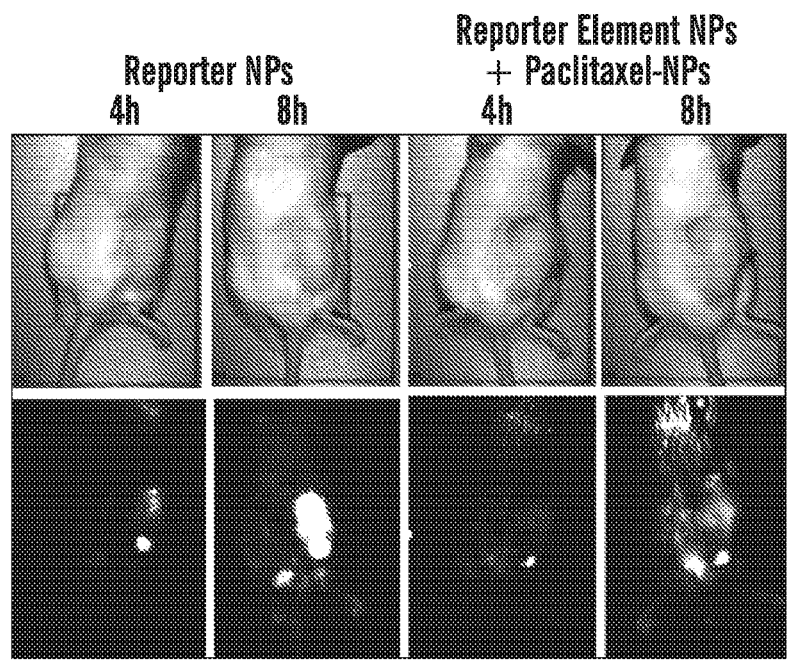
FIGS. 21A-21F shows in vivo characterization of In vivo characterization of reporter NPs.
Figure 21B:
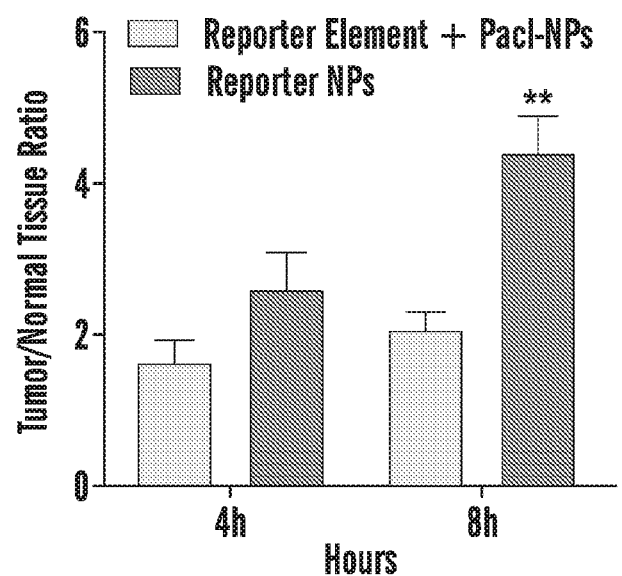
Figure 21C:
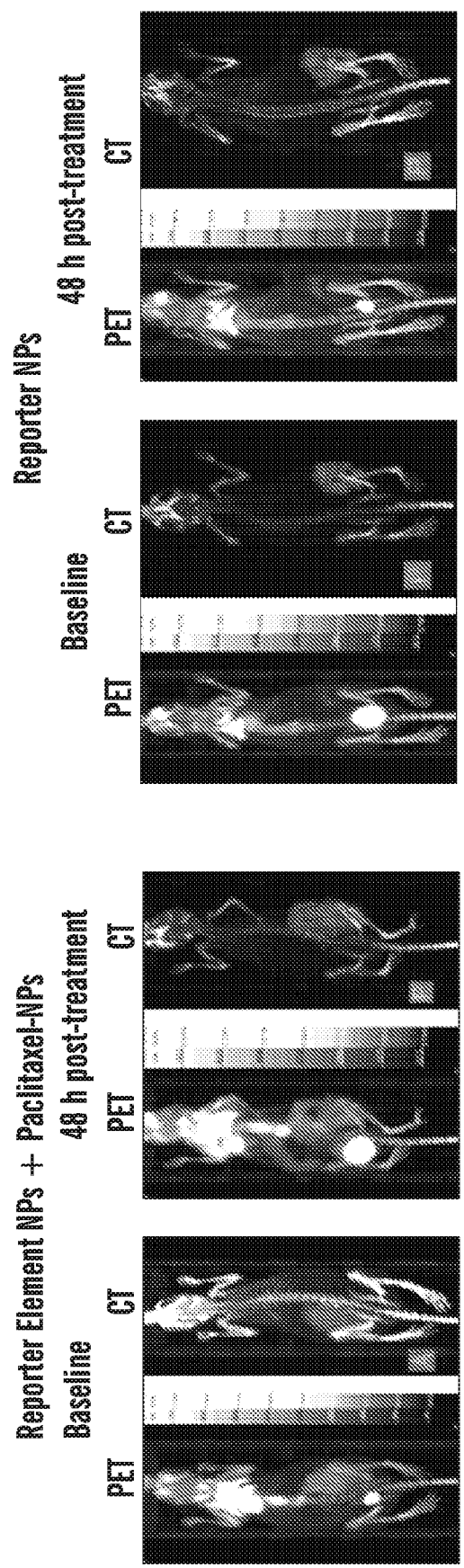
Figure 21D:
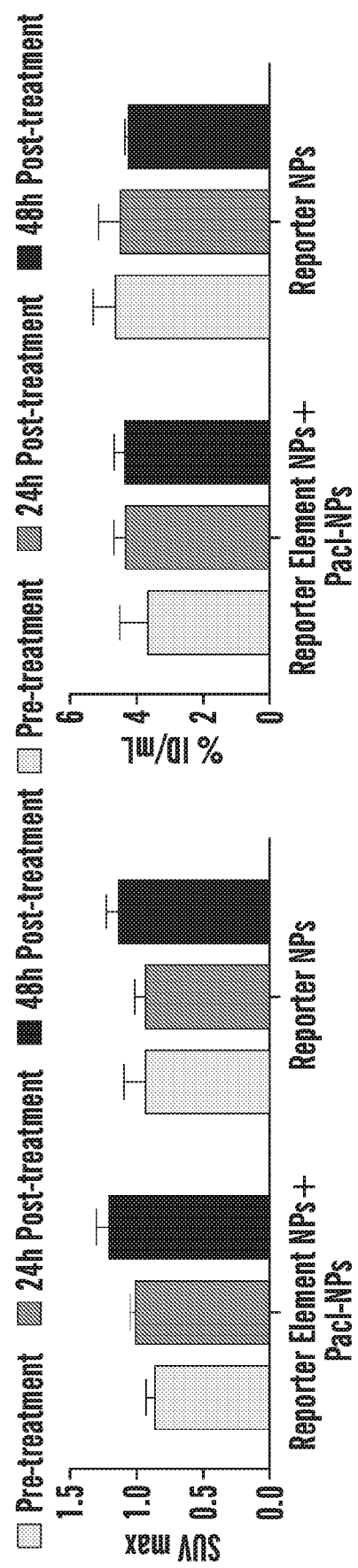
Figure 21E:
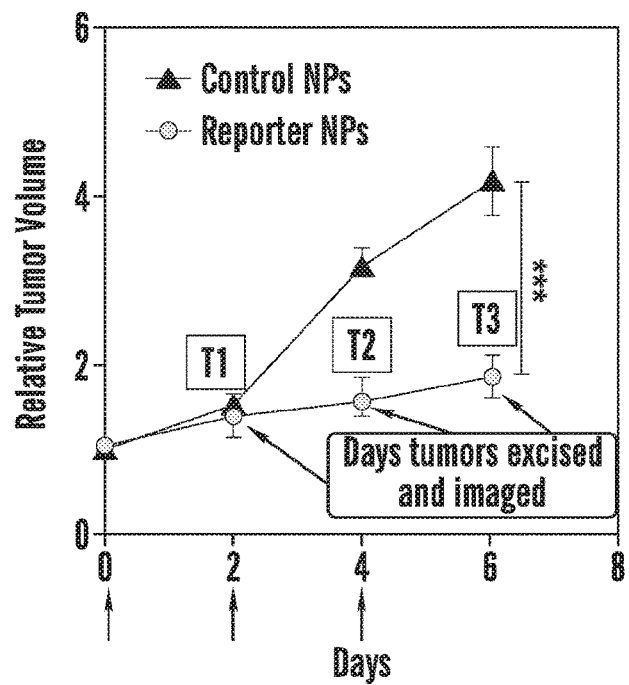
Figure 21F:
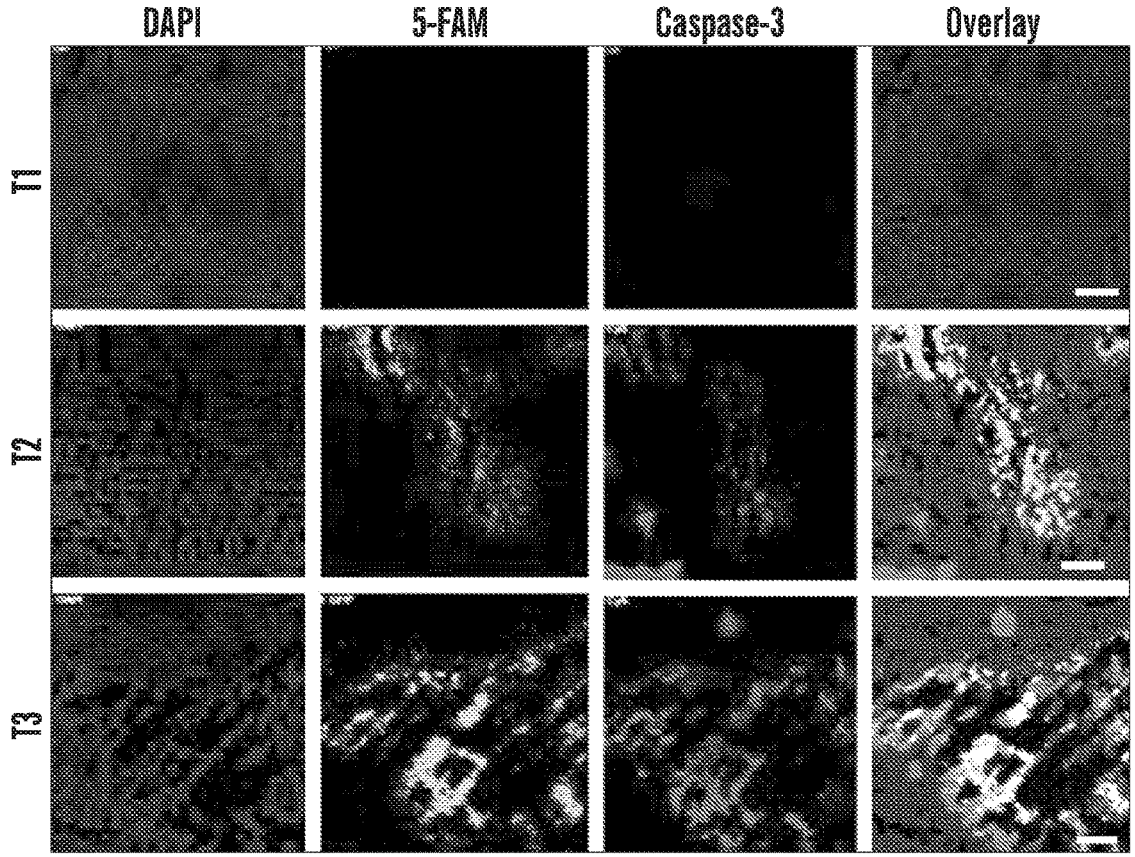
Figure 22A:
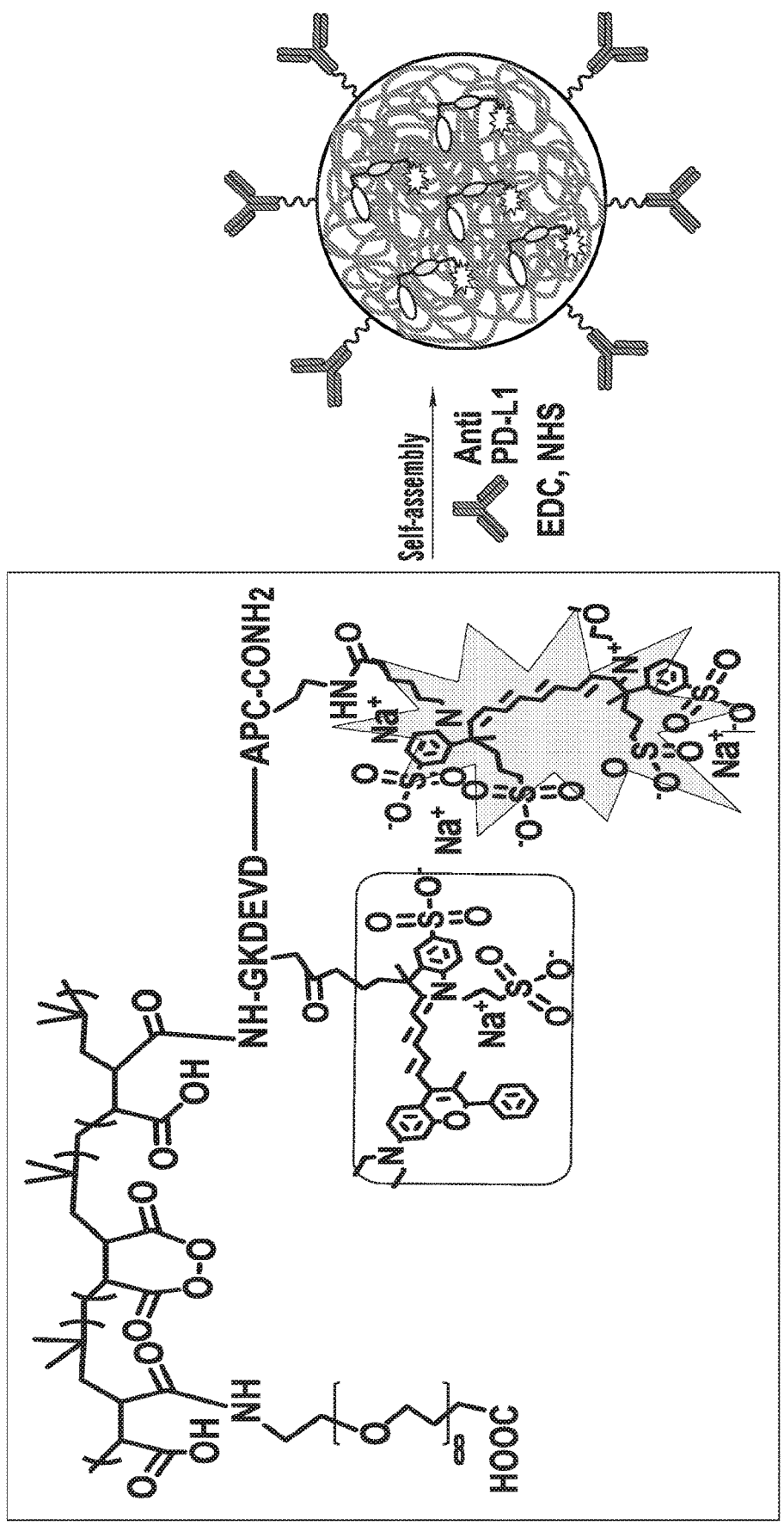
FIGS. 22A and 22B show synthesis and characterization of PD-L1 reporter NPs.
Figure 22B:
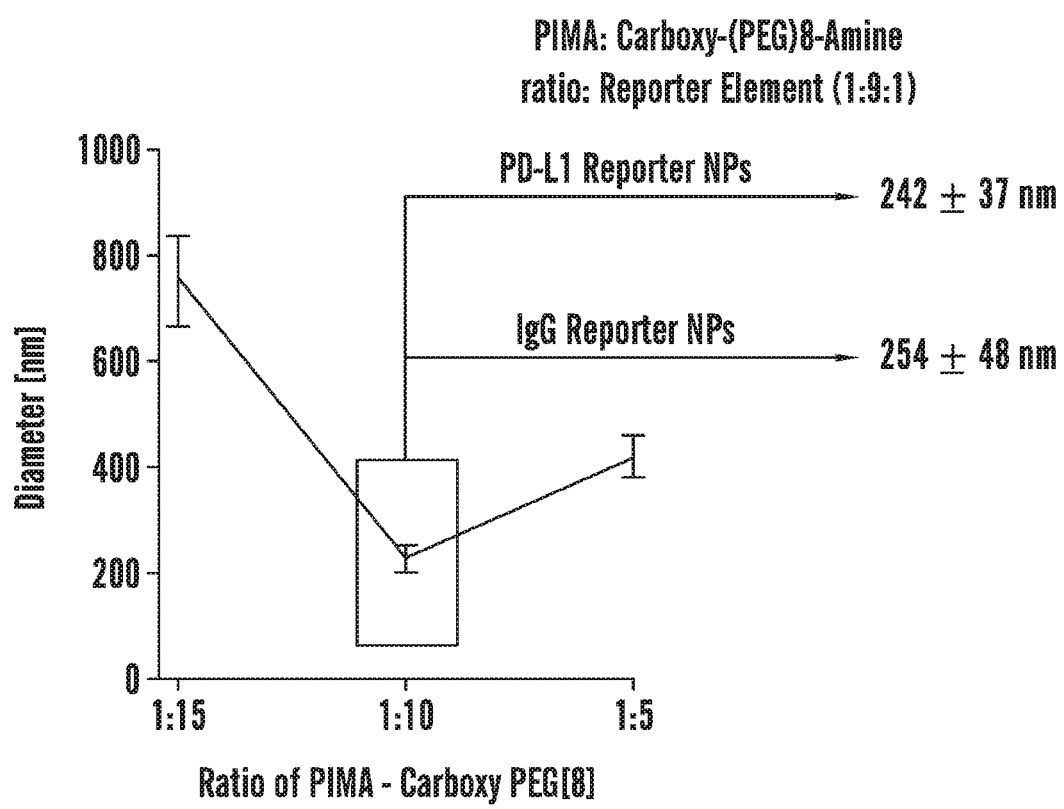

Example 13: BWHNP4 Synergize with Activated T Cells to Induce Increased Apoptosis of Cancer Cells It was then tested whether PD-L1 conjugated reporter nanoparticles (BWHNP4) significantly block immunosuppressive PD1-PDL1 interactions and induce potent T cell mediated immune response leading to apoptosis and higher caspase activation in T cells-cancer cells co-culture assay. At first, the PD-L1 overexpressing B16-F10 melanoma cells were treated with PD-L1 antibody coated reporter nanoparticles and subsequently incubated with activated T cells for 6h and 24h. The apoptosis was monitored by measuring the increase in expression of cleaved caspase-3 in the cancer cells at different time points. As shown in FIG. 13, incubation of BWHNP4 with cancer cells resulted in rapid T cell-mediated apoptosis of cancer cells. BWHNP4 only (without activated T cells) did not exhibit any toxicity to the cancer cells.

Content of all patents and other publications identified herein is expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A lipid-based reporter material platform comprising a drug covalently linked to a first lipid and a reporter element covalently linked to a second lipid, wherein the drug and the reporter element are in proximity to each other, and wherein the reporter element comprises a first cleavable linker such that the first cleavable linker is cleaved only after the drug has induced a physiological or chemical change in a tumor or surrounding environment and the reporter element generates a detectable signal upon cleavage of said cleavable linker.

2. The lipid-based reporter material platform of claim 1, wherein the distance between the drug and the reporter element is 0.5 nm 10 nm.

3. The lipid-based reporter material platform of claim 1, wherein the reporter element is covalently linked to the second lipid by a second cleavable linker.

4. The lipid-based reporter material platform of claim 1, wherein the reporter element comprises a fluorescent donor and an acceptor in proximity to each other such that the acceptor quenches fluorescence of the donor.

5. A theranostic composition comprising the lipid-based reporter material platform of claim 1.

6. A pharmaceutical composition comprising the lipid-based reporter material platform of claim 1 and a pharmaceutically acceptable excipient or carrier.

7. A kit comprising the lipid-based reporter material platform of claim 1 and packaging materials therefor.

8. A method for treatment of a disease comprising administering the lipid-based reporter material platform of claim 1 to a subject in need thereof.

9. A method of monitoring efficacy of a drug, comprising
(i) administering the lipid-based reporter material platform of claim 1 to a subject in need thereof; and
(ii) measuring or detecting a detectable signal produced by the reporter element.

10. A method for determining susceptibility of a subject to a treatment regime, comprising:
(i) administering the lipid-based reporter material platform of claim 1 to a subject in need thereof; and
(ii) measuring or detecting a detectable signal produced by the reporter element, wherein an increase in the detectable signal indicates the subject is susceptible to treatment with the drug.

11. The lipid-based reporter material platform of claim 1, wherein the lipid-based reporter material self-assembles to form a particle.

* * * * *